United States Patent
Jarc et al.

(10) Patent No.: US 10,278,782 B2
(45) Date of Patent: May 7, 2019

(54) MEDICAL DEVICES, SYSTEMS, AND METHODS USING EYE GAZE TRACKING

(71) Applicant: Intuitive Surgical Operations, Inc., Sunnyvale, CA (US)

(72) Inventors: Anthony Michael Jarc, Sunnyvale, CA (US); Henry C. Lin, San Jose, CA (US); Jonathan Michael Sorger, Belmont, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 282 days.

(21) Appl. No.: 15/126,074

(22) PCT Filed: Mar. 18, 2015

(86) PCT No.: PCT/US2015/021309
§ 371 (c)(1),
(2) Date: Sep. 14, 2016

(87) PCT Pub. No.: WO2015/143067
PCT Pub. Date: Sep. 24, 2015

(65) Prior Publication Data
US 2017/0172675 A1    Jun. 22, 2017

Related U.S. Application Data

(60) Provisional application No. 61/955,314, filed on Mar. 19, 2014, provisional application No. 61/955,355, filed on Mar. 19, 2014.

(51) Int. Cl.
*A61B 34/00* (2016.01)
*A61B 34/35* (2016.01)
(Continued)

(52) U.S. Cl.
CPC .......... *A61B 34/35* (2016.02); *A61B 1/00193* (2013.01); *A61B 17/00234* (2013.01);
(Continued)

(58) Field of Classification Search
USPC .................................................. 700/245–264
See application file for complete search history.

(56) References Cited

U.S. PATENT DOCUMENTS 5,204,942 A * 4/1993 Otera ................. G05B 19/4182
700/248
5,553,609 A * 9/1996 Chen ................... G06F 19/3418
600/301
(Continued)

FOREIGN PATENT DOCUMENTS

CN         102958464 A      3/2013
WO      WO-2013175465 A1    11/2013
(Continued)

OTHER PUBLICATIONS

Ahmidi N., et al., "Surgical Task and Skill Classification from Eye Tracking and Tool Motion in Minimally Invasive Surgery," Medical Image Computing and Computer-Assisted Intervention—MICCAI, 2010, vol. 6363, pp. 295-302.
(Continued)

*Primary Examiner* — Jonathan L Sample

(57) ABSTRACT

Described herein is a teleoperational medical system for performing a medical procedure in a surgical field. The teleoperational system comprises an eye tracking unit and a control unit. The eye tracking unit includes an image display configured to display to a user an image of the surgical field, at least one eye tracker configured to measure data about a gaze point of the user, and a processor configured to process the data to determine a viewing location in the displayed image at which the gaze point of the user is directed. The control unit is configured to control at least one function of
(Continued)

the teleoperational medical system based upon the determined viewing location.

58 Claims, 20 Drawing Sheets

(51) Int. Cl.
| | |
|---|---|
| *G06F 3/01* | (2006.01) |
| *G02B 27/00* | (2006.01) |
| *A61B 90/00* | (2016.01) |
| *A61B 1/00* | (2006.01) |
| *A61B 17/00* | (2006.01) |

(52) U.S. Cl.
CPC ............ *A61B 34/71* (2016.02); *A61B 90/361* (2016.02); *A61B 90/37* (2016.02); *G02B 27/0093* (2013.01); *G06F 3/013* (2013.01); *A61B 2017/00216* (2013.01); *A61B 2090/371* (2016.02); *A61B 2090/372* (2016.02)

(56) References Cited

U.S. PATENT DOCUMENTS

| | | | | |
|---|---|---|---|---|
| 5,704,791 | A * | 1/1998 | Gillio | G09B 5/14 434/262 |
| 5,855,553 | A * | 1/1999 | Tajima | A61B 34/70 600/407 |
| 5,876,325 | A * | 3/1999 | Mizuno | A61B 1/00048 600/102 |
| 5,931,832 | A * | 8/1999 | Jensen | B25J 9/1065 128/898 |
| 6,090,051 | A | 7/2000 | Marshall | |
| 6,459,926 | B1 * | 10/2002 | Nowlin | A61B 34/70 600/102 |
| 6,578,962 | B1 | 6/2003 | Amir et al. | |
| 6,659,939 | B2 * | 12/2003 | Moll | A61B 34/30 600/102 |
| 6,799,065 | B1 * | 9/2004 | Niemeyer | A61B 1/00149 600/407 |
| 6,852,107 | B2 * | 2/2005 | Wang | G05B 15/02 606/1 |
| 6,892,112 | B2 * | 5/2005 | Wang | A61B 34/70 340/7.35 |
| 6,951,535 | B2 * | 10/2005 | Ghodoussi | G06F 19/3418 600/101 |
| 7,245,202 | B2 * | 7/2007 | Levin | H04L 12/282 307/114 |
| 7,259,652 | B2 * | 8/2007 | Wang | A61B 17/00 340/3.7 |
| 7,865,266 | B2 * | 1/2011 | Moll | A61B 34/30 700/245 |
| 7,914,521 | B2 * | 3/2011 | Wang | B25J 9/1689 414/2 |
| 8,527,094 | B2 * | 9/2013 | Kumar | G09B 23/28 700/259 |
| 8,831,782 | B2 * | 9/2014 | Itkowitz | A61B 34/30 700/264 |
| 8,914,150 | B2 * | 12/2014 | Moll | A61B 34/30 700/246 |
| 9,039,681 | B2 * | 5/2015 | Wang | G05B 15/02 606/1 |
| 9,107,633 | B2 * | 8/2015 | Muller | A61B 6/0407 |
| 9,119,654 | B2 * | 9/2015 | Ramans | A61B 34/71 |
| 9,307,894 | B2 | 4/2016 | Von et al. | |
| 9,360,934 | B2 | 6/2016 | Ruiz et al. | |
| 2002/0029095 | A1 * | 3/2002 | Kosaka | B25J 9/1674 700/245 |
| 2002/0105482 | A1 * | 8/2002 | Lemelson | G06F 3/013 345/7 |
| 2003/0020755 | A1 * | 1/2003 | Lemelson | G06F 3/013 715/786 |
| 2003/0050733 | A1 * | 3/2003 | Wang | A61B 34/70 700/245 |
| 2003/0169213 | A1 | 9/2003 | Spero | |
| 2005/0206583 | A1 * | 9/2005 | Lemelson | A61B 1/00048 345/7 |
| 2006/0082542 | A1 * | 4/2006 | Morita | A61B 5/7475 345/156 |
| 2006/0100642 | A1 | 5/2006 | Yang et al. | |
| 2006/0109237 | A1 * | 5/2006 | Morita | G06F 3/013 345/156 |
| 2006/0166681 | A1 * | 7/2006 | Lohbihler | G01S 5/02 455/456.2 |
| 2006/0178559 | A1 * | 8/2006 | Kumar | A61B 34/37 600/109 |
| 2006/0258938 | A1 * | 11/2006 | Hoffman | A61B 1/00193 600/424 |
| 2008/0253519 | A1 * | 10/2008 | Bonfiglio | A61B 6/00 378/65 |
| 2009/0036902 | A1 * | 2/2009 | DiMaio | A61B 34/10 606/130 |
| 2009/0248036 | A1 * | 10/2009 | Hoffman | A61B 1/045 606/130 |
| 2009/0268010 | A1 | 10/2009 | Zhao et al. | |
| 2009/0270678 | A1 | 10/2009 | Scott et al. | |
| 2011/0118748 | A1 * | 5/2011 | Itkowitz | A61B 34/30 606/130 |
| 2011/0228051 | A1 | 9/2011 | Dedeoglu et al. | |
| 2011/0299034 | A1 | 12/2011 | Walsh et al. | |
| 2012/0029694 | A1 * | 2/2012 | Muller | A61B 6/0407 700/248 |
| 2012/0069166 | A1 | 3/2012 | Kunz et al. | |
| 2012/0147328 | A1 | 6/2012 | Yahav | |
| 2013/0023899 | A1 * | 1/2013 | Green | H04N 13/398 606/130 |
| 2013/0030571 | A1 * | 1/2013 | Ruiz Morales | G06F 3/013 700/259 |
| 2013/0107207 | A1 * | 5/2013 | Zhao | A61B 3/0058 351/206 |
| 2013/0331859 | A1 * | 12/2013 | Kumar | A61B 34/37 606/130 |
| 2014/0024889 | A1 * | 1/2014 | Xiaoli | A61B 1/00039 600/102 |
| 2014/0160004 | A1 * | 6/2014 | Katz | G06F 3/013 345/156 |
| 2014/0160434 | A1 * | 6/2014 | Brown, Jr. | A61B 3/113 351/210 |
| 2014/0163736 | A1 * | 6/2014 | Azizian | A61B 6/102 700/259 |
| 2014/0195048 | A1 * | 7/2014 | Moll | A61B 34/30 700/247 |
| 2014/0275760 | A1 * | 9/2014 | Lee | A61B 1/00045 600/102 |
| 2014/0375789 | A1 | 12/2014 | Lou et al. | |
| 2015/0173846 | A1 | 6/2015 | Schneider et al. | |
| 2016/0183930 | A1 | 6/2016 | Herzlinger et al. | |
| 2017/0180720 | A1 * | 6/2017 | Jarc | G02B 21/0012 |

FOREIGN PATENT DOCUMENTS

| | | |
|---|---|---|
| WO | WO-2015143067 A1 | 9/2015 |
| WO | WO-2015143073 A1 | 9/2015 |

OTHER PUBLICATIONS

International Preliminary Report on Patentability for Application No. PCT/US15/21309, dated Sep. 29, 2016, 14 pages.
International Search Report and Written Opinion for Application No. PCT/US15/21309, dated Jun. 26, 2015, 17 pages.
Reiley C.E., et al., "Review of Methods for Objective Surgical Skill Evaluation," Surgical Endoscopy, Feb. 2011, vol. 25, pp. 356-366.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Chen J et al., et al., "A Robust 3D Eye Gaze Tracking System Using Noise Reduction," Eye Tracking Research & Applications: Proceedings ; ETRA 2008 ; [Eye Tracking Research and Applications

(56) References Cited

OTHER PUBLICATIONS

Symposium] ; Savanna, Georgia, USA, Mar. 26-28, 2008, ACM, New York, NY, Mar. 26, 2008 (Mar. 26, 2008), pp. 189-196, XP058345555, DOI: 10.1145/1 344471. 1, 1344518, ISBN: 978-1-59593-982-1
Extended European Search Report for Application No. EP15765996.2, dated Nov. 17, 2017, 9 pages.
Hansen D.W. et al., "In the Eye of the Beholder: A Survey of Models for Eyes and Gaze," IEEE Transactions on Pattern Analysis and Machine Intelligence. IEEE Computersociety, USA, vol. 32 (3), Mar. 1, 2010 (Mar. 1, 2010), pp. 478-500, XP011280658, ISSN: 0162-8828, DOI: 10.1109/TPAMI. 2009.30.
Kohlbecher S., et al, "Calibration—Free Eye Tracking by Reconstruction of the Pupil Ellipse in 3DSpace," Eye Tracking Research & Applications: Proceedings; ETRA 2008; [Eye Tracking Research and Applications Symposium] ; Savanna, Georgia, USA, Mar. 26-28, 2008, ACM, New York, NY, Mar. 26, 2008 (Mar. 26, 2008), pp. 135-138, XP058345545,DOI: 10.1145/1344471.1344506, ISBN: 978-1-59593-982-1.
Extended European Search Report for Application No. EP15765508.5, dated Mar. 6, 2018, 14 pages.
International Preliminary Report on Patentability for Application No. PCT/US15/21315, dated Sep. 29, 2016, 10 pages.
International Search Report and Written Opinion for Application No. PCT/US15/21315, dated Aug. 25, 2015, 14 pages.
Partial Supplementary European Search Report for Application No. 15765508.5, dated Dec. 1, 2017, 17 pages.

\* cited by examiner

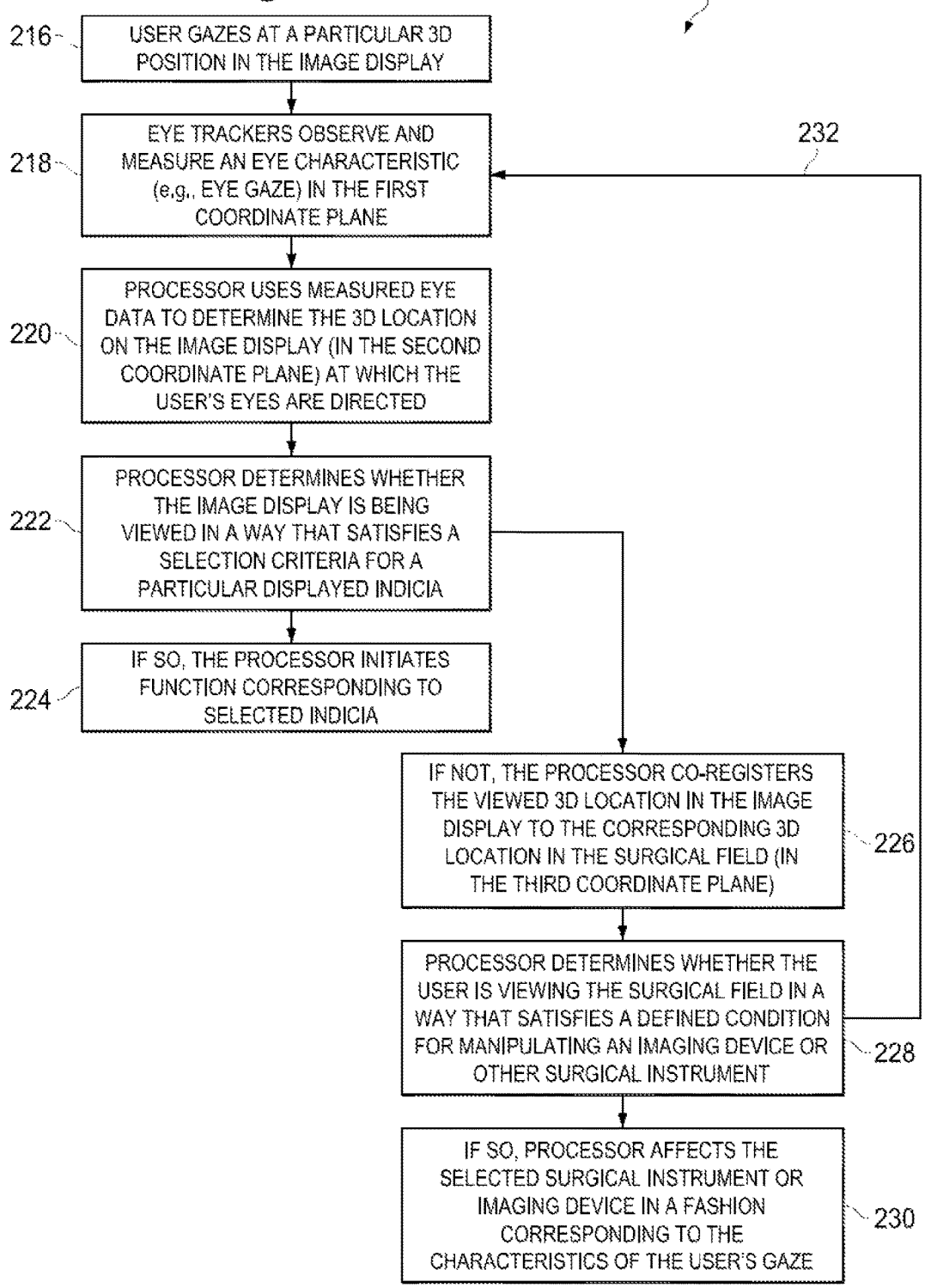

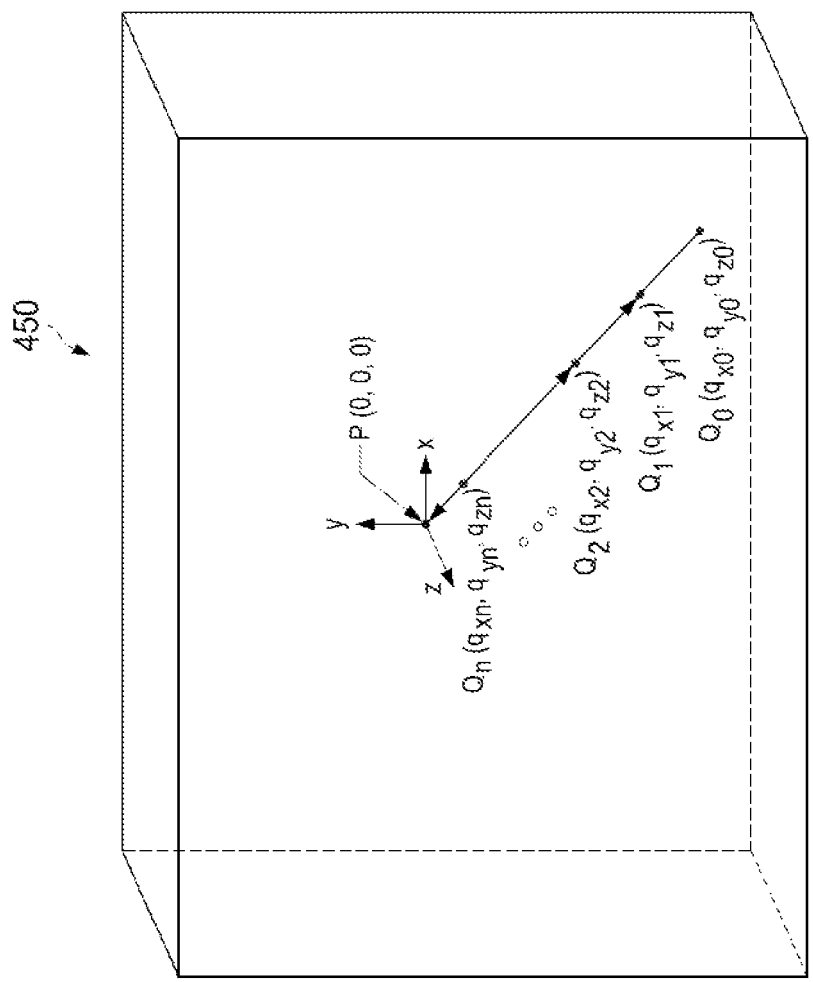

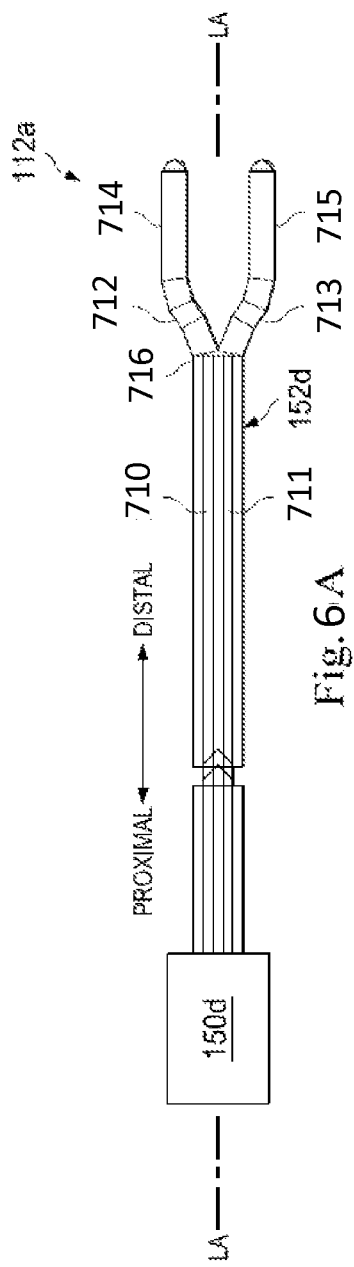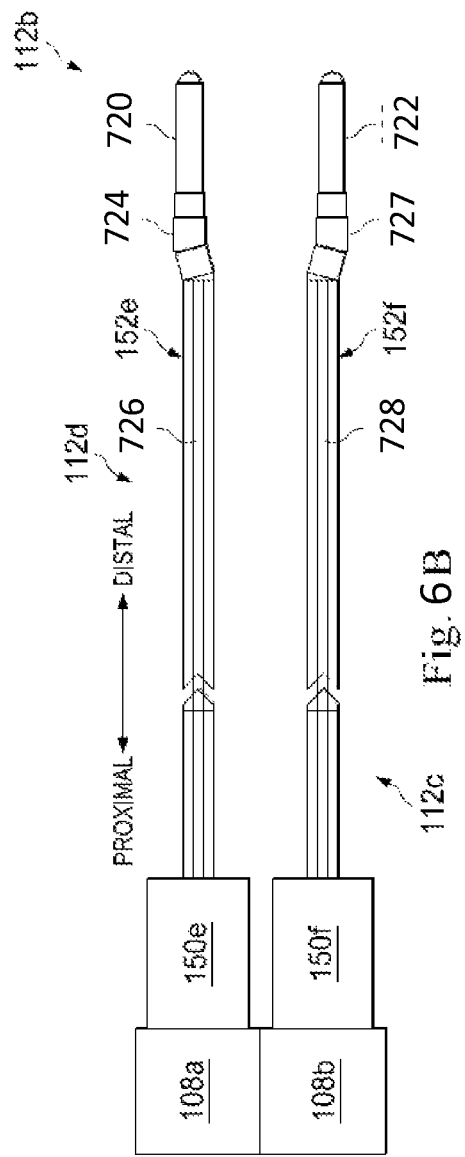

MEDICAL DEVICES, SYSTEMS, AND METHODS USING EYE GAZE TRACKING

RELATED APPLICATIONS

This patent application is the U.S. national phase of International Application No. PCT/US2015/021309, filed Mar. 18, 2015, which designated the U.S. and claims priority to and the benefit of the filing date of U.S. Provisional Patent Application 61/955,314, titled "Medical Devices, Systems, and Methods Using Eye Gaze Tracking," filed Mar. 19, 2014, and U.S. Provisional Patent Application 61/955,355, titled "Medical Devices, Systems, and Methods Using Eye Gaze Tracking for Secondary Imaging," filed Mar. 19, 2014, which are all incorporated by reference herein in their entirety.

BACKGROUND

Surgical procedures can be performed using a teleoperational medical system in a minimally invasive manner. The benefits of a minimally invasive surgery are well known and include less patient trauma, less blood loss, and faster recovery times when compared to traditional, open incision surgery. In addition, the use of a teleoperational medical system, such as the DA VINCI® Surgical System commercialized by Intuitive Surgical, Inc., Sunnyvale, Calif., is known. Such teleoperational medical systems may allow a surgeon to operate with intuitive control and increased precision when compared to manual minimally invasive surgeries.

A teleoperational medical system may include one or more instruments that are coupled to one or more robotic arms. If the system is used to perform minimally invasive surgery, the instruments may access the surgical area through one or more small openings in the patient, such as small incisions or natural orifices, such as, for example, the mouth, urethra, or anus. In some cases, rather than having the instrument(s) directly inserted through the opening(s), a cannula or other guide element can be inserted into each opening and the instrument can be inserted through the cannula to access the surgical area. An imaging tool such as an endoscope can be used to view the surgical area, and the image captured by the imaging tool can be displayed on an image display to be viewed by the surgeon during a surgery.

It is desirable to provide teleoperational medical systems that can be effectively controlled and monitored for various applications during minimally invasive medical procedures. The systems and methods disclosed herein overcome one or more of the deficiencies of the prior art.

SUMMARY

In one exemplary aspect, the present disclosure is directed to a teleoperational medical system comprising an eye tracking unit and a control unit. In one aspect, the eye tracking unit includes an image display configured to display to a user an image of the surgical field, and at least one eye tracker configured to measure data about a gaze point of the user. In one aspect, the eye tracking unit includes a processor configured to process the data to determine a viewing location in the displayed image at which the gaze point of the user is directed. In one aspect, the control unit is configured to control at least one function of the teleoperational medical system based upon the determined viewing location.

In another exemplary aspect, the present disclosure is directed to a method for operating a teleoperational medical system. In one aspect, the method comprises displaying an image, including a surgical field image, on an image display. In one aspect, the method comprises measuring the gaze point of a user in the image display. In one aspect, the method comprises determining a viewing location in the displayed image at which the gaze point of the user is directed. In one aspect, the method comprises controlling at least one function of the teleoperational medical system based upon the determined viewing location.

In another exemplary aspect, the present disclosure is directed to a teleoperational medical system comprising a first eye tracking unit and a second eye tracking unit. In one aspect, the first eye tracking unit includes one or more first image displays, one or more first eye trackers, and a first processor coupled to the one or more first eye trackers and configured to calculate a first gaze point of a first user when the first user looks at a first image displayed by the one or more first image displays. In one aspect, the second eye tracking unit includes one or more second image displays, one or more second eye trackers, and a second processor coupled to the one or more second eye trackers and configured to calculate a second gaze point of a second user when the second user looks at a second image displayed by the one or more second image displays. In one aspect, the one or more first image displays are coupled to the second processor. In one aspect, the one or more second image displays are coupled to the first processor.

In another exemplary aspect, the present disclosure is directed to a method for operating a teleoperational medical system. In one aspect, the method comprises tracking eye gaze dynamics in a 3D image display of a surgical site. In one aspect, the method comprises determining a condition of a user when the user looks at the 3D image display.

In another exemplary aspect, the present disclosure is directed to a method for operating a surgical system. In one aspect, the method comprises determining a 3D gaze point for a first user viewing a 3D image in a first display and displaying the 3D gaze point in the 3D image in a second display. In one aspect, the method comprises receiving an instruction from a second user viewing the 3D gaze point of the first user on the second display.

In another exemplary aspect, the present disclosure is directed to a method for operating a surgical system comprising an instrument and a 3D display. In one aspect, the method comprises displaying a 3D image on the 3D display and determining a location of a 3D gaze point for a user viewing the 3D image. In one aspect, the method comprises comparing the 3D image and the location of the 3D gaze point.

These and other embodiments are further discussed below with respect to the following figures.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 1B illustrates a front elevation view of an exemplary teleoperational assembly according to one embodiment of the present disclosure. FIG. 1C illustrates a front elevation view of an exemplary operator input system according to one embodiment of the present disclosure.

FIG. 1D illustrates a front view of an exemplary vision cart component according to one embodiment of the present disclosure.

FIG. 2C is a flowchart illustrating an exemplary method of using the eye tracking units to control and affect the teleoperational medical system and/or a surgical instrument according to one embodiment of the present disclosure.

FIG. 5 is an example of a 3D image display of the surgeon's console showing a 3D image of a surgical site with a 3D coordinate system according to one embodiment of the present disclosure.

FIGS. 6A-6B illustrate various embodiments of an endoscope that can be used in the teleoperational medical system of FIGS. 1A-1C according to the present disclosure.

DETAILED DESCRIPTION

Figure 1A:
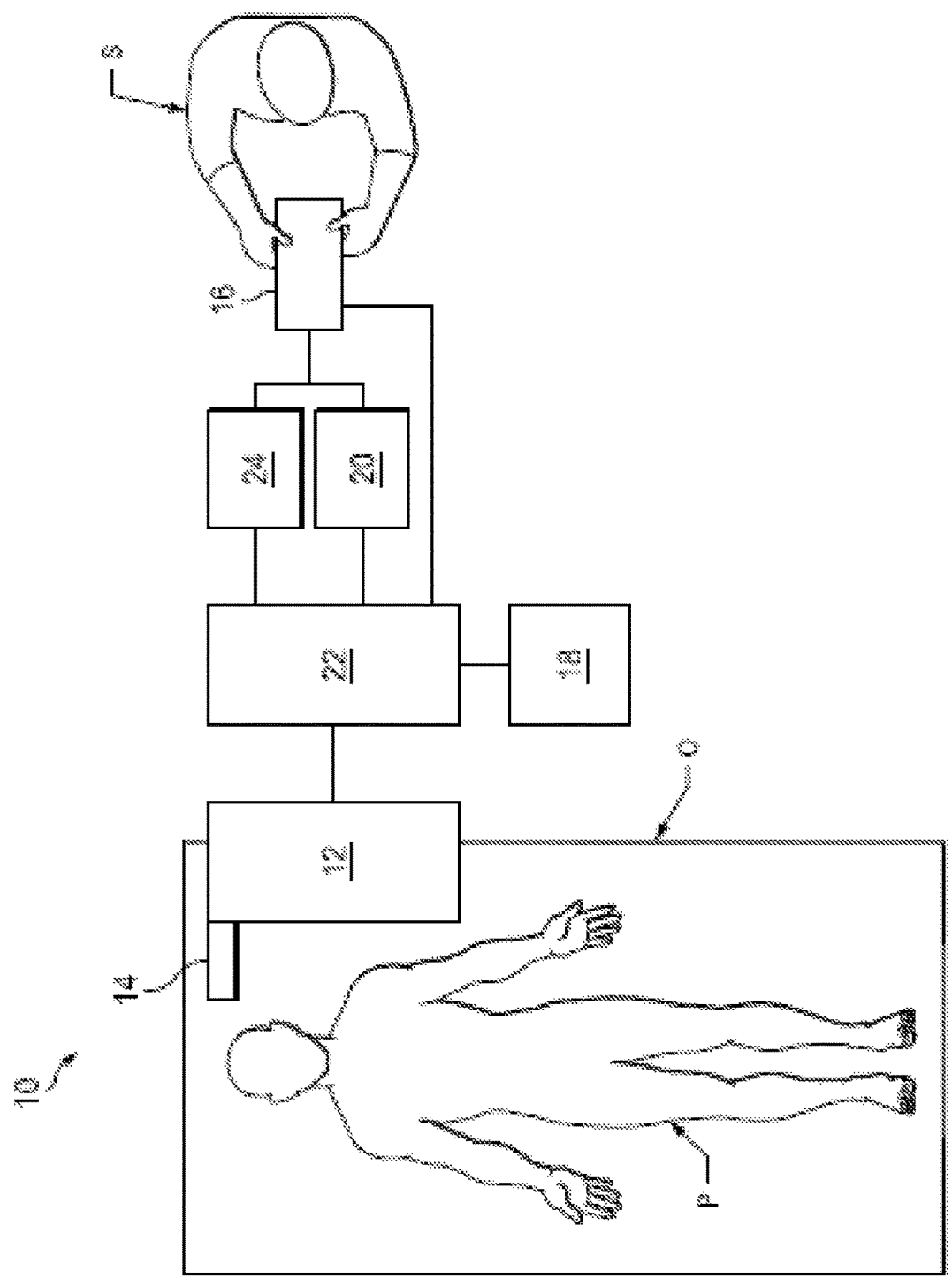
FIG. 1A illustrates an exemplary teleoperational medical system according to one embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the disclosure.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. The numerous iterations of these combinations will not be described separately. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For simplicity, in some instances the same reference numbers are used throughout the drawings to refer to the same or like parts.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an elongated object.

It will be appreciated that the terms "proximal" and "distal" are used herein with reference to a clinician manipulating an end of an instrument extending from the clinician to a surgical site. The term "proximal" refers to the portion of the instrument closer to the clinician, and the term "distal" refers to the portion of the instrument further away from the clinician and closer to the surgical site. For conciseness and clarity, spatial terms such as "horizontal," "vertical," "above," and "below" may be used herein with respect to the drawings. However, surgical instruments are used in many orientations and positions, and there terms are not intended to be limiting and absolute.

The present disclosure relates generally to using eye tracking systems to observe and measure characteristics of a user's eyes (e.g., eye gaze tracking) during the use of teleoperational medical systems and/or instruments used in a variety of medical procedures, including without limitation diagnostic, surgical, and/or therapeutic procedures. In particular, in some embodiments, the eye tracking systems disclosed herein rely on the ability to track the accurate location (e.g., 2D or 3D location) of the user's eye gaze on a surgical console, display system, or other medical or surgical system component. In some embodiments, the eye tracking systems may be used to control the teleoperational system by directly operating the system instruments and/or by influencing system characteristics to effect system-wide changes. In particular, some embodiments of the present disclosure are related to system and instrument control, and in particular to system and instrument control by tracking the operator's eye gaze while the operator uses a teleoperational medical system during a minimally invasive procedure. In some embodiments, multiple eye tracking systems (e.g., for the trainer/proctor as well as the student) may be used together to enable proctoring and training through a given procedure. In some embodiments, the eye tracking systems may be used to obtain performance metrics or assess user skill in operating the teleoperational system during a given procedure. In particular, in some embodiments, the eye tracking system incorporated into a teleoperational medical system may track the eye gaze of a surgeon to evaluate a surgeon's skill level, consistency, physical state, and/or any other performance measure during a surgery. Those of skill in the art will realize that the eye tracking systems disclosed herein may be utilized in similar (e.g., non-teleoperational) implementations benefiting from system/instrument control, training/proctoring, and/or performance evaluation. By utilizing the eye tracking systems and methods disclosed herein, a user may experience more intuitive and more efficient interaction with a teleoperational medical system.

According to various embodiments, minimally invasive medical procedures may be performed using a teleoperational system to guide instrument delivery and operation. Referring to FIG. 1A of the drawings, a teleoperational medical system for use in, for example, medical procedures including diagnostic, therapeutic, or surgical procedures, is generally indicated by the reference numeral 10. As will be described, the teleoperational medical systems of this disclosure are under the teleoperational control of a surgeon. In alternative embodiments, a teleoperational medical system may be under the partial control of a computer programmed to perform the procedure or sub-procedure. In still other alternative embodiments, a fully automated medical system, under the full control of a computer programmed to perform the procedure or sub-procedure, may be used to perform procedures or sub-procedures. As shown in FIG. 1, the teleoperational medical system 10 generally includes a teleoperational assembly 12 near or mounted to an operating table O on which a patient P is positioned. The teleoperational assembly 12 may be referred to as a patient-side manipulator (PSM). A medical instrument system 14 is operably coupled to the teleoperational assembly 12. An operator input system 16 allows a surgeon or other type of clinician S to view images of or representing the surgical site and to control the operation of the medical instrument system 14. The operator input system 16 may be referred to as a master or surgeon's console. One example of a teleoperational surgical system that can be used to implement the systems and techniques described in this disclosure is a da Vinci® Surgical System manufactured by Intuitive Surgical, Inc. of Sunnyvale, Calif.

The teleoperational assembly 12 supports the medical instrument system 14 and may include a kinematic structure of one or more non-servo controlled links (e.g., one or more links that may be manually positioned and locked in place, generally referred to as a set-up structure) and a teleoperational manipulator. (See, e.g., FIG. 2) The teleoperational assembly 12 includes plurality of motors that drive inputs on the medical instrument system 14. These motors move in response to commands from a control system 22. The motors include drive systems which when coupled to the medical instrument system 14 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument.

The teleoperational medical system 10 also includes an image capture system 18 which includes an image capture device, such as an endoscope, and related image processing hardware and software. The teleoperational medical system 10 also includes a control system 22 that is operatively linked to sensors, motors, actuators, and other components of the teleoperational assembly 12, the operator input system 16 and to the image capture system 18.

The operator input system 16 may be located at a surgeon's console, which is usually located in the same room as operating table O. It should be understood, however, that the surgeon S can be located in a different room or a completely different building from the patient P. Operator input system 16 generally includes one or more control device(s) for controlling the medical instrument system 14. More specifically, in response to the surgeon's input commands, the control system 22 effects servomechanical movement medical instrument system 14. The control device(s) may include one or more of any number of a variety of input devices, such as hand grips, joysticks, trackballs, data gloves, trigger-guns, hand-operated controllers, foot-operated controllers, voice recognition devices, touch screens, body motion or presence sensors, and the like. In some embodiments, the control device(s) will be provided with the same degrees of freedom as the medical instruments of the teleoperational assembly to provide the surgeon with telepresence, the perception that the control device(s) are integral with the instruments so that the surgeon has a strong sense of directly controlling instruments as if present at the surgical site. In other embodiments, the control device(s) may have more or fewer degrees of freedom than the associated medical instruments and still provide the surgeon with telepresence. In some embodiments, the control device(s) are manual input devices which move with six degrees of freedom, and which may also include an actuatable handle for actuating instruments (for example, for closing grasping jaws, applying an electrical potential to an electrode, delivering a medicinal treatment, and the like).

The system operator sees images, captured by the image capture system 18, presented for viewing on a display system 20 operatively coupled to or incorporated into the operator input system 16. The display system 20 displays an image or representation of the surgical site and medical instrument system(s) 14 as generated by sub-systems of the image capture system 18. The display system 20 and the operator input system 16 may be oriented so the operator can control the medical instrument system 14 and the operator input system 16 with the perception of telepresence. The display system 20 may include multiple displays such as separate right and left displays for presenting separate images to each eye of the operator, thus allowing the operator to view stereo images.

Alternatively or additionally, display system 20 may present images of the surgical site recorded and/or imaged preoperatively or intra-operatively using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and the like. The presented preoperative or intra-operative images may include two-dimensional, three-dimensional, or four-dimensional (including e.g., time based or velocity based information) images and associated image data sets for reproducing the images.

The control system 22 includes at least one memory and at least one processor (not shown), and typically a plurality of processors, for effecting control between the teleoperational system 12, medical instrument system 14, the operator input system 16, the image capture system 18, and the display system 20. The control system 22 also includes programmed instructions (e.g., a computer-readable medium storing the instructions) to implement some or all of the methods described in accordance with aspects disclosed herein. While control system 22 is shown as a single block in the simplified schematic of FIG. 1, the system may include two or more data processing circuits with one portion of the processing optionally being performed on or adjacent the teleoperational assembly 12, another portion of the processing being performed at the operator input system 16, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 22 supports wireless communication protocols such as Bluetooth, IrDA, HomeRF, IEEE 802.11, DECT, and Wireless Telemetry.

In some embodiments, control system 22 may include one or more servo controllers that receive force and/or torque feedback from the medical instrument system 104. Responsive to the feedback, the servo controllers transmit signals to the operator input system 16. The servo controller(s) may also transmit signals instructing teleoperational assembly 12 to move the medical instrument system(s) 14 which extend into an internal surgical site within the patient body via openings in the body. Any suitable conventional or specialized servo controller may be used. A servo controller may be separate from, or integrated with, teleoperational assembly 12. In some embodiments, the servo controller and teleoperational assembly are provided as part of a teleoperational arm cart positioned adjacent to the patient's body.

In this embodiment, the teleoperational medical system 10 also includes an eye tracking unit 24 which may be operatively coupled to or incorporated into the operator input system 16. The eye tracking unit 24 is operatively coupled to the control system 22 for sensing, measuring, recording, and conveying information related to the operator's eyes while the operator is viewing the display 20 and/or operating the operator controls at the operator input system 16.

The teleoperational medical system 10 may further include optional operation and support systems (not shown) such as illumination systems, steering control systems, fluid management systems such as irrigation systems and/or suction systems. In alternative embodiments, the teleoperational system may include more than one teleoperational assembly and/or more than one operator input system. The exact number of manipulator assemblies will depend on the surgical procedure and the space constraints within the operating room, among other factors. The operator input systems may be collocated or they may be positioned in separate locations. Multiple operator input systems allow more than one operator to control one or more manipulator assemblies in various combinations.

Figure 1B:
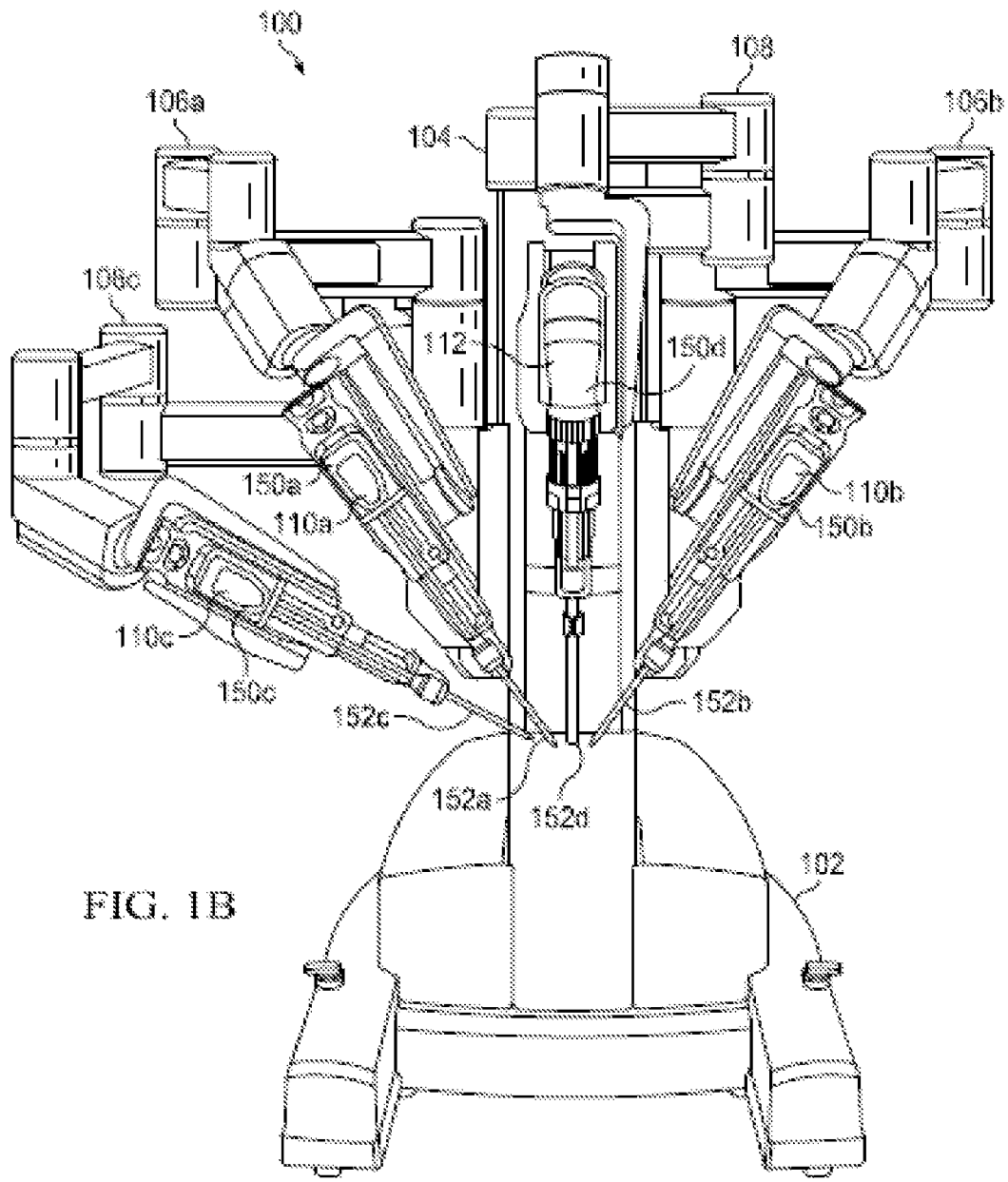
FIGS. 1B, 1C, and 1D illustrate exemplary components of a teleoperational medical system according to various embodiments of the present disclosure. In particular.

FIG. 1B is a front elevation view of a teleoperational assembly 100 (e.g., the teleoperational assembly 12 shown in FIG. 1A) according to one embodiment. The assembly 100 includes a base 102 that rests on the floor, a support tower 104 that is mounted on the base 102, and several arms that support surgical tools (including portions of the image capture system 18). As shown in FIG. 1B, arms 106a, 106b, 106c are instrument arms that support and move the surgical instruments used to manipulate tissue, and arm 108 is a camera arm that supports and moves the endoscope. FIG. 1B further shows interchangeable surgical instruments 110a, 110b, 110c mounted on the instrument arms 106a, 106b, 106c, respectively, and it shows an endoscope 112 mounted on the camera arm 108. The endoscope 112 may be a stereo endoscope for capturing stereo images of the surgical site and providing the separate stereo images to the display system 20. Knowledgeable persons will appreciate that the arms that support the instruments and the camera may also be supported by a base platform (fixed or moveable) mounted to a ceiling or wall, or in some instances to another piece of equipment in the operating room (e.g., the operating table). Likewise, they will appreciate that two or more separate bases may be used (e.g., one base supporting each arm).

Figure 1C:
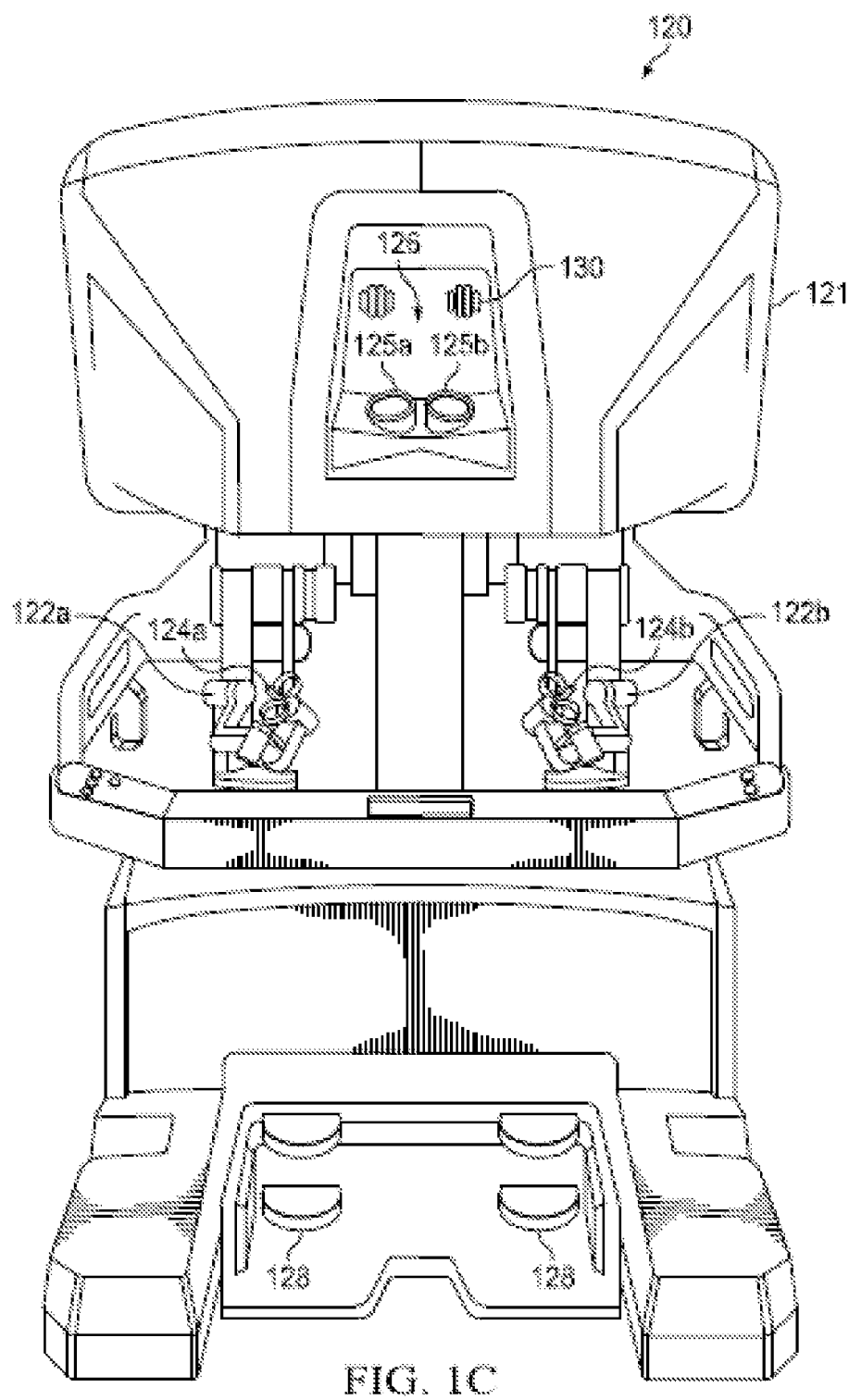

As is further illustrated in FIG. 1B, the instruments 110a, 110b, 110c, and the endoscope 112 include instrument interfaces 150a, 150b, 150c, and 150d, respectively, and instrument shafts 152a, 152b, 152c, and 152d, respectively. In some embodiments, the teleoperational assembly 100 may include supports for cannulas that fix the instruments 110a, 110b, 110c, and the endoscope 112 with respect to the cannulas. In some embodiments, portions of each of the instrument arms 106a, 106b, 106c, and 108 may be adjustable by personnel in the operating room in order to position the instruments 110a, 110b, 110c, and the endoscope 112 with respect to a patient. Other portions of the arms 106a, 106b, 106c, and 108 may be actuated and controlled by the operator at an operator input system 120 (as shown in FIG. 1C). The surgical instruments 110a, 110b, 110c, and endoscope 112, may also be controlled by the operator at the operator input system 120.

FIG. 1C is a front elevation view of an operator input system 120 (e.g., the operator input system 16 shown in FIG. 1A). The operator input system 120 includes a console 121 equipped with left and right multiple degree-of-freedom (DOF) control interfaces 122a and 122b, which are kinematic chains that are used to control the surgical instruments 110a, 110b, 110c, and the endoscope 112. The surgeon grasps a pincher assembly 124a, 124b on each of control interfaces 122, typically with the thumb and forefinger, and can move the pincher assembly to various positions and orientations. When a tool control mode is selected, each of control interfaces 122 is configured to control a corresponding surgical instrument and instrument arm 106. For example, a left control interface 122a may be coupled to control the instrument arm 106a and the surgical instrument 110a, and a right control interface 122b may be coupled to the control instrument arm 106b and the surgical instrument 110b. If the third instrument arm 106c is used during a surgical procedure and is positioned on the left side, then left control interface 122a can be switched from controlling the arm 106a and the surgical instrument 110a to controlling the arm 106c and the surgical instrument 110c. Likewise, if the third instrument arm 106c is used during a surgical procedure and is positioned on the right side, then the right control interface 122a can be switched from controlling the arm 106b and surgical instrument 110b to controlling the arm 106c and the surgical instrument 110c. In some instances, control assignments between the control interfaces 122a, 122b and combination of arm 106a/surgical instrument 110a and combination of arm 106b/surgical instrument 110b may also be exchanged. This may be done, for example, if the endoscope is rolled 180 degrees, so that the instrument moving in the endoscope's field of view appears to be on the same side as the control interface the surgeon is moving. The pincher assembly is typically used to operate a jawed surgical end effector (e.g., scissors, grasping retractor, and the like) at the distal end of a surgical instrument 110.

Additional controls are provided with foot pedals 128. Each of foot pedals 128 can activate certain functionality on the selected one of instruments 110. For example, foot pedals 128 can activate a drill or a cautery tool or may operate irrigation, suction, or other functions. Multiple instruments can be activated by depressing multiple ones of pedals 128. Certain functionality of instruments 110 may be activated by other controls.

The surgeon's console 120 also includes a stereo image viewer system 126 (e.g., the display system 20 shown in FIG. 1A). Stereo image viewer system 126 includes a left eyepiece 125a and a right eyepiece 125b, so that the surgeon may view left and right stereo images using the surgeon's left and right eyes respectively inside the stereo image viewer system 126. Left side and right side images captured by endoscope 112 are outputted on corresponding left and right image displays, which the surgeon perceives as a three-dimensional image on a display system (e.g., the display system 20 shown in FIG. 1A. In an advantageous configuration, the control interfaces 122 are positioned below stereo image viewer system 126 so that the images of the surgical tools shown in the display appear to be located near the surgeon's hands below the display. This feature allows the surgeon to intuitively control the various surgical instruments in the three-dimensional display as if watching the hands directly. Accordingly, the servo control of the associated instrument arm and instrument is based on the endoscopic image reference frame.

The endoscopic image reference frame is also used if the control interfaces 122 are switched to a camera control mode. In some cases, if the camera control mode is selected, the surgeon may move the distal end of endoscope 112 by moving one or both of the control interfaces 122 together. The surgeon may then intuitively move (e.g., pan, tilt, zoom) the displayed stereoscopic image by moving the control interfaces 122 as if holding the image in his or her hands.

As is further shown in FIG. 1C, a headrest 130 is positioned above stereo image viewer system 126. As the surgeon is looking through stereo image viewer system 126, the surgeon's forehead is positioned against headrest 130. In some embodiments of the present disclosure, manipulation of endoscope 112 or other surgical instruments can be achieved through manipulation of headrest 130 instead of utilization of the control interfaces 122. In some embodiments, the headrest 130 can, for example, include pressure sensors, a rocker plate, optically monitored slip plate, or other sensors that can detect movement of the surgeon's head. Additional details on using a sensing method to manipulate the headrest in order to control the endoscope camera may be found, for example, in U.S. Application No. 61/865,996, entitled "ENDOSCOPE CONTROL SYSTEM," which is incorporated herein by reference.

Figure 1D:
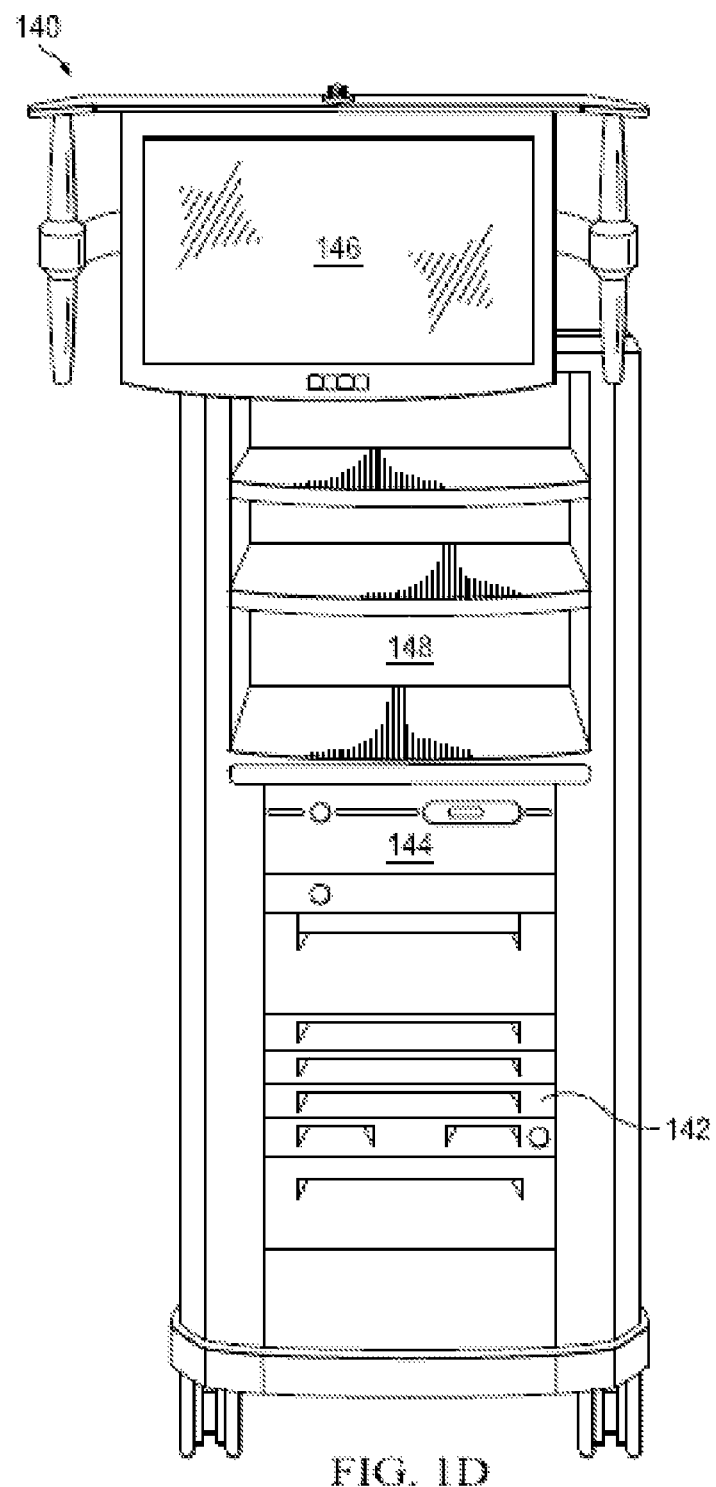

FIG. 1D is a front view of a vision cart component 140 of a surgical system. For example, in one embodiment, the vision cart component 140 is part of the medical system 10 shown in FIG. 1A. The vision cart 140 can house the surgical system's central electronic data processing unit 142 (e.g., all or portions of control system 22 shown in FIG. 1A) and vision equipment 144 (e.g., portions of the image capture system 18 shown in FIG. 1A). The central electronic data processing unit 142 includes much of the data processing used to operate the surgical system. In various implementations, however, the electronic data processing may be distributed in the surgeon console 120 and teleoperational assembly 100. The vision equipment 144 may include camera control units for the left and right image capture functions of the endoscope 112. The vision equipment 144 may also include illumination equipment (e.g., a Xenon lamp) that provides illumination for imaging the surgical site. As shown in FIG. 1D, the vision cart 140 includes an optional touch screen monitor 146 (for example a 24-inch monitor), which may be mounted elsewhere, such as on the assembly 100 or on a patient side cart. The vision cart 140 further includes space 148 for optional auxiliary surgical equipment, such as electrosurgical units, insufflators, suction irrigation instruments, or third-party cautery equipment. The teleoperational assembly 100 and the surgeon's console 120 are coupled, for example via optical fiber communications links, to the vision cart 140 so that the three components together act as a single teleoperated minimally invasive surgical system that provides an intuitive telepresence for the surgeon.

Note that in some embodiments, some or all of the assembly 100 of the teleoperated surgical system can be implemented in a virtual (simulated) environment, wherein some or all of the image seen by the surgeon at the surgeon's console 120 can be synthetic images of instruments and/or anatomy. In some embodiments, such synthetic imagery can be provided by the vision cart component 140 and/or directly generated at the surgeon's console 120 (e.g., via a simulation module).

During a typical minimally invasive surgical procedure with the teleoperated surgical system described with reference to FIGS. 1A-1D, at least two incisions are made into the patient's body (usually with the use of a trocar to place the associated cannula). One incision is for the endoscope camera instrument, and the other incisions are for the surgical instruments. In some surgical procedures, several instrument and/or camera ports are used to provide access and imaging for a surgical site. Although the incisions are relatively small in comparison to larger incisions used for traditional open surgery, a minimum number of incisions is desired to further reduce patient trauma and for improved cosmesis. In other embodiments, the teleoperational medical system 10 may be used with single incision access to the patient anatomy or with access through natural orifices such as the nose, mouth, anus, vagina, etc.

During a typical teleoperated surgery, it is often necessary for a surgeon to physically manipulate various controls to control the surgical system, the imaging devices, and/or the other surgical instruments associated with the system. For example, a surgeon may need to adjust the field of view of the imaging device by physically manipulating controls to guide and influence the device. The surgeon may use his or her hand to manually control a joystick or mouse, or his or her foot to tap a foot pedal at the surgeon's console to log-in to the surgical system, to search for a target surgical site within the view of the endoscope, to operate the movement of a surgical instrument such as a clamp, and/or to adjust the system settings or display settings. The conventional methods require the surgeon to free one hand from surgical operation, or to use one foot to tap the foot pedal, both of which may unnecessarily delay or disrupt the surgical operation. For example, the hand or foot action may redirect the surgeon's gaze and attention from the target surgical site to the surgeon's console, which could delay or disrupt the operation. After performing the required manual adjustment, the surgeon may need to spend additional time refocusing his or her attention and gaze point on the target surgical site.

Embodiments disclosed herein utilize gaze detection to enhance the way one or more users (e.g., surgeons and/or trainers) interface with the surgical system. By translating the user's eye gaze (e.g., the 3D location of a user's eye gaze relative to a surgical console, display system, or other medical or surgical system component) into commands directed to the surgical system, embodiments disclosed herein may enable faster and more efficient control over the teleoperational medical system 10 than provided by conventional control methods. Eye tracking, or eye-gaze tracking, is the process of measuring either point-of-gaze (POG) (i.e., where the user is looking, typically in 3D space), or the motion of an eye relative to a head. In other words, POG is the point in space where a person's gaze is directed to, and has also been defined as the point in space that is imaged on the center of the highest acuity region of the retina (i.e., the fovea) of each eye.

Figure 2A:
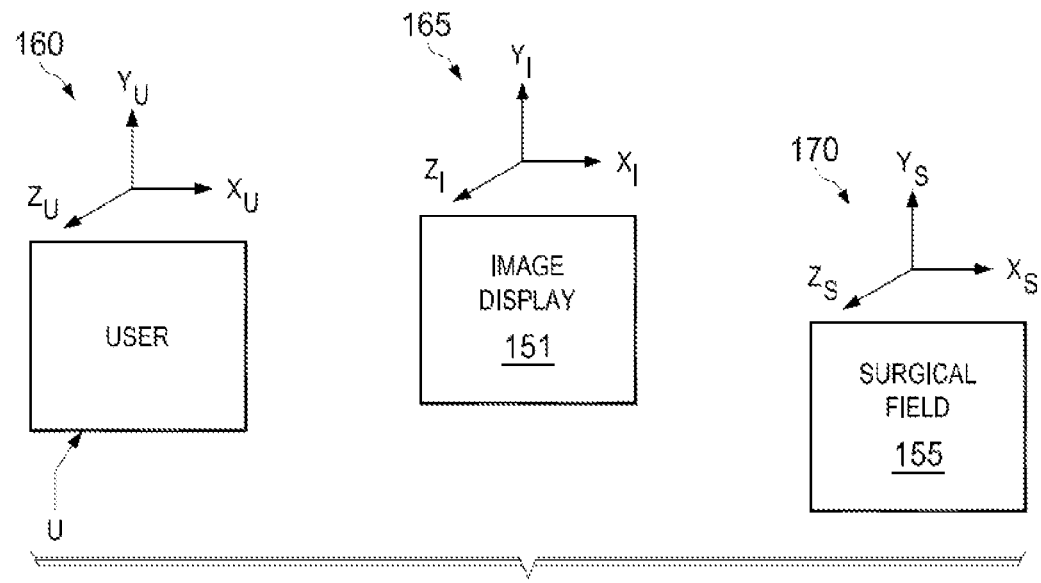
FIG. 2A illustrates a block diagram of the 3D coordinate frames of a user relative to an exemplary image display and a surgical field according to one embodiment of the present disclosure.

FIG. 2A schematically illustrates a user U (e.g., the surgeon S or a proctor) relative to an image display 151 (e.g., the image display system 20 shown in FIG. 1A) and a surgical field 155 (e.g., an area of the interior anatomy of patient P). The user (and his or her eyes) exists in a user 3D Cartesian coordinate reference system 160 (i.e., a user frame). For ease of understanding and economy of words, the term "Cartesian coordinate reference system" will simply be referred to as "frame" in the rest of this specification. The image display 151 exists in a two-dimensional or three-dimensional image frame 165, and the surgical field exists in a surgical frame 170. Each frame 160, 165, 170 includes different dimensions and properties from the others. As the user shifts his or her gaze in the first frame 160 relative to the image display 165 in the second frame 165, the embodiments disclosed herein can translate that eye motion into a control signal to correspondingly influence the teleoperational medical system 10 including a surgical instrument visible in the frame 165 of the display and existing in the frame 170 of the surgical field.

In one aspect, the eye-gaze tracking and observation of other eye characteristics can be used to communicate with and/or influence the behavior of the teleoperational medical system 10 as a whole. For example, the eye characteristics and dynamics observed by the eye tracking unit 24 shown in FIG. 1A may be used for surgeon recognition and log-in (e.g., in a manner similar to retinal scans). This feature is described in further detail below with respect to FIGS. 4A and 4B. In some instances, the eye gaze of the user can be used to calibrate the 3D positions of surgical instruments in the surgical field frame 170 and account for the possible inaccuracies of the telerobotic arm kinematic chain. In some instances, the teleoperational medical system 10 can be configured to prevent movement of the surgical instruments in the surgical frame 170 (i.e., lock out the user) if the user's gaze is not directed towards the image display frame 165 or to a specific viewing location within the frame 165. In some instances, the teleoperational medical system 10 can be configured to prevent movement of the surgical instruments in the surgical frame 170 (i.e., lock out the user) if the user's eyes are not detected by the eye trackers. In some embodiments, a user interface (e.g., a menu) may be overlaid upon the image of the surgical field shown on the image display. The eye gaze of the user in the user frame 160 may be used to determine a viewing location in the image displayed on the image display 151 in the image frame 165, and can identify a user's selection among user selectable options of the user interface corresponding to the determined viewing location. In some instances, the 3D position of the user's gaze relative to the image frame 165 of the image display may determine the depth, position, and size of the displayed user interface on the image display 151. For example, the user interface may be automatically displayed at a depth, position, and size that best corresponds to the current 3D position of the user's gaze, thereby minimizing the need for the user to refocus his or her eyes to interact with the user interface. In some instances, the 3D position of the user's gaze may be used to quantify if the user is seeing stereo or not based on the observed dynamics between the two eyes. In some instances, the 3D position of the user's gaze may be used to adjust the ergonomic settings (e.g. height, orientation, etc.) of the stereo viewer so that the user can see the entire display (and vice versa the user's gaze can be determined across the entire screen) or to center the user's gaze in the middle of the screen.

In another aspect, real-time eye-gaze tracking can be used to activate, deactivate, and otherwise control distinct surgical instruments in the surgical frame 170 that are coupled to the teleoperational medical system 10 such as, by way of non-limiting example, imaging devices and/or energy delivery devices. For example, the system 10 may be configured to activate a surgical instrument if the processor determines that the viewing location relative to the image on the image display matches the position of the surgical instrument for a predetermined length of time. In one embodiment, gaze detection can be used to define where the user wants to guide the imaging device to define the field of view. The embodiments disclosed herein may be configured to automatically move the imaging device in the direction of the user's eye gaze to continuously keep the user's desired field of view (e.g., a target surgical site) on the display without the user having to manually change the position or viewing angle of the imaging device. For example, in some embodiments, the user's eye gaze can be used to automatically center the view of the imaging device to correspond to the direction of the user's eye gaze. In some embodiments, the user's eye gaze may be used to switch an instrument from one modality to another. For example, in one instance, the user's eye gaze may be interpreted to change the operating mode of an imaging device (e.g., switching between imaging modes such as color imaging, black and white imaging, fluorescence imaging, ultrasonic imaging, and/or any other imaging modalities). Similarly, in another instance, the user may execute a particular pattern of blinking or other eye movements to change the operating mode of an imaging device (e.g., switching between imaging modes such as color imaging, black and white imaging, fluorescence imaging, ultrasonic imaging, and/or any other imaging modalities).

In another instance, gaze detection may assist the user in applying a label to or otherwise marking the real-time displayed image of the surgical field. A surgeon may look at a 3D location in the surgical field and confirm with a secondary action (e.g., by way of non-limiting example, by pushing a separate button, maintaining an extended gaze, or blinking in a particular pattern) to apply a virtual label in the surgical field and/or on the displayed image 150 to identify an anatomical area of interest.

In another instance, a particular surgical instrument may only be activated when the eye tracking unit confirms that the surgeon's eye gaze is focused on that particular instrument for a predetermined length of time. For example, the teleoperational medical system 10 may be configured to require that the surgeon's eye gaze be focused on a stapler instrument for a specified period of time before the stapler instrument is permitted to deliver staples. This facilitates the intentional activation of instruments within the surgeon's field of view, and may prevent the inadvertent activation of an instrument that was out of the field of view and/or was not being attended to. When the surgeon's eye gaze has been directed elsewhere for a specified period of time, the surgical instrument may be deactivated. In another embodiment, the control over a particular surgical instrument may be transferred from a first user to a second user when the eye tracking unit confirms that the second user's eye gaze is focused on that particular instrument for a predetermined length of time or is focused on that particular instrument in a certain fashion. Some of these embodiments are described further below with reference to FIG. 3C.

In another aspect, real-time eye-gaze tracking can be used to facilitate the training or proctoring of a surgeon during a procedure. In one instance, as shown in FIG. 2D, the teleoperational medical system 10 may include separate surgical consoles and separate sets of eye tracking units for the surgeon and the proctor, with each set of eye tracking units being configured to recognize and convey the eye gaze movements of either the surgeon or the proctor to affect the operation of the teleoperational medical system 10 and/or the surgical instruments. Exemplary methods of proctoring or training are described below with reference to FIGS. 3A and 3B. The 3D position of the surgeon's eye gaze may be displayed on an external 3D image display for a proctor (e.g., a proctoring surgeon) to see and evaluate in order to provide feedback and guidance in real-time. Similarly, the 3D position of the proctor's eye gaze may be displayed on the external 3D image display on the surgical console for the surgeon to see and be guided by in real-time. For example, during operation of the teleoperational medical system 10 (e.g., during training or during actual surgery), it can be desirable to ensure that the surgeon is focusing on the correct portion of the surgical site. By viewing the 3D position of the proctor's gaze on the image display within the surgical console, the surgeon may know where to look within the surgical field (e.g., by seeing where the proctor is looking within the surgical field). In some instances, the eye gaze of the proctor can be captured from an image display on a variety of possible devices, including by way of non-limiting example, the vision cart 140, the surgical console 120, a dual or shared console, a touchscreen display, and/or a remote device such as a tablet device.

In some instances, the surgeon's image display may be altered in real-time to reflect the 3D position of the proctor's gaze. In one embodiment, when the system 10 detects that the proctor is looking at a particular area of his or her image display corresponding to a particular 3D position within the surgical frame 170, the system 10 may highlight or otherwise indicate the corresponding area of the surgeon's image display (e.g., the area on the surgeon's image display corresponding to the same 3D position within the surgical frame 170). For example, the surgeon's image display 151 may sharpen (e.g., increase resolution) or become brighter in the areas of the image display corresponding to the 3D position of the proctor's gaze. In additional or alternative embodiments, the surgeon's image display may dim or become fuzzier in the areas of the image display corresponding to the 3D positions where the proctor's gaze is not directed.

In another aspect, real-time eye-gaze tracking can be used to evaluate and grade the performance of a surgeon during and/or after a procedure. The eye gaze tracking embodiments disclosed herein can be used to measure and quantify the skill level of a surgeon operating the teleoperational medical system 10 based on various eye characteristics, including, without limitation, eye gaze fixations, saccade, and/or which region of the screen the eye gaze occupies. In addition, tracking a surgeon's eye gaze dynamics and/or pupil diameter fluctuations in real time can be used to monitor the condition (e.g., the stress level and/or workload) of the surgeon. In some embodiments, the system 10 can be configured to provide a warning if a drop in that condition is determined based on detected changes or patterns of eye gaze. This feature is described in further detail below with respect to FIGS. 4A and 4B.

Figure 2B:
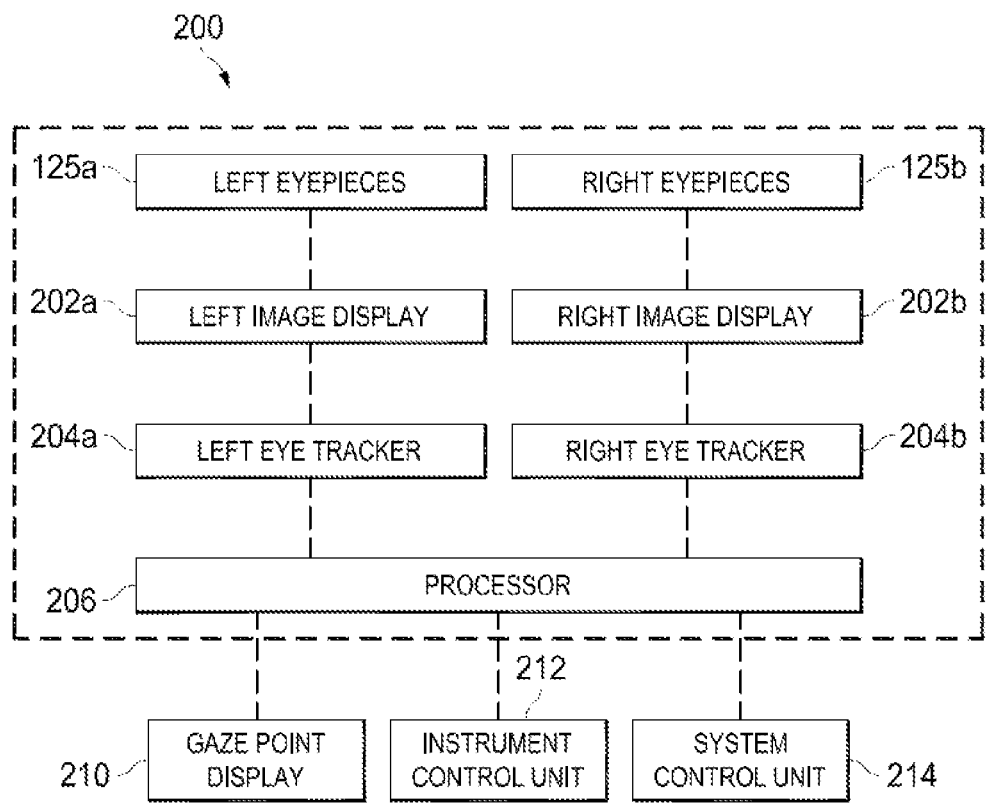
FIG. 2B illustrates an exemplary eye tracking unit used by the teleoperational medical system of FIGS. 1A, 1B, and 1C according to one embodiment of the present disclosure.
Figure 2D:
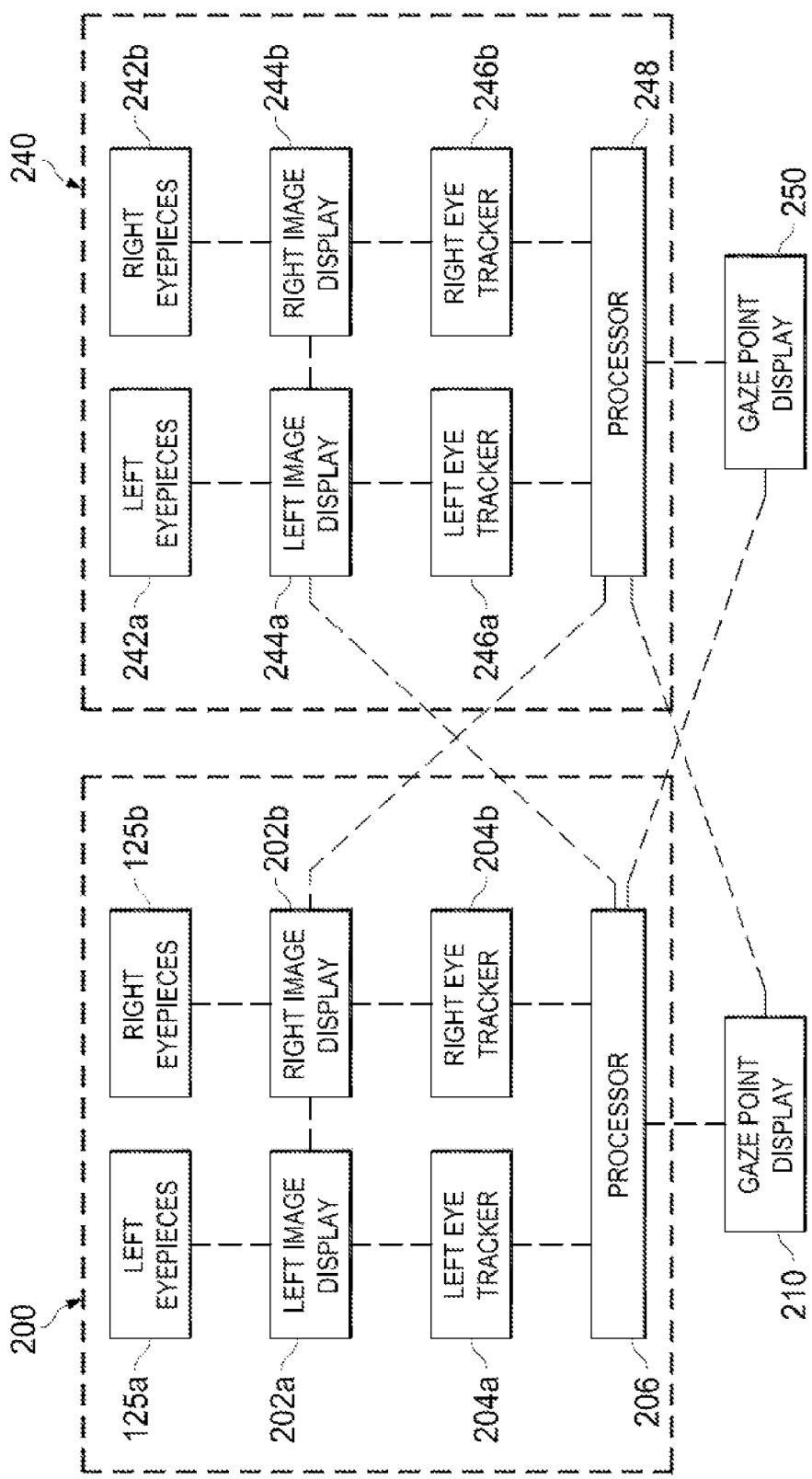
FIG. 2D illustrates an exemplary proctor's eye tracking unit coupled to an exemplary eye tracking unit of a surgeon being trained according to one embodiment of the present disclosure.

FIG. 2B is a diagram illustrating some examples of an eye tracking unit 200 that may be used by the teleoperational medical system 10 of FIGS. 1A, 1B, and 1C according to some embodiments of the present disclosure. As mentioned above, eye-gaze tracking, or eye tracking, is the process of measuring either the POG (e.g., "where a user is looking") or the motion of the eye relative to the head. Thus, the eye tracking unit 200 comprises a device for measuring eye characteristics of the user such as eye position and eye movement. There are a number of methods for measuring eye movement and gaze direction. Some methods use video images from which the eye position is extracted, and other methods use search coils or are based on electrooculograms. In yet another method, infrared light is emitted by a device either having or in communication with an infrared camera or detector. The infrared light is reflected from the user's retinas back onto the infrared camera or detector, and the amount of reflected infrared light is based on the direction of the person's gaze relative to the emitter. The user's gaze point in 3D space may be determined once the reflected infrared light reaches a particular threshold for a certain amount of time. Small lapses in gaze can be interpreted as blinks and are typically ignored.

In the pictured embodiment, the eye tracking unit 200 includes left and right eyepieces 125a and 125b, left and right image displays 202a and 202b, left and right eye trackers 204a and 204b, and a processor 206. In other embodiments, the eye tracking unit 200 may include a single eye tracker that is configured to simultaneously track both the left and right eye (e.g., even though the left and right eyes have independent image displays 202a, 202b). In some embodiments, eye tracking unit 200 further includes reflecting system and/or light emitters to illuminate the surgeon's eyes for the eye trackers to track a gaze point. In some embodiments, the reflecting system may include a plurality of mirrors arranged to reflect the light from the light emitter into the surgeon's eyes, and to reflect the gaze point of the surgeon's eyes into the eye tracker. Additional details on various embodiments of stereo viewer 126 may be found, for example, in U.S. Provisional Application No. 61/955,334 filed Mar. 19, 2014 entitled "MEDICAL DEVICES, SYSTEMS, AND METHODS INTEGRATING EYE GAZE TRACKING FOR STEREO VIEWER," which is incorporated herein by reference in its entirety.

In some embodiments, the endoscope 112 located at the teleoperational assembly 100 can be manipulated to capture images of a surgical field during a surgery, and theses images are shown on the left and right image displays 202a and 202b. The images captured by the endoscope 112 may then be processed by the processor 206 to generate left and right stereo images. In some embodiments, the processor 206 may be located at vision cart 140, for example, as part of the central electronic data processing unit 142. Alternatively, the processor 206 may be located at the teleoperational assembly 100 and/or the surgeon's console 120. In some embodiments, eye tracking unit 200 may also be used in a surgeon's console integrated with a simulation module, e.g., a da Vinci® Skills Simulator™, where virtual images can be shown on the left and right image displays 202a and 202b.

Referring to FIG. 2B, the generated left and right stereo images may be shown on left and right image displays 202a and 202b, respectively. The left and right eyepieces 125a and 125b include lenses, and the surgeon may view the left and right image displays 202a and 202b through the left and right eyepieces 125a and 125b with the surgeon's left and right eyes respectively. A 3D stereo image of the surgical field may be perceived by the surgeon via the eye tracking unit 200. In some embodiments, the distance between the left and right eye pieces 125a and 125b are adjustable to accommodate different interpupillary distances of different users. In some embodiments, the left and right eye pieces 125a and 125b may be adjusted independently based on the need of the surgeon's left and right visions, respectively. The left-eye and right-eye image displays may be 2D or 3D display screens. In some embodiments, the left-eye and right-eye image displays are liquid crystal display (LCD) screens.

Still referring to FIG. 2B, the left eye tracker 204a may be used for tracking the gaze point of the surgeon's left eye, and the right eye tracker 204b may be used for tracking the gaze point of the surgeon's right eye. In some embodiments, the eye tracking unit 200 may also include light emitters that can emit light to illuminate the surgeon's eyes, so that the gaze points of the surgeon's left and right eyes may be captured by the left and right eye trackers 204a and 204b respectively. The light emitters may or may not be integrated together with the left and/or right eye trackers 204a and 204b. In some embodiments, the light emitters may be Infrared (IR) light emitters, such as infrared light emitting diodes (IR LEDs). In some embodiments, the left and right eye pieces 125a and 125b may include suitable optical coatings configured to minimize reflection and maximize transmission of light from the light emitters and/or left and right eye image displays 202a and 202b. In some embodiments, the left and right eye trackers 204a and 204b include stereo cameras. In some embodiments, the left and right eye trackers 204a and 204b are Charged Coupled Device (CCD) cameras. In some embodiments, the left and right eye trackers 204a and 204b are infrared (IR) cameras that are sensitive to IR light and can capture the IR light emitted from IR light emitters. The left and right eye trackers 204a and 204b may be located in the stereo image viewer system 126, and may be mounted at the base of the left and right image displays 202a and 202b. The left and right eye trackers 204a and 204b and the left and right image displays 202a and 202b may be arranged in any suitable arrangements, as discussed in U.S. Provisional Application No. 61/955,334.

In some embodiments, the processor 206 is coupled to the left and right eye trackers 204a and 204b, and is configured to calculate the 3D location of the surgeon's gaze point with respect to image frame 165 of the image display 151 and translate that 3D position into the corresponding 3D position in the surgical frame 170 of the surgical field 155 (shown in FIG. 2A). For example, the gaze points captured by the left and right eye trackers 204a and 204b can be rectified, and the disparity between the gaze points of the surgeon's left and right eyes can be determined. The 3D location of the surgeon's gaze point can then be calculated using the distance between the left and right eye trackers 204a and 204b, the parameters related to the focal length of each of the left and right eye trackers 204a and 204b, and the determined disparity. In some embodiments, the processor 206 is included in the eye tracking imaging system 200 in the surgeon's console 120. In some embodiments, the processor 206 is included in the vision cart 140 shown in FIG. 1D, for example as part of the central electronic data processing unit 142. In some embodiments, the processor is part of the control system 22. In some embodiments, the processor 206 can also be coupled to a memory to store the 3D gaze point measurement, registration, and calibration data. In some embodiments, the processor 206 may be used to calculate the 2D location of the surgeon's gaze point. In some embodiments, the calculated 2D or 3D location of the surgeon's gaze point can be displayed in any of a variety of suitable representations, such as dots, flags, or vectors showing the changes of the surgeon's gaze point, and the surgeon's gaze point can be displayed in combination with the image of the surgical field 155 on the left and right image displays 202a and 202b.

In some embodiments, the head/face motion of the surgeon during a surgery can be tracked using the left and right eye trackers 204a and 204b. The calculated viewing location, which may be located at a 2D or 3D gaze point location, may be further adjusted or compensated for based on the tracked head/face motion of the surgeon. Additional details on process of head/face motion tracking and compensation may be found, for example, in U.S. Provisional Application No. 61/955,334, and in U.S. Application No. 61/865,996 entitled "ENDOSCOPE CONTROL SYSTEM", which is incorporated herein by reference in its entirety.

The eye tracking unit 200 may be coupled to an image display or gaze point display 210 as shown in FIG. 2B. In some embodiments, the gaze point display 210 is a 3D gaze point display. In some embodiments, the gaze point display 210 is the same as the image display 151 shown in FIG. 2A. The generated 2D or 3D location of the surgeon's gaze point may be output to the gaze point display 210 as any suitable representations, such as dots, flags or vectors showing the changes of the surgeon's gaze point. The image of the surgical field 155 may be displayed in combination with the 3D location of the surgeon's gaze point on the gaze point display 210. In some embodiments, the gaze point display 210 may be an external 3D image display. For example, the gaze point display 210 may be the 3D touch screen monitor 146 located at the vision cart 140 shown in FIG. 1D. In some examples, the gaze point display 210 may be mounted on the teleoperational assembly 100 shown in FIG. 1B. In some examples, the gaze point display 210 may be a portable display device, such as a tablet. In some instances, the gaze point display 210 may be presented simultaneously on multiple display screens or devices.

Thus, the eye tracking unit 200 comprises the gaze point display 210, which is configured to display images to the user, at least one eye tracker configured to measure data reflective of a gaze point of the user, and the processor 206, which is configured to process the data to determine a viewing location in the image on the gaze point display 210 at which the gaze point of the user is directed, and to control at least one function of the teleoperational medical system 10 based on the determined viewing location. For example, in some embodiments, the processor 206 of the eye tracking unit 200 may be coupled to an instrument control unit 212 that is configured to control the movement and energy discharge of at least one surgical instrument. The instrument control unit 212 may be a component of the control system 22. The instrument control unit 212 may include a separate processor and one or more actuators that control the functions of one or more surgical instrument. In some embodiments, the instrument control unit 212 is configured to control the activation, deactivation, and movement of one or more surgical instruments. In some embodiments, the processor of the instrument control unit 212 provides control signals to the one or more motors. For example, in one embodiment, the one or more motors may include a firing motor configured to release or fire a surgical instrument such as a stapler.

In some embodiments, the processor 206 of the eye tracking unit 200 may be coupled to a system control unit 214 that is configured to adjust various system parameters and characteristics of the teleoperational medical system 100. The system control unit 214 may be a component of the control system 22. The system control unit 214 may include one or more separate processors. The system control unit 214 may include one or more user interfaces that provide interaction between the surgeon and the teleoperational medical system 100. In some examples, the user interface includes the surgeon's console, display, keyboards, touch-screens, or other suitable input devices. The user interface may also include one or more software applications.

FIG. 2C illustrates a flowchart 215 describing an exemplary method of using the eye tracking units 200 to control and affect the teleoperational medical system 100 and/or any associated surgical instruments. Any of the method steps described herein may be implemented, at least in part, in the form of executable code stored on non-transient, tangible, machine readable media that may be run by one or more processors. At step 216, the user U, in the user frame 160 shown in FIG. 2A, gazes at a particular viewing location, (i.e., a 3D position) in the image shown on the image display 151, which is in the image frame 165. At step 218, the left and right eye trackers 204a, 204b of the eye tracking unit 200 observe and measure an eye characteristic (e.g., a characteristic reflective of eye gaze) of the user U. In some embodiments, the eye trackers 204a, 204b measure the eye gazes of each eye of the user relative to the image frame 165. At step 220, the processor 206 uses the measured eye gaze data from the eye trackers 204a, 204b to determine the 3D viewing location in the image on the image display 151 (within image frame 165) at which the user's eyes are directed. In some embodiments, the processor 206 may determine the viewed location by tracking incident angles of the light received by the eye trackers 204a, 204b from reflections off the eyes. In some embodiments, the processor 206 may initially perform a calibration process (e.g., the calibration process 302 described in FIG. 3A) to determine baseline incident angles as the user views target indicia that are displayed at known locations on the image display 151, and generate a functional relationship between the detected angles and the viewed locations on the image display 151. The processor 206 can then track the incident angles as the user views other locations on the image display 151 and use the generated functional relationship to determine (e.g., extrapolate from the calibrated angles and locations) the corresponding viewed locations.

At step 222, the processor 206 determines whether one of the displayed indicia (e.g., a menu option) on the image display 151 is being viewed by the user in a way that satisfies a defined condition for selection of that indicia (e.g., the indicia is in the viewing location and/or is in the viewing location for a predetermined duration). If so, at step 224, the user's selection of the indicia causes the processor 206 to initiate the function corresponding to the displayed indicia. For example, in some embodiments, the user's gaze may indicate the selection of an indicia associated with logging on to the teleoperational medical system 100, or with the illumination of the image display 151, or with various other system settings.

If not, at step 226, the processor 206 co-registers the viewed 3D location in the image frame 165 to the corresponding 3D location in the surgical field 155 in the surgical frame 170. At step 228, the processor determines whether the user is viewing the surgical field in a way that satisfies a defined condition for manipulating an imaging device or other surgical instrument in the surgical field that is visible on the image display 151. If so, at step 230, the user's gaze upon a particular area of the surgical field or a particular instrument within the surgical field causes the processor 206 to affect the relevant instrument in a fashion corresponding to the characteristics of the user's gaze. For example, in some embodiments, as mentioned above, if the user gazes at a particular region of the surgical field 155, the imaging device may "follow" the user's gaze and re-center its field of view (e.g., to position the center of its field of view at the user's gaze point). In other embodiments, if the user gazes at a particular surgical instrument for a predefined length of time, the surgical instrument may be activated automatically or by a second user event (e.g., via a pedal press, a foot switch, a finger switch, etc.). If not, at step 232, the eye trackers continue to evaluate the user's gaze for possible instructions.

In some implementations, as shown in FIG. 2D, two or more surgeon's consoles 120 (either co-located or remote from one another) may be networked together so that two users can simultaneously view and control tools at the surgical site. In some embodiments, two different surgeon's consoles 120 may be used by a proctor and a trainee during a training process, so that each user can view a distinct stereo image displaying eye gaze data obtained from two separate eye tracking units 200 (e.g., one eye tracking unit 200 on each console 120). FIG. 2C shows a training/proctoring system including a proctor's eye tracking unit 200 coupled to a trainee's eye tracking unit 240 according to some embodiments of the present disclosure. The trainee's eye tracking unit 240 may have substantially the same design and functionality of the proctor's eye tracking unit 200. As shown in FIG. 2D, the processor 206 of the proctor's eye tracking unit 200 is coupled to the left and right image displays 244a and 244b of the trainee's eye tracking unit 240. Similarly, the processor 248 of trainee's eye tracking unit 240 is coupled to the left and right image displays 204a and 204b of the proctor's eye tracking unit 200. Thus, the gaze point displays of the proctor may be displayed to the trainee, and the gaze point displays of the proctor may be displayed to the proctor.

For example, in some embodiments, the proctor's 3D eye gaze point can be demonstrated on a 3D gaze point display 250 of the trainee's eye tracking unit 240 so that the trainee may have a direct view of the proctor's gaze point in real-time during the procedure. In some embodiments, the proctor's 3D eye gaze point may be shown as stereo images on the left and right image displays 244a and 244b of the trainee's eye tracking unit 240, so that the trainee may be assisted in real-time to complete the surgery using the proctor's gaze point as a visual guide to follow. In some embodiments, during a training process, the 3D gaze point of the trainee may be shown on the display 210 or the left and right image displays 202a and 202b of the proctor's eye tracking unit 200, so that the performance of the surgeon may be monitored and evaluated by the proctor in real time. In other embodiments, both the proctor and trainee gaze points may be shown in one or both of the proctor and trainee displays, thereby allowing either one or both users to see any disparity between their gaze points. In this manner, the proctor may be able to provide timely instructions to the trainee, so that the trainee can focus on the correct surgical site in real-time and avoid incorrect actions.

In some embodiments, the control of the endoscope 112 and/or other surgical instruments 110 may be switched between the proctor and the trainee. Alternatively, the endoscope 112 and/or other surgical instruments 110 may be simultaneously manipulated by both the proctor and the trainee. Although in FIG. 2D, the processors 206 and 248 are included in eye tracking units 200 and 240 separately, one of ordinary skill in the art would recognize other variations. For example, the training/proctoring system can include one processor for the eye tracking units of both users.

Figure 3A:
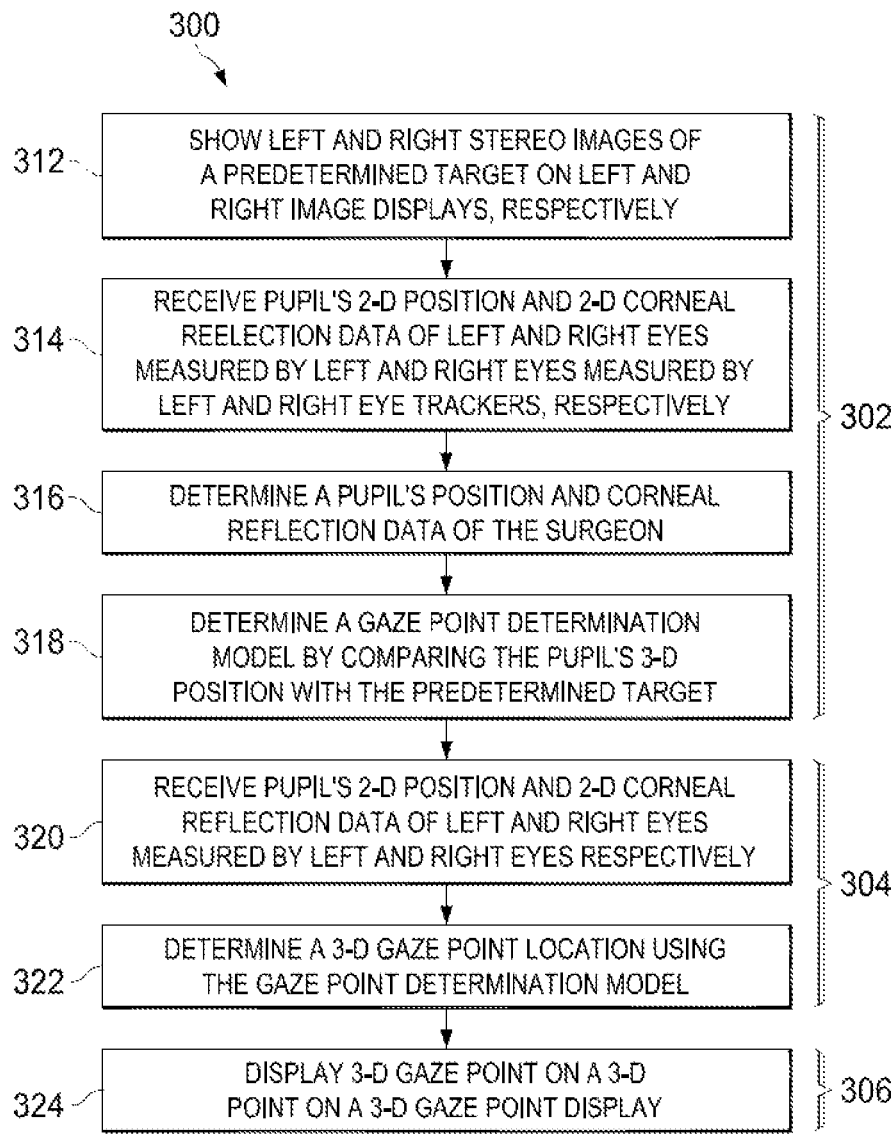
FIG. 3A illustrates an exemplary method for determining and displaying the surgeon's 3D gaze point using the eye tracking unit 200 of FIG. 2B according to one embodiment of the present disclosure.

FIG. 3A illustrates a method 300 for determining the surgeon's viewing location in the image frame using the eye tracking unit 200 of FIG. 2B according to some embodiments of the present disclosure. The surgeon's viewing location may be a 3D gaze point as described. However in alternative embodiments a 2D gaze point may be used. The method 300 includes three processes: a calibration process 302, a measurement process 304, and an output process 306. In some embodiments, the calibration process 302 is a 3D calibration process, where the surgeon's gaze point in the 3D space of the image frame is compared with a predetermined target in the 3D space of the image frame with known 3D location parameters.

The calibration process 302 starts from step 312 by showing a target in the image frame. In some examples, the target may be a surgical tool icon. The target may be a moving target, or a target that may change size dynamically. Alternatively, the target may also be an actual surgical tool in the surgical field, the location of which can be tracked and identified using any suitable tool tracking technology. For example, the calibration process 302 may incorporate features disclosed in U.S. Patent Publication No. 2006/0258938, entitled "Methods and system for performing 3D tool tracking by fusion of sensor and/or camera derived data during minimally invasive robotic surgery," filed on May 16, 2005, which is incorporated herein by reference in its entirety. The image of the target shown in the 3D image frame may be separated into left and right stereo images, and displayed on the left and right image displays 202a and 202b shown in FIG. 2B, respectively. During the calibration process, the 3D location of the target is predetermined, for example with known 3D location parameters in the 3D image frame, so that the measured data may be compared with the known location parameters of the target to determine various models in the following steps.

In the pictured embodiment, the calibration process 302 proceeds to step 314 by receiving the pupil's 2D position and 2D corneal reflection data of left and right eyes captured by the left and right eye trackers 204a and 204b, respectively. In some embodiments, the pupil's 2D position and 2D corneal reflection data may include coordinate values, displacements, and/or angles. In some embodiments, the surgeon's head/face motion may also be captured by the left and right eye trackers 204a and 204b.

The calibration process 304 proceeds to step 316 by determining a pupil's position and corneal reflection data of the surgeon using the pupil's 2D position and 2D corneal reflection data of the surgeon's left and right eyes. In some embodiments, the left and right eye trackers include stereo cameras, and stereo images including the pupil's 2D position and 2D corneal reflection data can be captured and processed by the processor 206 to calculate a disparity between the two stereo images. In some embodiments, the determined position data may include the pupil's 2D position and 2D corneal reflection data of the surgeon. The determined 2D position data of each eye may then be combined to estimate the 3D eye gaze location of the surgeon. In some embodiments, the determined position data may include the pupil's 3D position and 3D corneal reflection data. The 3D data including depth of the surgeon's pupil and corneal reflection may be estimated using the disparity. For example, the 3D data of the surgeon's left eye may be calculated using the distance between the left eye trackers 204a, the parameters related to the focal length of each of the left eye trackers 204a, and the calculated disparity. A disparity to depth conversion map may be obtained during the calibration process using this method. In some embodiments, the pupil's position and corneal reflection data may be compensated for the captured head/face motion.

At step 318 of the calibration process 302, the pupil's determined 3D position and 3D corneal reflection data is compared with the predetermined 3D location parameters of the predetermined target to determine a gaze point determination model. In some embodiments, the gaze point determination model may include a function that can be used to map the 3D eye gaze location using the pupil's determined position and corneal reflection data. In some embodiments, a plurality of calibration targets are used for the calibration processes, and the parameters in the function may be determined using the pupil's position and corneal reflection data gathered from the calibration processes. In some examples, methodologies such as least squares optimization, or maximum likelihood estimation may be used to determine the parameters of the function. In some embodiments, the gaze point determination model may also include a matrix showing the conversion from the pupil's 3D position and 3D corneal reflection data to the 3D location of the target in a coordination system in the 3D space. In some embodiments, the gaze point determination model may be saved in a memory coupled to the processor 206. Additional details on how to determine the pupil's 3D position and 3D corneal reflection data and the details related to the gaze point determination model may be found, for example, in U.S. Provisional Application No. 61/955,334 filed Mar. 19, 2014 which is incorporated by reference herein in its entirety.

In some embodiments, the calibration process 302 may be repeated multiple times, so that the accuracy of the gaze point determination model may be improved to satisfy a predetermined system requirement. In some embodiments, after a first gaze point determination model is formed, a real target may be used to estimate the accuracy of the first gaze point determination model. For example, by re-running the mapping optimization using the real target, the first gaze point determination model may be updated to form a second gaze point determination model. The accuracy between the first and second models is compared and evaluated, so that a more accurate gaze point determination model may be formed.

After the calibration process 302 is completed, the method 300 proceeds to measurement process 304. The measurement process 304 may be carried out during a surgery or a training process when the endoscope 112 is capturing an image of a surgical site.

The measurement process 304 starts at step 320 by receiving the pupil's 2D position and 2D corneal reflection data for the surgeon's left and right eyes when the surgeon is looking at the surgical site displayed on left and right image displays 202a and 202b. The image of the surgical site may be captured by endoscope 112, and processed and separated into left and right stereo images displayed on left and right image displays 202a and 202b, respectively. The pupil's 2D position and 2D corneal reflection data of surgeon's left and right eyes are captured by left and right eye trackers 204a and 204b respectively. In some embodiments, surgeon's head/face motion may also be captured by left and right eye trackers 204a and 204b.

The measurement process 304 proceeds to step 322 by determining a 3D gaze point location of the surgeon using the gaze point determination model obtained during the calibration process 302. The pupil's 3D position and 3D corneal reflection data may first be determined using the pupil's 2D position and 2D corneal reflection data using substantially similar method with regard to step 316 of the method 300 as previously discussed. In some embodiments, the captured heard/face motion at step 320 may also be used to compensate the pupil's position and corneal reflection data or the surgeon's 3D gaze point. In some examples, during calibration process 302, the corners of the surgeon's eyes may be tracked while the surgeon focuses on a calibration target using his or her pupils and rotates his or her head. A function between the head/face motion and the tracked motions of the eye corners can be formed during the calibration processes. During the measurement process 304, the motions of the eye corners may also be tracked, and the surgeon's head/face motions may be estimated using the formed function from the calibration process 302. The pupil's 3D position and 3D corneal reflection data may then be converted to the surgeon's 3D gaze point location by the processor 206 by using the gaze point determination model obtained at step 318.

At step 324 of the output process 306, the determined 3D gaze point location may be shown onto the gaze point display 210 shown in FIG. 2B. The 3D gaze point location may be expressed in any of a variety of suitable representations, such as, without limitation, dots, lines, vectors, arrows, and semi-transparent circles. In some embodiments, the proctor's 3D eye gaze point (e.g., determined by the processor 206 of the proctor's eye tracking unit 200) may be demonstrated on the 3D gaze point display 250 of the surgeons' eye tracking unit 240 (as shown in FIG. 2D) so that the surgeon being trained may have a direct view of the proctor's gaze point. In some embodiments, the proctor's 3D eye gaze point may be shown on the left and right image displays 244a and 244b of the surgeon's eye tracking unit 240, so that the surgeon may be guided to complete the surgery using the proctor's gaze point intuitively. In some embodiments, the surgeon's 3D eye gaze point (e.g., determined by the processor 248 of the surgeon's eye tracking unit 240) may be demonstrated on the display 210 of the proctor's eye tracking unit 200 so that the surgeon's gaze point may be monitored by the proctor in real time during the surgery. The gaze point measured by the teleoperational medical system 10 as discussed above may be used in various applications.

Figure 3B:
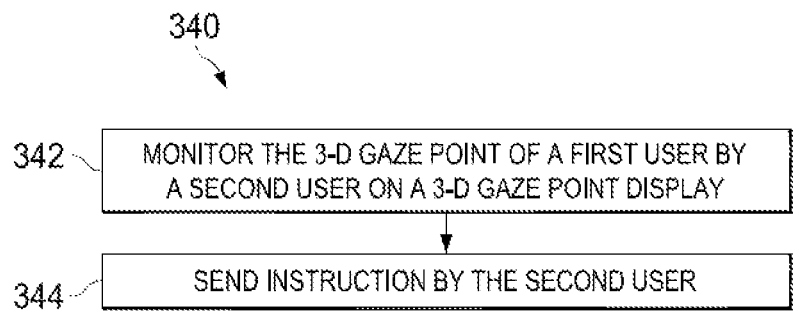
FIG. 3B illustrates an exemplary training/proctoring method using dual eye tracking units of FIG. 2D according to one embodiment of the present disclosure.

FIG. 3B illustrates a training/proctoring method 340 using dual eye tracking units 200 and 240 of FIG. 2D. The method 340 starts from step 342 by monitoring the 3D gaze point of a first user by a second user on a 3D gaze point display during the surgery. The 3D gaze point of the first user may be determined using a first eye tracking unit (e.g., the eye tracking unit 200) as illustrated in the method 300 shown in FIG. 3A. The determined 3D gaze point may be displayed on the 3D gaze point display (e.g., the image display 244 or the gaze point display 250) of a second eye tracking unit (e.g., the eye tracking unit 240) to be monitored and evaluated by the second user. Method 340 proceeds to step 344 by the second user sending instruction to the first user. In some embodiments, the first user may be a surgeon, and the second user may be a proctor who trains the surgeon during the surgery. For example, in one instance, when the proctor notices that the surgeon is looking at an area within the surgical site that is different from the target area within the surgical site, or that the surgeon has selected the wrong surgical instrument, the proctor may send an instruction to the surgeon to correct the surgeon's actions and/or viewpoint in real-time. For example, the proctor may instruct the surgeon by eye-gaze activated menu selection, manually pressing a button, or tapping a foot pedal on the proctor's console. In one instance, the proctor's instruction manifests on the surgeon's image display in any of a variety of ways to guide the surgeon towards the correct approach. In one embodiment, the image displays of the surgeon (e.g., left and right image displays 202a and 202b of eye tracking unit 200) may become dark. In another embodiment, the gaze point region of the surgeon's image displays may present a visual (e.g., blink red), audible (e.g., sound a buzzer), or tactile (e.g., vibrate a part of the manual controls) warning to warn the surgeon from proceeding with any incorrect operation. In some embodiments, the proctor may also send the instruction using a telestrator or video marker on the touch screen or a 3D pointer on the surgeon's console or a separate console.

As described above, in some embodiments, the surgeon may use the surgeon's 3D gaze point to label and to locate the surgical site. For example, when the surgeon wants to label a location in the anatomy, the surgeon may stare at the location, so that the eye tracking unit 200 captures the surgeon's 3D gaze point and determines the 3D coordinate values using the method 300. Then the surgeon may further press a button on the surgeon's console 120, or tap a foot pedal 128, to label the location at the current gaze point on the image displays using an icon, such as a flag. As the endoscope 112 focuses on other quadrants in the anatomical environment, the labeled 3D location may be compensated for subsequent camera movements, or by being referenced from an external position sensor to retain the labeled location. The labeled location may be used as a reference location which could help the surgeon identify the desired surgical site efficiently and effectively.

With regard to the method 300 shown in FIG. 3A, in some embodiments, the 3D gaze point location captured by the eye tracking unit 200 may be used to adjust endoscope 112 so that the surgeon's 3D gaze point is at the center of the vision. For example, when the surgeon's 3D gaze point is confirmed to be the surgical site, the surgeon may send a confirmation instruction, for example by pressing a button and/or tapping a foot pedal. A control unit of the endoscope 112 may then receive the location data of the 3D gaze point from processor 206, so that the endoscope 112 may be adjusted to capture an updated image having the 3D gaze point of the surgeon located at the center of the image. Additional details on adjusting endoscope 112 using the 3D gaze point may be found, for example, in U.S. Provisional Application No. 61/955,355, filed Mar. 19, 2014, entitled "MEDICAL DEVICES, SYSTEMS, AND METHODS USING EYE GAZE TRACKING FOR SECONDARY IMAGING," which is incorporated herein by reference in its entirety.

Figure 3C:
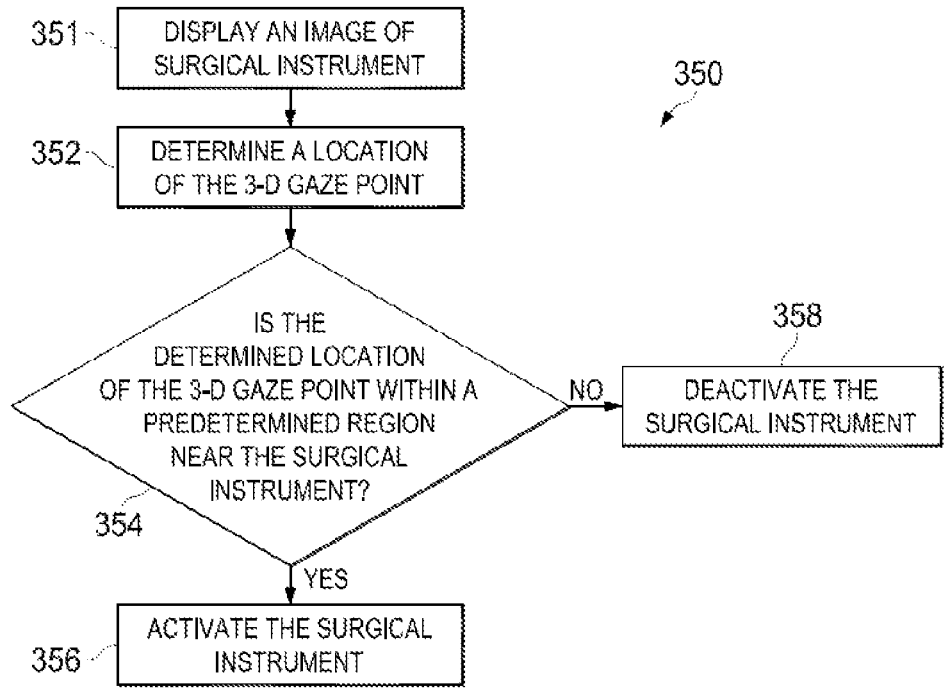
FIG. 3C illustrates an exemplary gaze point confirmation method for confirming and activating a corresponding control interface to deliver a predetermined surgical instrument to be used in the operation according to one embodiment of the present disclosure.

FIG. 3C illustrates a gaze point activation method 350 for activating a surgical instrument (e.g., instrument system 14), mounted in the teleoperational assembly 100, using the surgeon's gaze point during a surgery. The surgeon is first required to focus on the image of the surgical instrument to be used in the operation, such as a fastener delivery tool (e.g. a stapler) or an energy application tool (e.g., an ablation instrument), through the eye tracking unit 200. The 3D location data of the surgical instrument in the image frame is stored in a computer readable media, such as a memory. The 3D location of the 3D image of the surgical instrument in the image frame is referenced to the 3D location of the surgical instrument in the surgical frame. At step 351, the image of the surgical instrument captured by the endoscope 112 is displayed on the display 210 (e.g., on the image displays 202a and 202b of the eye tracking unit 200) for the surgeon's view. At step 352 of the method 350, the surgeon's gaze point in the image frame is determined using a substantially similar method as illustrated in the method 300 when the surgeon is required to focus on the image of the surgical instrument on the display. In some embodiments, the surgeon may focus his or her gaze point on the image of the surgical instrument or in a region of the image near the surgical instrument, such as the tissue near the tip of the surgical instrument. At step 354, the determined location of the surgeon's 3D gaze point is compared with the 3D location data of the surgical instrument stored in the computer readable media. If the determined location of the surgeon's 3D gaze point coincides with the 3D location of the surgical instrument, or if the determined location of the surgeon's 3D gaze point is within a predetermined region near the surgical instrument, step 354 proceeds to step 356 to activate the surgical instrument. For example, the processor 206 of the eye gaze tracking system may send a signal to instrument control unit 212 to enable the energy discharge of the surgical instrument, such as a stapler. The surgeon is then able to control and fire the stapler using the corresponding control interface 122. In some embodiments, the processor 206 can also activate and control the control interface 122 to deliver the surgical instrument to be used by the surgeon for the surgery. If the determined location of the surgeon's 3D gaze point is not within the predetermined region near the surgical instrument, at step 358, the surgical instrument is deactivated. At step 358, because the surgeon is not looking at the instrument, the instrument control unit 212 cannot be activated by any of the surgeon's physical instructions (e.g., which may be inadvertent) and the surgical instrument is locked. Therefore, the surgical instrument cannot perform any firing action or movement without the confirmation of the surgeon's gaze point as discussed in method 350.

During a training process, the current 3D gaze point location of a surgeon being trained may be monitored and evaluated by a proctor from various perspectives, such as skill level and/or stress level. In some embodiments, the skill level of the surgeon may be characterized by tracking the gaze point movement during the surgical process. FIG. 4A illustrates a method 400 for evaluating a surgeon during a surgery using the eye tracking unit 200 of FIG. 2B. The evaluation may include the surgeon's skill level, stress level, fatigue, and/or any other gaze-indicated performance or behavioral metric. FIG. 5 is an example of a 3D image display 450 showing a 3D image of a surgical site with a 3D image frame coordinate system.

The method 400 starts from optional step 402 by acquiring baseline data as standards to evaluate and quantify the surgeon's skill level. In some embodiments, the baseline data may be acquired before starting the training process, by measuring an experienced surgeon's gaze point movement during a standard operation. In some examples, the baseline data may be acquired during simulation exercises, which may include camera targeting, needle driving, manipulation exercises, suturing, cautery/energy application, and/or any other suitable exercises. In some examples, the baseline data may include information related to the time ratio (T) and/or displacement ratio (D) of the time and/or displacement of the gaze point moving back and forth between a target surgery area and the surgical instrument, and the time and/or displacement of the gaze point moving from an initial position to the target surgery area. In some embodiments, the baseline data may also include time of gaze point fixation on each tracking point. In some embodiments, the baseline data may be captured combined with the system kinematic and event data. In some embodiments, there may be different values of the time ratio (T) and/or displacement ratio (D) representing various levels of skill. In some embodiments, the baseline data may be saved in a computer readable media to be used repeatedly in the future.

The method 400 proceeds to optional step 404 by confirming a target P on the 3D image display 450 as shown in FIG. 5. A first signal indicating the start of the confirming process may be output by the surgeon being trained by pressing a button to select a confirmation mode, or by tapping a foot pedal on the surgeon's console. As show in FIG. 5, after a target area P is identified to be the area in need for surgery, the target P may be confirmed on the 3D image display 450 by focusing the surgeon's gaze point on the target P on the image display 450. In some embodiments, the target P may also be confirmed and labeled by pressing a button on the surgeon's console 120, or by tapping a foot pedal 128. In other embodiments, the target P may be a predetermined location or region within display 450, or can even be established on the fly by the actual gaze location(s) accessed by the surgeon.

After the eye tracking unit 200 receives the confirmation, by receiving another instruction, such as pressing a button and/or tapping a foot pedal, a control unit of the endoscope 112 may optionally receive the location data of the gaze point (i.e., target P) from processor 206, so that the endoscope 112 may be adjusted to have target P located at the center of the image display 450. In some embodiments, the target P may be automatically assigned with coordinates of (0, 0, 0) as the origin of the current 3D coordinate system.

Method 400 proceeds to optional step 406 by confirming an initial location of the tip of a surgical instrument 110a, 110b or 110c on the 3D image display 450. For example as shown in FIG. 5, the initial location of the tip of a surgical instrument may be identified at a position $Q_0$. The position $Q_0$ may then be confirmed on the 3D image display 450 by focusing the surgeon's gaze point on the position $Q_0$ on the 3D image display 450. After eye tracking unit 200 receives the confirmation, the position $Q_0$ may be automatically assigned with 3D coordinates of $(q_{x0}, q_{y0}, q_{z0})$ relative to the corresponding 3D coordinate system defined at step 404. In some embodiments, the position $Q_0$ may also be confirmed by pressing a button on the surgeon's console 120, or by tapping a foot pedal 128. In other embodiments, the location of the tip of the instrument may be established via any other method, such as system kinematics, position sensors, and/or optical tool tracking.

Method 400 proceeds to step 408 by measuring the surgeon's gaze point movement, for example relative to the instrument tip and the target P. In some embodiments, upon the completion of step 406, a signal indicating the start of the measurement process may be generated by any suitable method, such as the surgeon pressing a button on the surgeon's console, or tapping a foot pedal. In other embodiments, the measurement process may be ongoing or initiated by a particular state of the instrument. In some embodiments, the surgeon's gaze point may start from the target area P on the 3D image display 450. In some embodiments, the surgeon's gaze point may start from the initial position $Q_0$ of the surgical instrument on the 3D image display 450.

Referring to FIG. 5, in some embodiments, the surgeon's skill level may be reflected by the surgeon's gaze point movement. For example, during a surgery, an amateur surgeon may move his or her gaze point back and forth for multiple times to check between the surgical instrument (e.g., $Q_0, Q_1, Q_2, \ldots$) and the target point (e.g. P) as he or she moves the surgical instrument from the initial point to the target point, or performs an operation from the initial point to the target point. In contrast, an experienced surgeon may have smoother and less frequent gaze point movement between the initial gaze point (e.g., $Q_0$) and the target point (e.g. P) as he or she moves the surgical instrument or performs the operation. Therefore, in one embodiment, the displacement and/or the time of a surgeon's gaze point movement may be used as one or more factors to evaluate the skill level of the surgeon.

At step 408, the location data of the surgeon's gaze point may be captured by the left and right eye trackers 204a and 204b, processed by the processor 206 to receive 3D location data of the gaze point, and saved in a memory in real time as discussed above with respect to the method 300 shown in FIG. 3A. The location data of the surgeon's gaze point may include the 3D coordinate values of $(q_{x0}, q_{y0}, q_{z0})$, $(q_{x1}, q_{y1}, q_{z1})$, $(q_{x2}, q_{y2}, q_{z2}) \ldots (q_{xn}, q_{yn}, q_{zn})$ as the surgeon's gaze point moves from the initial position $Q_0$, to $Q_1, Q_2, \ldots Q_n$ on the 3D image display 450.

At step 408, the time of surgeon's gaze point movement from one point to the next may also be captured by the left and right eye trackers 204a and 204b, processed by the processor 206, and saved in a memory in real time. In some embodiments, the time for the surgeon's gaze point movement may include information related to the moving direction. In some embodiments at step 408, a fixation time at each gaze point may also be tracked.

The method 400 proceeds to step 410 by determining an evaluation factor. The evaluation factor may include a displacement ratio factor D. The displacement ratio factor D is used for quantifying the skill level of the surgeon. For example, the displacement ratio factor D may be calculated as $D=(|Q_0P|+|PQ_1|+|Q_1P|+|PQ_2|+|Q_2P|+ \ldots +|PQ_n|+|Q_nP|)/|Q_0P|$, where $|AB|$ represents the displacement of gaze point A toward gaze point B using the coordinate values of points A and B on 3D image display 450. For example, $|PQ_1|$ represents the displacement from gaze point P (0, 0, 0) toward gaze point $Q_1$ $(q_{x1}, q_{y1}, q_{z1})$, and $|Q_1P|$ represents the displacement from gaze point $Q_1$ $(q_{x1}, q_{y1}, q_{z1})$ toward gaze point P (0, 0, 0).

In some embodiments, the evaluation factor may include a time ratio factor T. The time ratio factor T may also be used for quantifying the skill level of the surgeon. For example, the time ratio factor T may be calculated as $T=(t_1+t_2+ \ldots +t_n)/t_1$, where $t_1, t_2, \ldots, t_n$ represents the time of the surgeon's gaze point needed to move from one point to the next, until the completion of the measurement process. During the measurement process, since both displacement (e.g., $|PQ_1|$) and time (e.g., $t_1$) are captured between any two moving points, the velocity ($v_i$) of the gaze point moving between any two points may also be calculated. An average velocity (v) may be further calculated at the completion of the measurement process. The average velocity (v) may be then used to calculate the time $t_i$ for the current user to move his or her gaze point from the initial point (e.g., $Q_0$) to the target point (e.g., P).

In some embodiments, the evaluation factor may include a factor related to the fixation time measured at each gaze point. For example, an average fixation time of eye gaze of the surgeon may be calculated after measuring a plurality of fixation times at a plurality of gaze points at step 408. The average time of eye gaze fixation may then be compared with the eye gaze fixation information stored in the baseline data for evaluating the surgeon's skill level.

The method 400 proceeds to step 412 by determining the surgeon's skill level by comparing the evaluation factor (e.g., the displacement ratio factor D, time ratio factor T, and/or gaze fixation time) against the baseline data (e.g., acquired at step 402). In some embodiments, the surgeon's skill level may also be determined using the evaluation factor combined with system kinematic data and/or event data, such as data measured from the movements of the surgeon's hand, instrument, and/or camera. The surgeon's hand, instrument, and/or camera movements may be tracked and analyzed using any suitable method.

In some embodiments, as described above, the surgeon's 3D gaze point location captured by the eye tracking unit 200 may also be used to monitor the performance and/or condition of the surgeon and provide a warning should a drop in that performance and/or condition be indicated. For example, the 3D gaze point may be used to determine the surgeon's stress or fatigue level, which in some embodiments may be reflected in the change of the surgeon's eye gaze dynamics. Eye gaze dynamics may include pupil diameter fluctuations, and/or eye gaze saccades. In some examples before the measurement process (e.g., step 402 of method 400 of FIG. 4A), a baseline including information of the surgeon's eye gaze dynamics when the surgeon is working in a normal status may be first acquired. For example, the baseline may include frequency of the surgeon's eye gaze saccades, and/or frequency and magnitude of the surgeon's pupil diameter fluctuation. During the measurement process (e.g., step 408 of method 400), the eye gaze dynamics may be monitored using the left and right eye trackers 204a and 204b and processed and compared with the baseline acquired under normal working status. When the eye gaze dynamics appear to be abnormal compared to the normal status (e.g., step 412 of method 400), a notice or an alarm may be given to prevent the surgeon from proceeding with any operation. Abnormal eye dynamics may be indicated by various eye characteristics, such as, without limitation, drastic pupil diameter fluctuation or more frequent eye gaze saccades than normal. In some embodiments, the surgeon's eye dynamics may also be monitored on a touch screen located at the teleoperational assembly 100, and the notice or the alarm notifying the abnormal status of the surgeon's eye dynamics may be sent to the operating room (OR) staff so that the staff may respond in a timely fashion.

In some embodiments, in addition to monitoring the surgeon's stress level during a medical procedure, the tracked eye gaze dynamics information may also be gathered and analyzed after the procedure. In some examples, the analyzed result may be used to understand why a surgeon has difficulties with a particular training exercise or a particular portion of the surgery.

In some embodiments, the tracked surgeon's 3D gaze point can be used for system login/logout and user identification. For example, in one embodiment, the surgeon is required to focus on a target point before becoming logged into the system. The target point may include a surgical instrument of which the 3D location data is stored in the computer readable media. After the location of the surgeon's 3D gaze point is tracked by the eye tracking system using method 300 as discussed earlier, the location of the surgeon's 3D gaze point is compared with the 3D location of the target point. When the surgeon's 3D gaze point coincides with the 3D position target point, the surgeon may be automatically logged into the teleoperational medical system 10. In some embodiments, if the surgeon's 3D gaze point does not match with the 3D location of the target point, the surgeon cannot log into the teleoperational medical system 10. In some examples, the teleoperational medical system 10 is locked down or inactivated if the surgeon's eyes (and/or the surgeon's gaze point) cannot be detected.

In some embodiments, the stored eye information of a user, such as iris characteristics, eye dynamics, or eye gaze movement velocity, can be used for user recognition and system login. For example, before starting a surgery, the surgeon may be required to conduct several eye gaze movement exercises. The eye tracking unit 200 may capture the eye dynamics of the surgeon, and compare with the profile data related to the corresponding eye dynamics. In some embodiments, the eye tracking unit 200 may observe or measure various iris characteristics of the user and compare these iris characteristics to a database of stored iris profiles to enable iris recognition of different users. Once the surgeon is identified to be a reoccurring user with a profile saved in the memory, the surgeon may be automatically logged in to his or her own profile with customized settings.

In some embodiments, the surgeon's 3D gaze point location captured by the eye tracking unit 200 may be used to adjust the system characteristics of the teleoperational medical system 10 using system control unit 214 shown in FIG. 2B. For example, the measured eye gaze of the surgeon includes 3D location data of a surgical site (which can be in a live patient, cadaver, animal, model, or partial/full computer simulation). The 3D location data can be used for aligning the user interface (e.g., the control interfaces 122a and 122b of FIG. 1B) at a proper location (e.g., a proper depth) relative to the surgical site on the 3D image display, so that the surgeon can view the surgical site on the 3D image display and control the surgical instrument intuitively during a surgery. In some embodiments, the measured eye gaze of the surgeon can be used to adjust the ergonomic settings of the surgeon console such as the position and orientation of the image displays relative to the user's head so that the user can see the entire image display without occlusions.

In some embodiments, in order to more accurately calibrate the 3D location of the surgical instrument in the 3D space, the surgeon's eye gaze point may be focused on the surgical instrument on the image display, and the eye tracking unit 200 may capture the surgeon's 3D eye gaze point and provide accurate 3D location information of the surgical instrument based on the gaze point data received by the eye tracking unit 200.

In an exemplary embodiment, a first teleoperational medical system comprises a first eye tracking unit including: one or more first image displays; one or more first eye trackers; and a first processor coupled to the one or more first eye trackers and configured to calculate a first gaze point of a first user when the first user looks at a first image displayed by the one or more first image displays. The system also comprises a second eye tracking unit including: one or more second image displays; one or more second eye trackers; and a second processor coupled to the one or more second eye trackers and configured to calculate a second gaze point of a second user when the second user looks at a second image displayed by the one or more second image displays. The one or more first image displays are coupled to the second processor, and the one or more second image displays are coupled to the first processor.

In another embodiment of the first teleoperational medical system, the first image and the second image include an image of a surgical site.

In another embodiment of the first teleoperational medical system, the first image further includes a representation of the second gaze point.

In another embodiment of the first teleoperational medical system, the second image further includes a representation of the first gaze point.

In another embodiment of the first teleoperational medical system, the first image further includes a representation of the first gaze point.

In another embodiment of the first teleoperational medical system, the one or more first eye trackers include a left eye tracker and a right eye tracker.

In another embodiment of the first teleoperational medical system, the one or more second eye trackers include a left eye tracker and a right eye tracker.

In an exemplary embodiment, a first method for operating a teleoperational medical system comprises tracking movement of a 3D gaze point in a 3D image display of a surgical site; and determining an evaluation factor from the movement of the 3D gaze point.

In another embodiment of the first method for operating a teleoperational medical system, the method further comprises confirming a target spot and an initial spot in the 3D image display, wherein the movement is between the target spot and the initial spot.

In another embodiment of the first method for operating a teleoperational medical system, confirming the target spot and the initial spot includes acquiring coordinate values of the target spot and the initial spot.

In another embodiment of the first method for operating a teleoperational medical system, the acquired coordinate values of the target spot are used to re-center an endoscope.

In another embodiment of the first method for operating a teleoperational medical system, confirming the target spot and the initial spot includes pressing a button or tapping a foot pedal.

In another embodiment of the first method for operating a teleoperational medical system, confirming the target spot includes focusing the 3D gaze point on the target spot on the 3D image display.

In another embodiment of the first method for operating a teleoperational medical system, confirming the initial spot includes focusing the 3D gaze point on the initial spot on the 3D image display.

In another embodiment, the first method for operating a teleoperational medical system comprises determining a skill level by comparing the evaluation factor with baseline data for gaze point movement.

In another embodiment of the first method for operating a teleoperational medical system, the movement of the 3D gaze point between the target spot and the initial spot includes a plurality of segmental movements of the 3D gaze point, each segmental movement being from an instrument spot to the target spot, and wherein the instrument spot is between the initial spot and the target spot.

In another embodiment of the first method for operating a teleoperational medical system, measuring the movement of the 3D gaze point includes measuring 3D coordinate values of the instrument spot.

In another embodiment of the first method for operating a teleoperational medical system, the evaluation factor includes a displacement ratio factor, the displacement ratio factor being the ratio between a sum of displacements of the segmental movements of the 3D gaze point, divided by the displacement between the target spot and the initial spot.

In another embodiment of the first method for operating a teleoperational medical system, measuring the movement of the 3D gaze point includes measuring time needed for each segmental movement of the 3D gaze point between the target spot and the instrument spot.

In another embodiment of the first method for operating a teleoperational medical system the evaluation factor includes a time ratio factor, the time ratio factor being the ratio between a sum of time needed for the segmental movements, divided by a time needed for the 3D gaze point to move from the initial spot to the target spot calculated using an average 3D gaze point moving velocity.

In another embodiment of the first method for operating a teleoperational medical system, the average 3D gaze point moving velocity is a mean value of all 3D gaze point moving velocities, each of the 3D gaze point moving velocities calculated using displacement and time of each segmental movement.

In another embodiment of the first method for operating a teleoperational medical system, measuring the movement of the 3D gaze point includes measuring a fixation time of the 3D gaze point at an instrument spot between the initial and the target spot.

In another embodiment of the first method for operating a teleoperational medical system, the evaluation factor includes an average fixation time calculated by using a plurality of fixation times measured on a plurality of instrument spots between the initial and the target spot.

In an exemplary embodiment, a second method for operating a teleoperational medical system, the method comprises tracking eye gaze dynamics in a 3D image display of a surgical site and determining a condition of a user when the user looks at the 3D image display.

In another embodiment of the second method for operating a teleoperational medical system, the tracking the eye gaze dynamics includes tracking at least one of pupil diameter fluctuations or eye gaze saccades of the user using one or more eye trackers.

In another embodiment of the second method for operating a teleoperational medical system, the condition of the user includes at least one of a stress level or a fatigue level of the user.

In another embodiment of the second method for operating a teleoperational medical system, determining the stress level includes comparing the eye gaze dynamics with baseline data for the eye gaze dynamics.

In another embodiment of the second method for operating a teleoperational medical system, the baseline data includes the eye gaze dynamics measured when the surgeon works in a normal status.

In another embodiment of the second method for operating a teleoperational medical system, the eye gaze dynamics is used for user's recognition during a system login process.

In an exemplary embodiment, a first method for operating a surgical system comprises determining a 3D gaze point for a first user viewing a 3D image in a first display; and displaying the 3D gaze point in the 3D image in a second display; and receiving an instruction from a second user viewing the 3D gaze point of the first user on the second display.

In another embodiment of the first method for operating a surgical system, the first user is being trained by the second user.

In another embodiment of the first method for operating a surgical system, the 3D gaze point of the first user is determined by an eye tracking unit.

In another embodiment of the first method for operating a surgical system, the instruction from the second user is sent using a telestrator on the second display.

In an exemplary embodiment, a second method for operating a surgical system, including an instrument and a 3D display, comprises: displaying a 3D image on the 3D display; determining a location of a 3D gaze point for a user viewing the 3D image; and comparing the 3D image and the location of the 3D gaze point.

In another embodiment of the second method for operating a surgical system, the location of the 3D gaze point is determined using an eye tracking unit.

In another embodiment of the second method for operating a surgical system, the 3D image includes a 3D image of the instrument displayed on one or more image displays of the eye tracking unit.

In another embodiment, the second method for operating a surgical system includes activating the instrument when the location of the 3D gaze point is within a predetermined region around the 3D image.

In another embodiment of the second method for operating a surgical system, activating the instrument includes activating a control interface to deliver the instrument to be used by the user.

In another embodiment of the second method for operating a surgical system, activating the instrument includes controlling an instrument control unit to enable energy discharge of the instrument.

In another embodiment, the second method for operating a surgical system includes deactivating the instrument when the location of the 3D gaze point is out of a predetermined region around the 3D image.

In another embodiment, the second method for operating a surgical system includes enabling an automatic login to the surgical system when the location of the 3D gaze point is within a predetermined region around the 3D image.

In another embodiment, the second method for operating a surgical system includes adjusting system characteristics.

In another embodiment of the second method for operating a surgical system, the 3D image includes a 3D image of a surgical site.

In another embodiment of the second method for operating a surgical system, adjusting the system characteristics includes aligning a user interface relative to the surgical site displayed on the 3D display.

In various embodiments, the eye tracking system 200, the control unit 210 and an imaging system (e.g., the imaging device 112) operate in concert to provide the user with a primary image and, optionally, a variety of secondary adjusted images. The adjusted image may comprise, by way of non-limiting examples, a magnified image, a brightened image, a sharpened image, a colorized image, a labeled image, and/or an image involving a different wavelength range (e.g., a near infrared range as opposed to a visible light range). The adjusted image of a surgical area may be controlled, at least in part, by the surgeon's eye gaze. To provide the primary and secondary images, the imaging systems may use a single imaging module and post-imaging manipulation (e.g., digital manipulation) to provide the adjusted images. Alternatively or additionally, as described below in various embodiments, an imaging system includes a plurality of imaging modules. The plurality of imaging modules may be provided on a common instrument deployed through a single patient orifice or may be provided on multiple instruments deployed through multiple patient orifices. In some embodiments, the imaging system may include a rigid scope (i.e., having a rigid shaft) for which pose (e.g., position, orientation, roll) is determined by the movement of the particular camera or instrument arm on which it is mounted. In other embodiments, the imaging device 112 may additionally or alternatively include integrated articulation capabilities.

FIG. 6A illustrates an exemplary imaging system 112a that can be used as the imaging device 112 in the teleoperational assembly 100 of FIG. 1B. The imaging system 112a includes two imaging modules 714, 715 as components of a single imaging device. The imaging modules 714, 715 may be controlled independently of each other to create a primary image and a secondary image, such as a magnified image overlay, of a region of interest showing different information or views of interest to the user. The imaging system 112a further includes an instrument interface 150d (e.g., coupled to the camera arm 108 shown in FIG. 1B), a shaft 152d connected to the interface 150d, groups of cables, rods, and/or optical fibers 710 and 711 passing through the shaft 152d, wrists (e.g., articulating sections) 712 and 713 connected to the shaft 152d, and the imaging modules 714 and 715 at the distal end of the imaging device 112a.

In some embodiments, the instrument interface 150d may receive instructions from the control unit 210 shown in FIG. 2C. Each or both of the imaging modules 714, 715 may include optics and mechanics to illuminate a surgical area. In some embodiments, the imaging module 714 and/or the imaging module 715 may also include a device that can capture an image (e.g., a stereo image) of a surgical area. In some embodiments, the imaging device comprises a stereoscopic camera.

Figure 4:
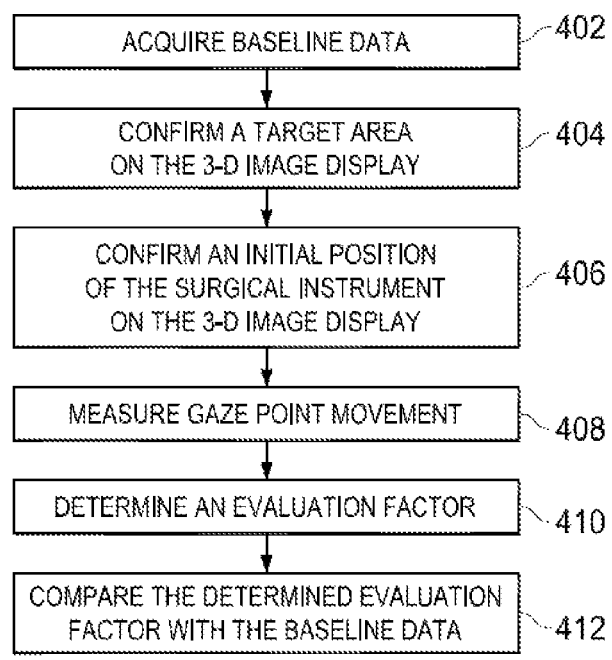
FIG. 4 illustrates an exemplary method for evaluating a surgeon's performance during a surgery using the eye tracking unit of FIG. 2B according to one embodiment of the present disclosure.

The image of the surgical area of interest can be captured by the auxiliary imaging module 715, and the adjusted image can be displayed on a display (e.g., the image displays 202a, 202b, the gaze point display 207 shown in FIG. 2C, and/or a display 416 shown in FIG. 4).

As shown in FIG. 6A, the shaft 152d of the imaging device 112a is configured to hold cables, rods and/or optical fibers 710 and 711. In some embodiments, a first group of cables, rods and/or optical fibers 710 may be coupled to the imaging module 714 through the wrist 712, and a second group of cables, rods and/or optical fibers 711 may be coupled to the imaging module 715 through the wrist 713. Such a configuration can provide independent control and manipulation between the imaging modules 714 and 715 by providing different instructions via the two different sets 710, 711 of cables, rods and/or optical fibers and by controlling the wrists 712, 713 with different motion controls. The wrists 712, 713 are connected to the shaft 152d at a distal end 716 of the shaft 152d, and coupled to the imaging modules 714, 715, respectively. The wrist 712 allows for movement of the imaging module 714 in at least two degrees of freedom and may be controlled with the first set of cables or rods 710 that passes through the shaft 152d. Similarly, the wrist 713 allows for movement of the imaging module 715 in at least two degrees of freedom and may be controlled with the second set of cables or rods 711 that pass through the shaft 152d. The optical fibers 710, 711 may be coupled to the optics of the imaging modules 714, 715 to both provide illumination and transmit the images.

In some embodiments, the instrument interface 150d couples actuation motors in the camera arm 108 to the cables and rods 710 and 711 respectively in shaft 152d. In some embodiments, the instrument interface 150d may include mechanisms that can be driven by an actuation motor in the camera arm 108 to control the wrist 712 and the wrist 713 to manipulate the imaging modules 714 and 715, respectively. For example, in one embodiment, when the imaging module 714 is used as the primary imaging module and the imaging module 715 is used as the auxiliary or secondary imaging module, the instrument interface 150d may send instructions to the actuation motor so that the auxiliary imaging module 715 may be driven by the actuation motor to move the imaging module 715 to the surgeon's gaze point (e.g., based on the detected gaze point relative to the image displays 202a, 202b as described above in relation to FIGS. 2B and 2C).

The imaging module 714 and/or the imaging module 715 can adjust the type of image obtained by the imaging device. For example, in one embodiment, the imaging modules 714, 715 can "zoom" into or out of a surgical area to obtain more detailed and less detailed images of the surgical area. In some embodiments, the imaging modules 714, 715 can change position along a longitudinal axis LA of shaft 152d relative to the distal end 716, thereby providing a physical, distance-based zoom function. The imaging module 714 and/or imaging module 715 can also be reoriented in multiple dimensions (e.g., within a spherical space) by manipulating the wrists 712, 713, respectively. Software operating in the teleoperational medical system 10 may control the zoom feature by controlling the physical position and orientation of the wrists 712, 713 and/or the imaging modules 714, 715, or by controlling digital manipulation of the images obtained by the imaging modules 714, 715 (e.g., through digital magnification or image adjustment). Additionally or alternatively, the zoom feature may be controlled by the imaging module 714 and/or imaging module 715 themselves.

FIG. 6B illustrates an imaging system 112b including an imaging device 112c and an imaging device 112d. In one embodiment, the imaging devices 112c, 112d may be used with two separate camera arms 108 of the teleoperational assembly 100 shown in FIG. 1B, with each imaging device 112c, 112d attached to an independent camera arm 108a, 108b, respectively. In the pictured embodiment, the imaging devices 112c, 112d each include an independent imaging module 720, 722, respectively. For example, in the pictured embodiment, the imaging module 720 is mounted at a distal end of the imaging device 112d, and the imaging module 722 is mounted at a distal end of imaging device 112c. The imaging devices 112c, 112d may be closely aligned with one another within the surgical field to assist with registration of both independently acquired images from the imaging modules 720, 722 to a single display (i.e., the display 416 shown in FIG. 4). The imaging devices 112c, 112d are substantially similar to the imaging module 112a described above in relation to FIG. 6B except for the differences described herein. For example, the imaging device 112d includes an instrument interface 150e, a shaft 152e connected to the interface 150e, a wrist 324 connected to the shaft 152e, the imaging module 720 connected to the wrist 724, and cables, rods and/or optical fibers 726 passing through the shaft 152e. Similarly, the imaging device 112c includes an instrument interface 150f, a shaft 152f connected to the interface 150f, a wrist 727 connected to the shaft 152f, the imaging module 722 connected to the wrist 727, and cables, rods and/or optical fibers 728 passing through the shaft 152f. The functions of the components of imaging device 112c and/or imaging device 112d are substantially similar to the corresponding components of imaging device 112a as described above.

Figure 6C:
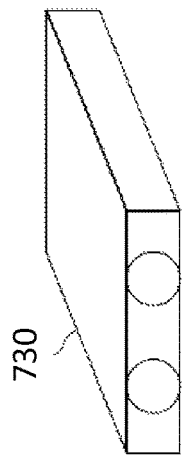
FIG. 6C is a schematic drawing of a stereo camera that can be used as imaging module of the endoscope of FIGS. 6A-6B according to an embodiment of the present disclosure.

FIG. 6C is a schematic drawing of a stereo camera 730 according to one embodiment of the present disclosure. The stereo camera 730 may be used as any of the above described imaging modules, including the imaging modules 714, 715 of FIG. 6A and the imaging modules 720, 722 of FIG. 6C. The stereo camera 330 can be used to capture stereo images that can be displayed to and perceived by human left and right eyes to be a 3D image.

The imaging modules (e.g., the imaging modules 714, 715, 720, and 722) can be independently moved in 3D space to provide different images of a surgical area. For example, the imaging module 714 of the imaging device 112a and/or the imaging module 720 of imaging device 112b can be used for providing a primary image of a surgical area. The imaging module 715 of the imaging device 112a and/or the imaging module 722 of the imaging device 112c can be used for providing a secondary or adjusted image, such as a magnified image of the surgical area corresponding to a surgeon's current gaze point, which is shown as an image 960 in FIG. 8C. In some examples, the imaging module 715 and an endoscope effector 732 may also be used for providing other imaging modalities, such as fluorescence or ultrasonic imaging, which can be used to identify and/or highlight structures within the magnified imaging region. In some embodiments, as described in further detail below, the imaging module 715 of the imaging device 112a and/or the imaging module 722 of the imaging device 112c can be used to capture images of different regions arranged in a non-overlapping fashion as the surgeon's gaze point scans across an area (e.g., a patient's abdominal cavity) to identify a region of interest (e.g., a lesion). The image corresponding to the region of interest may be further magnified or processed with other imaging modalities (e.g., by optical manipulation and/or digital processing).

The teleoperational medical system 10, including the eye tracking system 200 and one or more imaging devices 112, can be used to apply various image modifications to a gaze region and a non-gaze region of the surgeon. For example, the image modifications may include any of variety of imaging effects, including without limitation, magnification, zooming in or out, highlighting, recolorizing, decolorizing, labeling, brightening, blurring, and sharpening. In some embodiments, the image modification may highlight or change the gaze region while deemphasizing the non-gaze region. For example, in some embodiments, the image modification may comprise defocusing, decolorizing, or blurring the non-gaze region to highlight the gaze region by contrast. In some embodiments, the image modifications include magnification of a gaze region of the surgeon in response to the surgeon's instruction. In some embodiments, the image modifications include overlaying a magnified gaze region of the surgeon over a primary view of the surgical site. In some embodiments, the image modifications include applying various image modalities to the gaze region of the surgeon. In some embodiments, the teleoperational medical system 10 requires additional user input (in addition to user eye gaze) to initiate the image modifications. In some embodiments, the teleoperational system and the eye tracking system 200 interpret the user eye gaze to determine which imaging device obtains the primary image and which imaging device obtains or creates the auxiliary or secondary image.

Figure 7A:
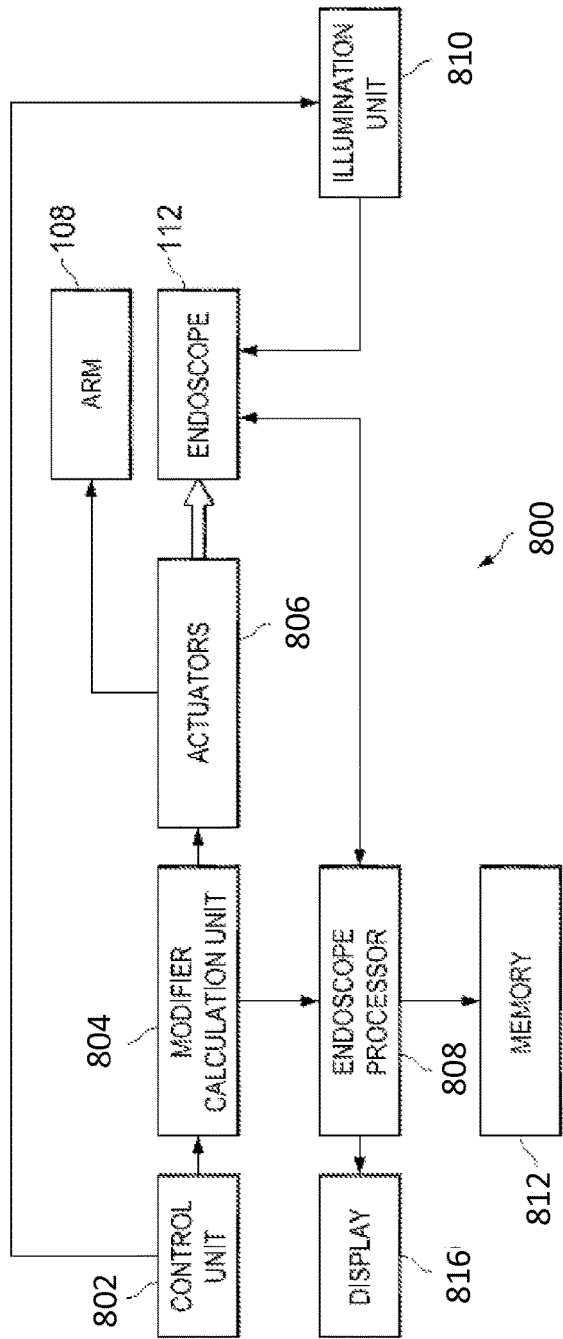
FIG. 7A illustrates a block diagram of an endoscope system according to one embodiment of the present disclosure. The endoscope system incorporates the exemplary endoscope shown in FIGS. 6A-6B.

FIG. 7A illustrates a block diagram of an image processing system 800 that can be incorporated with any of the imaging devices 112a, 112b, 112c, 112d shown in FIGS. 6A-6B to realize the desired image modifications. The image processing system 800 includes a control unit 802 that may be the same as the control unit 210 shown in FIG. 2C. The control unit 802 may include one or more processors to process input data and issue commands. The processors may be coupled with a memory (volatile, nonvolatile, or a combination) to retain data and programming instructions. The control unit 802 may receive instruction signals from the eye gaze processor 206 shown in FIG. 2C. The control unit 802 may also receive instructions in other forms of input, such as input signals from the control interfaces 122 shown in FIG. 1C. The programming instructions may include instructions to translate data signals received from, for example, the eye gaze processor 206, into command signals that represent the requested modification of the original image produced by the imaging device 112. Using those signals, the control unit 802 can determine the type and/or extent of image change the surgeon intends. For example, the control unit 802 can determine whether the surgeon requests a zoom or magnification function or whether the surgeon requests a different imaging modality display. In some embodiments, the control unit 802 may receive instructions to apply different image modifications to the region corresponding to the surgeon's gaze point (i.e., the gaze region) and the remainder of the image field (i.e., the non-gaze region).

After receiving instructions, the control unit 802 may send signals to a modifier calculation unit 804. In some embodiments, the modifier calculation unit may also be known as an endoscope manipulation calculation unit. In some embodiments, the modifier calculation unit 804 may be included in the instrument interface 150 (e.g., 150d, 150e, 150f) of the imaging device 112 (e.g., 112a, 112b, 112c, 112d). The modifier calculation unit 804 may include a processor to translate the signals received from the control unit 802 into command or action signals. In some embodiments, the command signals are directly processed by an endoscope processor to digitally alter the image as instructed by the command signals. Additionally or alternatively, the command signals may be transmitted to actuators 806 that are able to affect the motion of the imaging device 112. In some embodiments, the surgeon's intended image modification (e.g., magnification, zooming in, or zooming out) may be realized when the actuators 806 cause the corresponding motion of the appropriate endoscope or imaging module. The modifier calculation unit 804 may include one or more processors coupled to memories (volatile, nonvolatile, or a combination) that hold data and programming (e.g., gaze point data, motion-related command data, gaze point tracking algorithms, image modification algorithms). In some embodiments, the above-described functions of the control unit 802, the modifier calculation unit 804, and/or the endoscope processor 808 may be performed by a single processor.

The actuators 806 can be mechanically coupled to the instrument interface 150 of the imaging device 112. For example, the actuators 806 can be mechanically coupled to the instrument interface 150d of the imaging device 112a shown in FIG. 6A. The actuators 806 can, for example, be rotary motors housed in the camera arm 108 (e.g., camera arm 108, 108a, and/or 108b) of the teleoperational assembly 100, on which the corresponding imaging device 112 is attached. As discussed above, in some embodiments, the modifier calculation unit 804 of the instrument interface 150 may translate the mechanical inputs of actuators 806 into movement of the corresponding wrists and imaging modules of the imaging devices.

The control unit 802 can also control the light output of an illumination unit 810. The illumination unit 810 may provide light through one or more optical fibers, such as the optical fibers 710 and/or the optical fibers 711 of the imaging device 112a in FIG. 6A, and the optical fibers 726 in the imaging device 112d, and the optical fibers 728 in the imaging device 112c in FIG. 6B, in order to illuminate a surgical area.

The image processing system 800 may include a plurality of endoscope processors 808, each configured to perform image capturing, image processing, and/or image displaying functions for a corresponding imaging module, such as the imaging modules 714, 715, 720, or 722. The endoscope processor 808 may be located at the vision cart 140, for example, as part of the central electronic data processing unit 142. The endoscope processor 808 may also be located at the teleoperational assembly 100 and/or the surgeon console 120. The endoscope processor 808 may be coupled to memories (volatile, nonvolatile, or a combination) that hold data and programming.

The image processed by the endoscope processor 808 may be output onto a display 816 shown in FIG. 4A. In some embodiments, the display 816 may comprise the image display 202a, the image display 202b, and/or the gaze point display 207 of the eye tracking system 200 as shown in FIG. 2C. In some embodiments, the display 816 is the touch screen monitor 146 mounted on the vision cart 140 shown in FIG. 1D. In some embodiments, the display 816 can show a secondary or modified image overlaying the primary image, for example, displayed on displays 202a and 202b at the surgeon console 120. In some embodiments, the display 816 can show a plurality of images (e.g., the primary image and the modified image) displayed side-by-side in an overlapping or a non-overlapping fashion.

The imaging modules, for example, the imaging module 714, 715, 720, or 722, may comprise stereoscopic cameras which can capture stereo images of the surgical area. The stereo images of the surgical area may be transported by optical fibers, such as the optical fibers 710, 711, 726, or 728, to the endoscope processor 808. The endoscope processor 808 can digitize the stereo images captured by the imaging module, and provide the stereo images onto the display 816. The displayed stereo images on the display 816 can be perceived by the surgeon through the eye tracking system 200 (shown in FIG. 2C) as a 3D stereo image. The surgeon's instructions may be recognized and initiated using the surgeon's eye gaze data captured by the eye trackers 204a, 204b. The eye gaze processor 206 can process these instructions and communicate them to the control unit 802. The eye trackers 204a, 204b and the eye gaze processor 206 may be able to capture and generate an image of the 3D eye gaze of the surgeon, as discussed in detail above with respect to FIGS. 2A-2C.

With respect to FIG. 6A, in some embodiments, when the imaging device 112a is used in the teleoperational medical system 10, the two imaging modules 714, 715 may share the same instrument interface 150d. As described above, in some embodiments, the imaging module 714 is used for capturing a primary image of the surgical area, and the imaging module 715 is used for capturing a secondary (e.g., modified) image based on the surgeon's instructions. While the imaging module 714 captures a primary image of the surgical site, the eye gaze processor 206 may interpret and send the surgeon's instructions to the control unit 802 to instruct the imaging module 715 to capture and display an adjusted image (e.g., by way of non-limiting example, a magnified image, a sharpened image, a colorized image, a decolorized image) of a region in the surgical field corresponding to the surgeon's eye gaze point. The instructions may be processed by one or more processors of the control unit 802 and the modifier calculation unit 804.

In some embodiments, the resultant command signals are sent to the endoscope processor 808 to digitally affect (e.g., digitally magnify or otherwise modify) the images received by the imaging modules 714, 715. In some embodiments, the resultant command signals are sent to the endoscope processor 408 to alter the imaging mode of the imaging module 715 (e.g., by way of non-limiting example, to change the imaged wavelength range, the optical magnification, or the width of the field of view). In some embodiments, the resultant command signals may be sent via the cables, rods or optic fibers 711 to control the motion of imaging module 715, and the imaging module 715 may move or adjust based on the surgeon's instructions. For example, when the surgeon desires to view a magnified image of a region identified by his or her gaze point, the imaging module 715 may shift along the longitudinal axis LA of the shaft 152d to acquire the "zoomed in" or magnified image. In some embodiments, the imaging module 715 may be controlled to capture and display a primary image of the surgical area, and the imaging module 714 may capture and display a secondary image based on the surgeon's instructions. The secondary image may comprise a visually adjusted portion of the primary image.

In some embodiments, as shown in FIG. 6B, the imaging device 112b and the imaging device 112c may be used in the teleoperational medical system 10. As shown in FIG. 6B, the imaging device 112b includes the instrument interface 150d, and the imaging device 112c includes the instrument interface 150f. In some embodiments, there may be more than one control unit 802, with each control unit 402 coupled to one of the instrument interfaces 150d and 150f. In alternative embodiments, there may be one control unit 802 that is coupled to both instrument interfaces 150d, 150f, and that is capable of sending independent instructions to the instrument interfaces 150d, 150f. For example, in some embodiment, the imaging device 112b may be used for capturing a primary image of the surgical area based on the instructions received by the instrument interface 150d, and the imaging device 112c may be used for capturing a secondary or modified image based on the instructions received by instrument interface 150f.

In one embodiment, while the imaging module 620 captures a primary image of the surgical site, the eye gaze processor 206 may interpret and send the surgeon's instructions to the control unit 802 to instruct the imaging module 722 to capture and display an adjusted image (e.g., by way of non-limiting example, a magnified image, a sharpened image, a colorized image, a decolorized image) of a region in the surgical field corresponding to the surgeon's eye gaze point. The instructions may be processed by one or more processors of the control unit 802 and the modifier calculation unit 804.

In some embodiments, the resultant command signals are sent to the endoscope processor 808 to digitally affect (e.g., digitally magnify or otherwise modify) the images received by the imaging modules 720, 722. In some embodiments, the resultant command signals are sent to the endoscope processor 708 to alter the imaging mode of the imaging module 722 (e.g., by way of non-limiting example, to change the imaged wavelength range, the optical magnification, or the width of the field of view). In some embodiments, the resultant command signals may be sent via the cables, rods or optic fibers 728 to control the motion of imaging module 722, and the imaging module 722 may move or adjust based on the surgeon's instructions. For example, when the surgeon desires to view a magnified image of a region identified by his or her gaze point, the imaging module 722 may shift along a longitudinal axis of the shaft 152f to acquire the "zoomed in" or magnified image. In alternative embodiments, the imaging module 722 may be controlled to capture and display a primary image of the surgical area, and the imaging module 720 may capture and display a secondary image based on the surgeon's instructions.

Figure 7B:
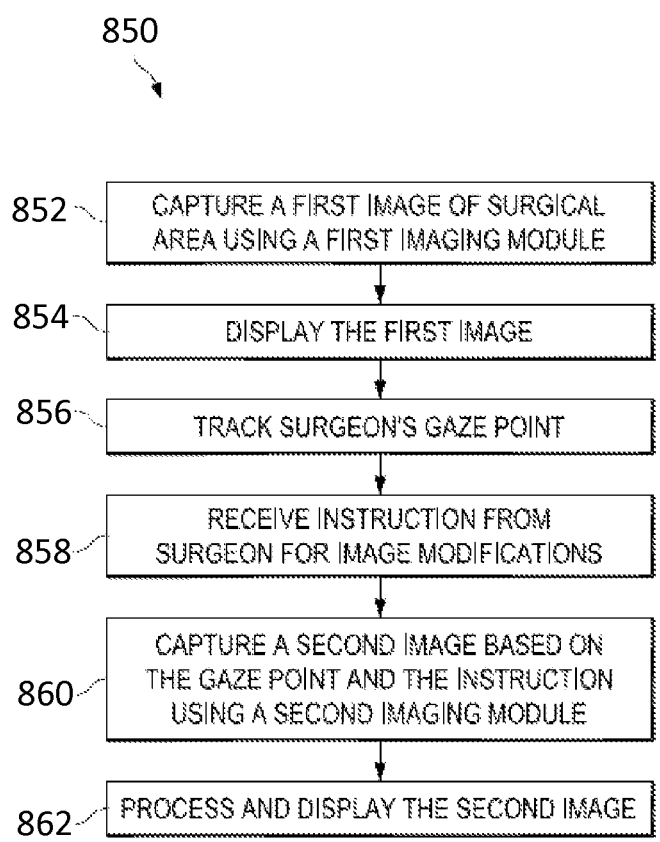
FIG. 7B is a flowchart illustrating a method for using the teleoperational medical system to apply image modifications according to an embodiment of the present disclosure.

FIG. 7B is a flowchart illustrating a method 850 for controlling the imaging device(s) of the teleoperational medical system 10 to apply various imaging modifications according to an embodiment of the present disclosure. At process 852, a first imaging module captures a first or primary image of a surgical area. The first imaging module may be a stereoscopic camera configured to capture stereo images of the surgical area. The location within the surgical field at which the first imaging module focuses may be adjusted by persons other than the user, for example, personnel in the operating room next to a patient. Additionally or alternatively, the first imaging module may be actuated and controlled by the surgeon at a surgeon console 120 (as shown in FIG. 1C) or other component of the teleoperational medical system 10. In some embodiments, as described above in relation to FIGS. 2A-2C, the first imaging module can be controlled by the gaze point of the surgeon. In particular, the gaze point of the surgeon can be tracked and interpreted by the eye tracking system 200 shown in FIG. 2C to affect the first imaging module. In some embodiments, the first image is an overview image of a surgical area, such as patient's abdomen, at zero or low magnification. In some embodiments, the first image comprises a primary image of a surgical area (e.g., the surgical area where the surgeon is working) at zero or low magnification.

At process 854 of method 850, the first image is processed for display by the endoscope processor 808 shown in FIG. 7A, which is coupled to the first imaging module. The endoscope processor 808 receives data representative of the first image and digitizes various characteristics of the image data, such as the location, boundary, and/or magnification of the first image. The digitized information may be saved in one or more memories coupled to the endoscope processor 808. The endoscope processor 808 processes the imaging information of the first image and displays the first image onto the display 816 shown in FIG. 7A. When the first imaging module is a stereoscopic camera, the first image is a stereo image. The stereo image can be displayed onto the left and right eye image displays 202a, 202b of the surgeon console 120. A 3D primary image of the surgical area can then be viewed by the surgeon.

At process 856, the eye tracking system 200 tracks the surgeon's eye gaze point relative to the display of the first image. For example, when the first image is displayed on the left and right eye image displays 202a, 202b, the eye tracking system of FIG. 2C may determine the surgeon's eye gaze relative to the first image. The eye gaze processor 206 may digitize the eye gaze information to provide, for example, a 3D location of the surgeon's gaze point. The digitized information may be saved in the one or more memories 208 (shown in FIG. 2C) coupled to the eye gaze processor 206. As the surgeon sends instructions through the surgeon's eye gaze, the eye gaze processor 206 can provide the digitized information to the control unit 210. Additional details on devices, systems, and methods for control of a teleoperational medical system by eye gaze tracking may be found, for example, in U.S. Provisional Application No. 61/955,334, entitled "MEDICAL DEVICES, SYSTEMS, AND METHODS INTEGRATING EYE GAZE TRACKING FOR STEREO VIEWER," and filed Mar. 19, 2014, which is incorporated herein in its entirety.

At process 858, the teleoperational medical system 10 receives instruction from the surgeon to provide various image modifications. In some embodiments, the instruction from the surgeon includes providing a magnified image of a gaze area of the surgeon. In some embodiments, the instruction from the surgeon also includes overlaying a second, modified image on the first image. The instruction from the surgeon may also include displaying a second image in any suitable imaging modality.

At process 860, the teleoperational medical system 10 captures the second image based on the instruction received at process 858 and the gaze point of the surgeon tracked at process 856. In some embodiments, the second image may be captured by a second imaging module using the instruction and the gaze point information received by the control unit 210. In some embodiments, the position and orientation of the second imaging module can be adjusted accordingly by the image processing system 800 shown in FIG. 7A to capture the second image. In other embodiments, the desired second image is obtained through digital processing without optical manipulation of the second imaging module. In some embodiments, both optical and digital manipulations are used to achieve the desired second image.

At process 862, the second image is displayed on display 816 shown in FIG. 7A. For example, the second image can be a magnified image of a gaze point of the surgeon, or an image displayed in a different imaging modality as requested by the surgeon.

Figure 8A:
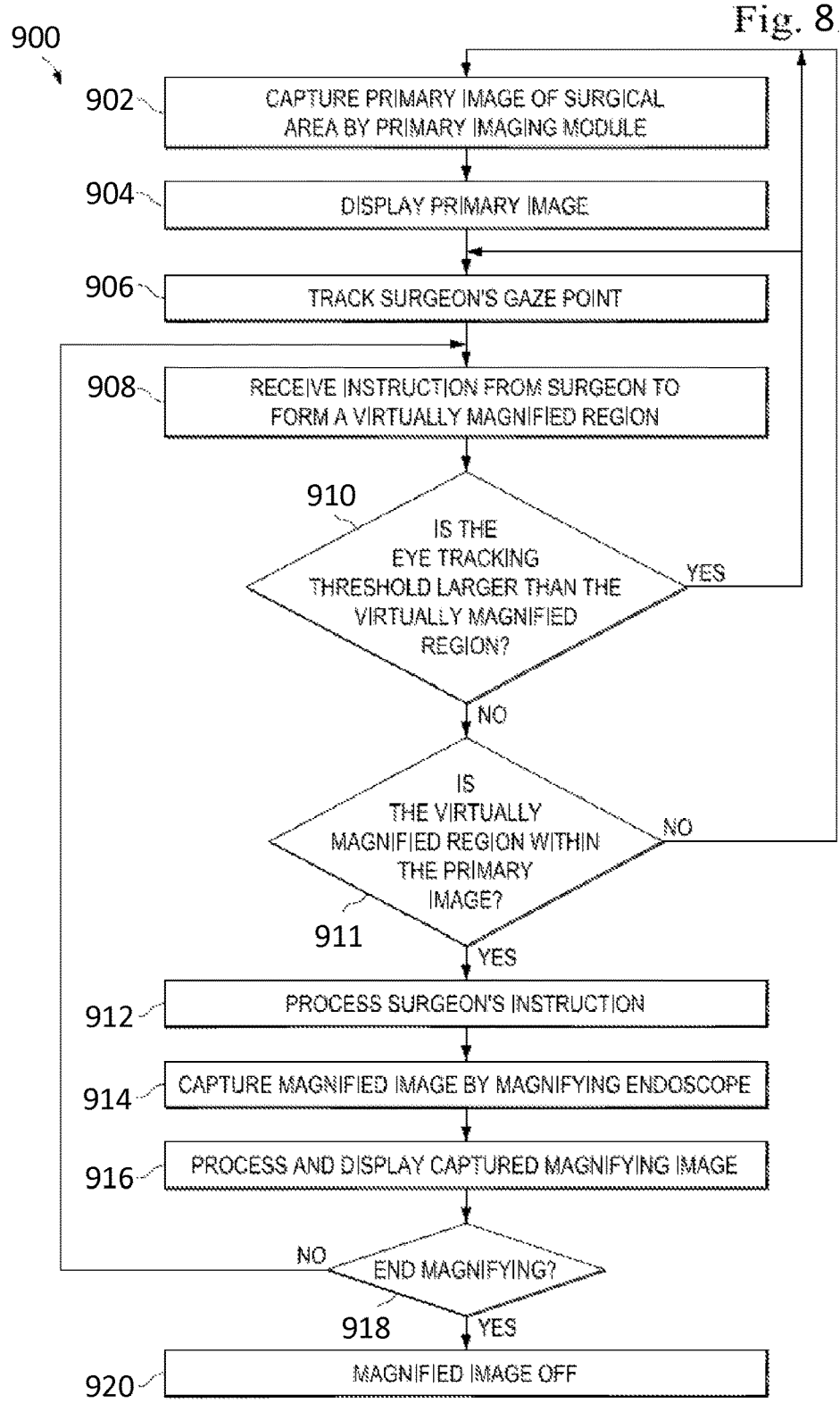
FIG. 8A is a flowchart illustrating a method for controlling one or more endoscopes of the teleoperational medical system using the endoscope system to display a magnified image overlaying a primary image according to an embodiment of the present disclosure.
Figure 9:
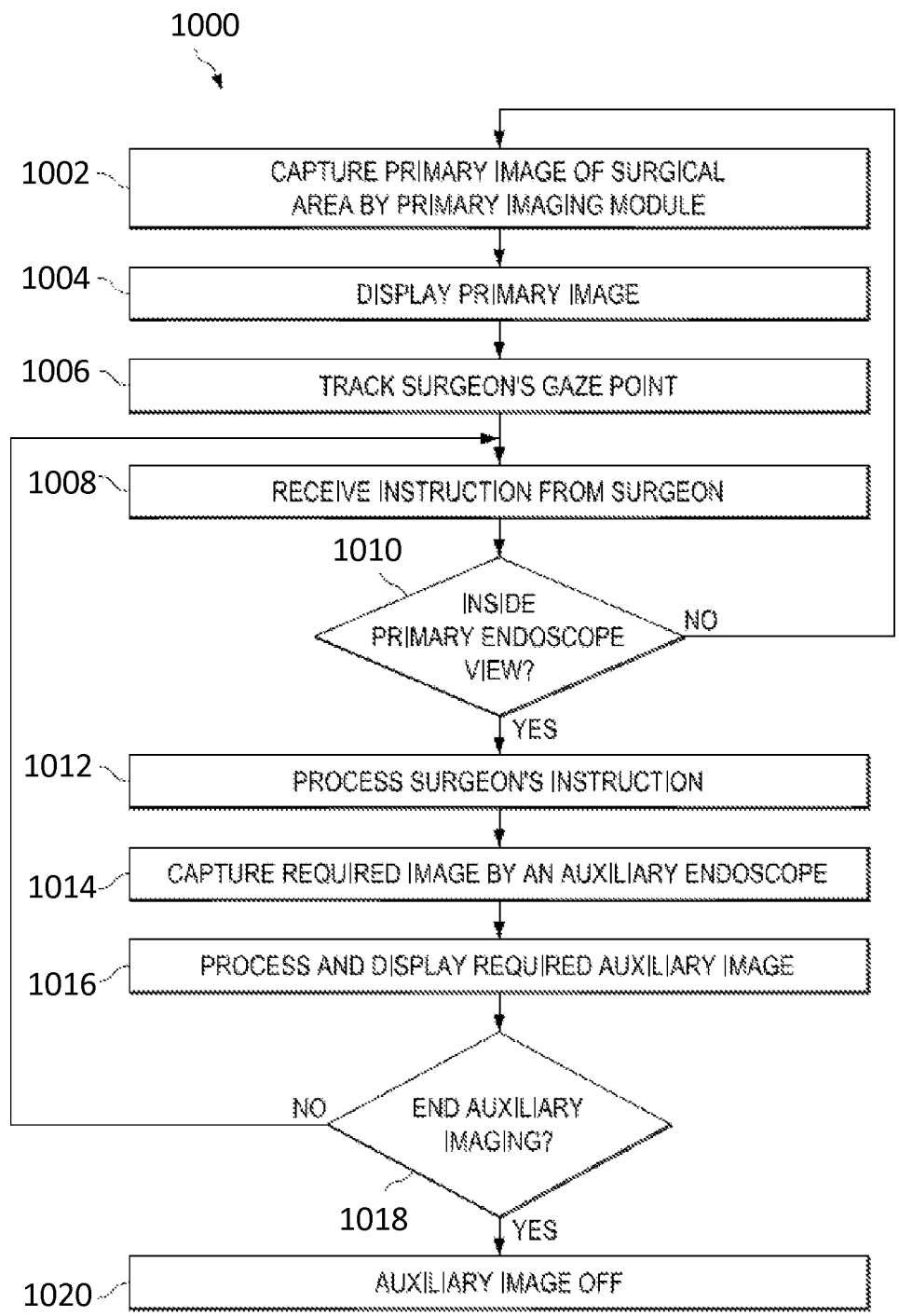
FIG. 9 is a flowchart illustrating a method for controlling one or more endoscopes of the teleoperational medical system using a control system to capture and display different imaging modalities according to an embodiment of the present disclosure.
Figure 10A:
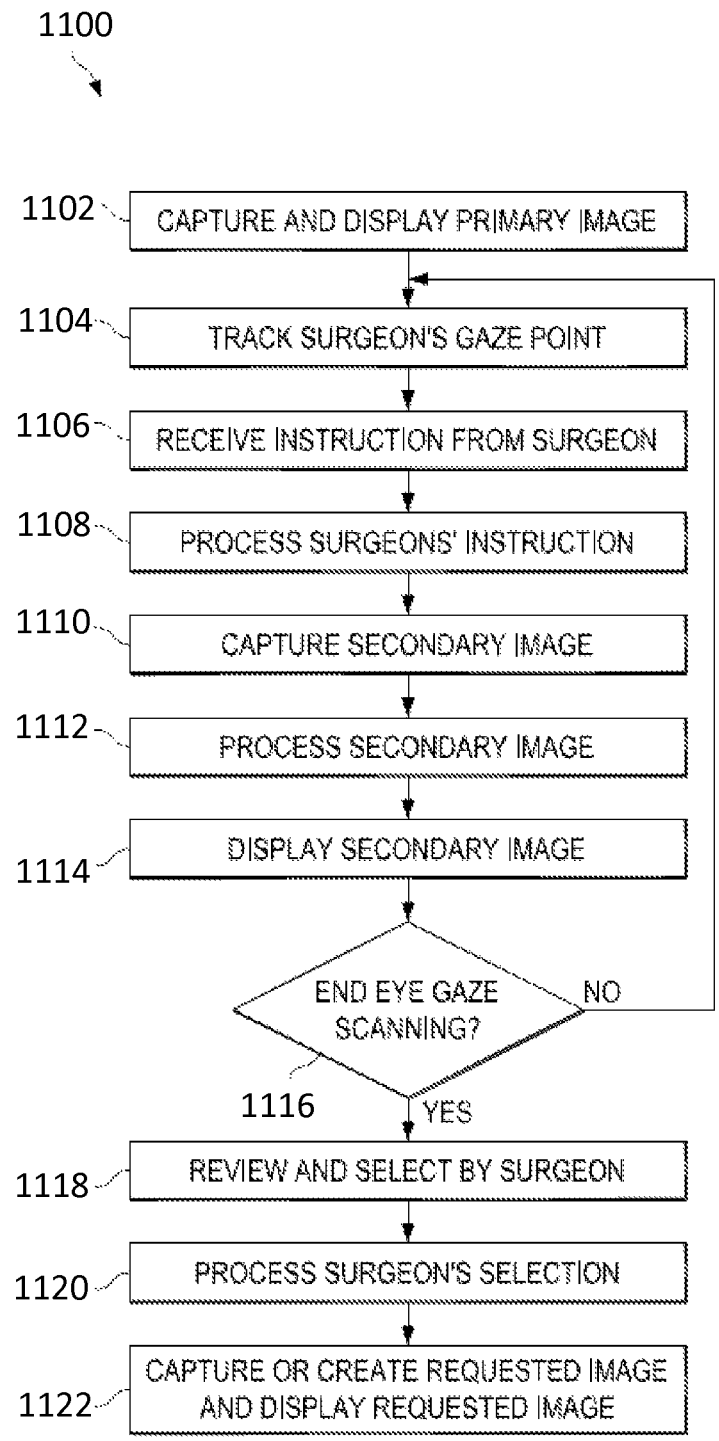
FIG. 10A is a flow chart illustrating a method for displaying a plurality of images captured as an endoscope following the surgeon's eye gaze scanning across a primary image on a display according to an embodiment of the present disclosure.

FIGS. 8A, 9, and 10A are flowcharts illustrating various methods 900, 1000, and 1100 demonstrating different image modifications that can be achieved using the teleoperational medical system 10. It is to be understood that these methods are merely exemplary in nature and are not intended to be limiting. Other image modifications are contemplated.

Figure 8B:
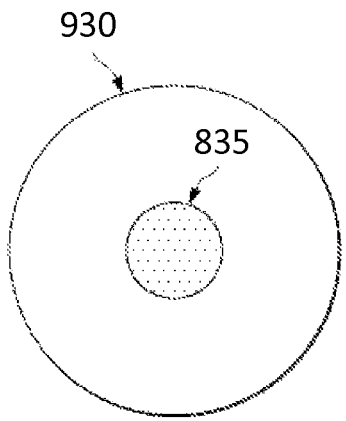
FIG. 8B illustrates a predetermined eye tracking accuracy threshold displayed within a virtually magnified region according to an embodiment of the present disclosure.
Figure 8C:
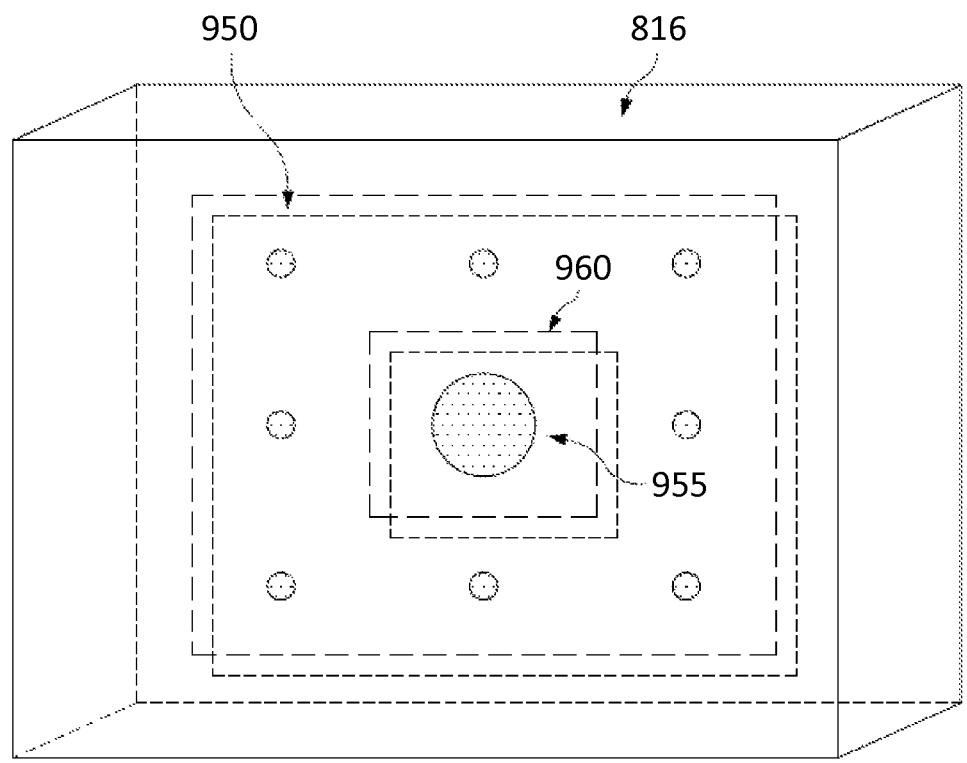
FIG. 8C illustrates an example of displaying a magnified image overlaying a primary image according to an embodiment of the present disclosure.
Figure 8D:
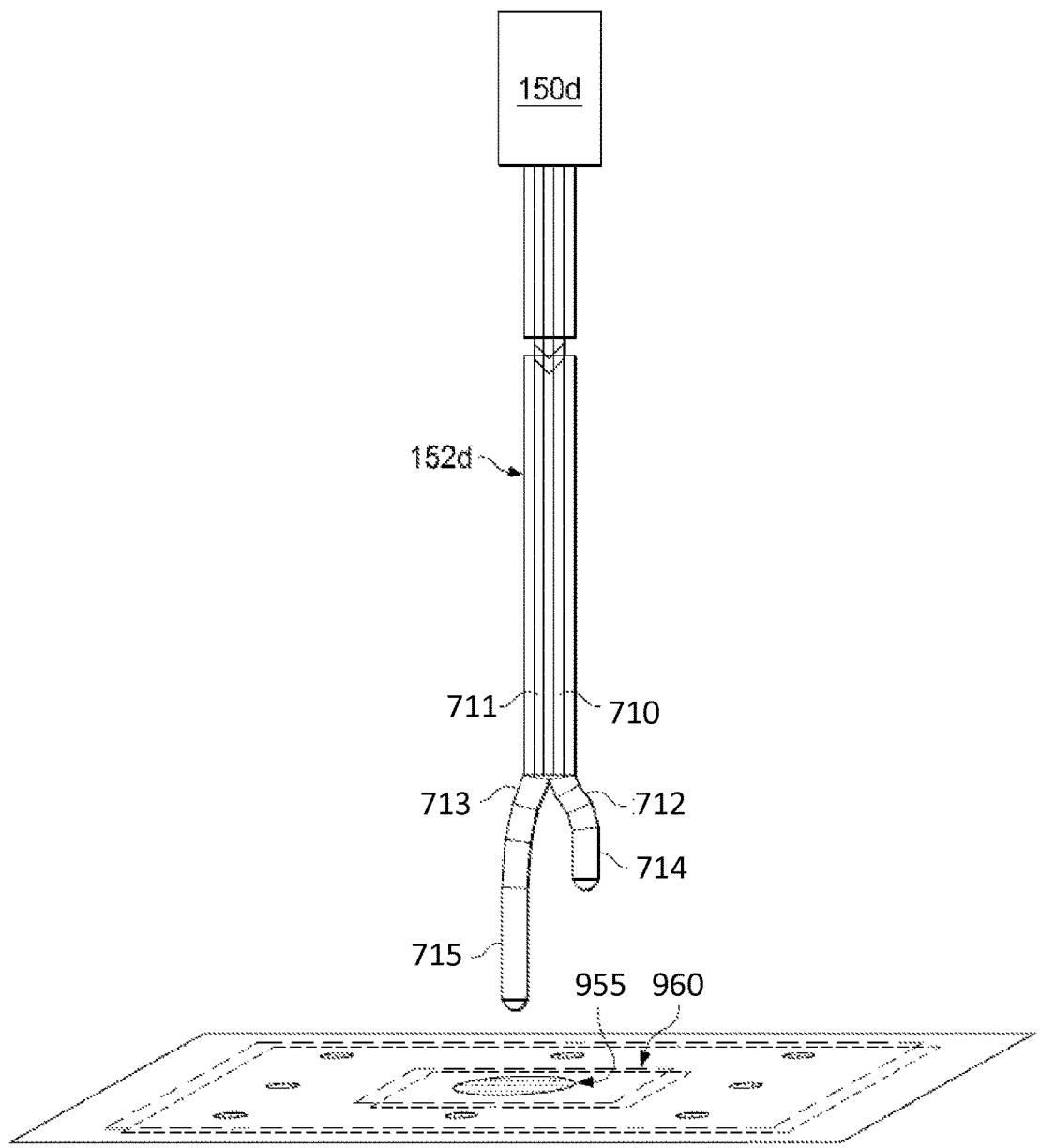
FIG. 8D is a schematic drawing illustrating using an endoscope of FIG. 6A to capture and generate a primary image and a magnified image as shown FIG. 8C according to an embodiment of the present disclosure.
Figure 8E:
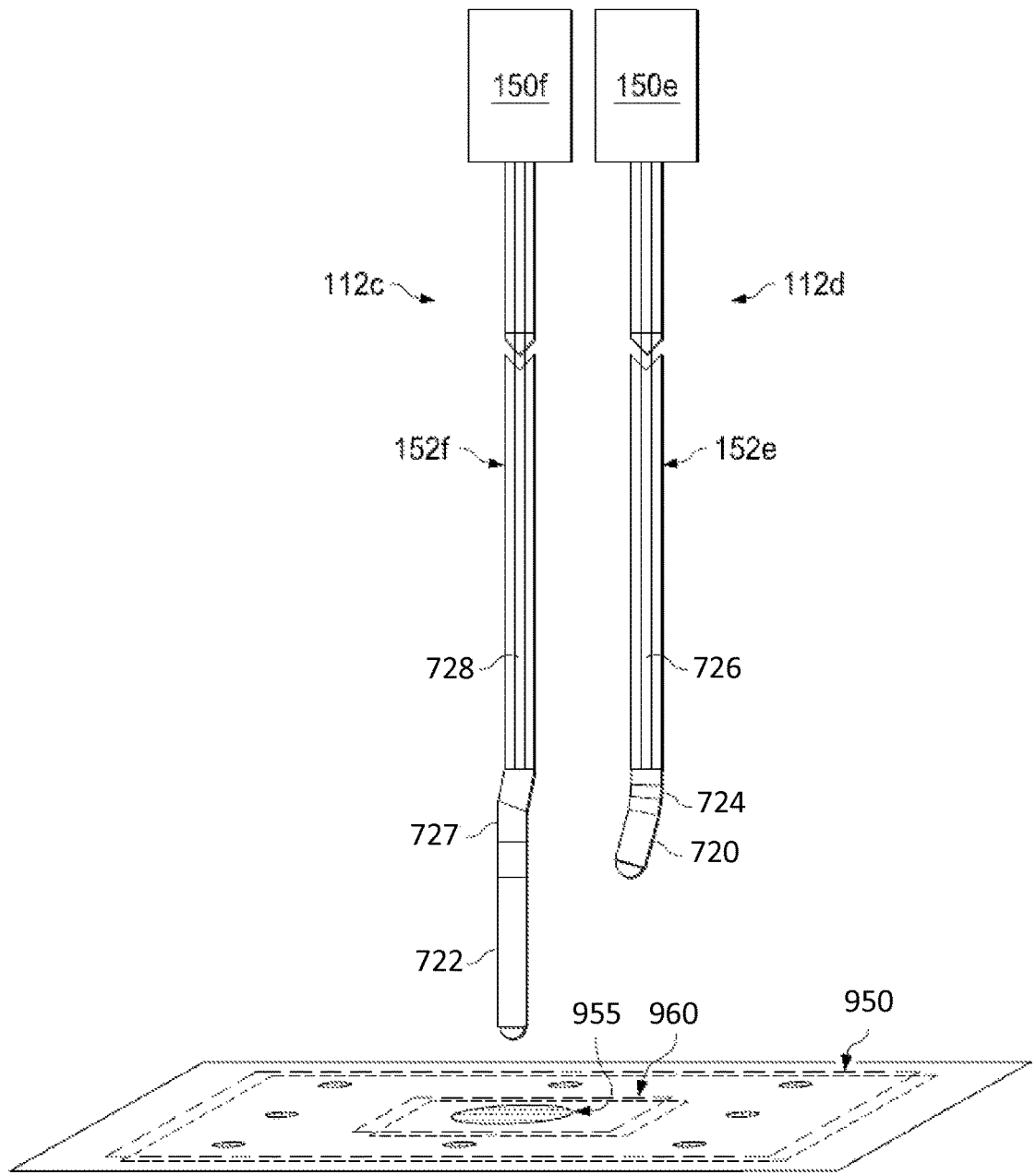
FIG. 8E is a schematic drawing illustrating using two endoscopes of FIG. 6B to capture and generate a primary image and a magnified image as shown in FIG. 8C according to an embodiment of the present disclosure.

FIG. 8A is a flowchart illustrating the method 900 for displaying a magnified image overlaying a primary image using the teleoperational medical system 10 of the present disclosure. In particular, method 900 is directed to the capture and display of a primary image using a primary imaging module, and to the capture and display of a magnified image of a region corresponding to the surgeon's gaze point using an auxiliary imaging module. FIG. 8B illustrates a predetermined eye tracking threshold region 935 displayed within a magnified region 930 according to some embodiments of the present disclosure. FIG. 8C illustrates an example of displaying a magnified image 960 on top of the primary image 950. FIG. 8D is a schematic drawing illustrating the use of the imaging device 112a of FIG. 6A to capture and generate the primary image 950 and the magnified image 960 shown FIG. 8C. FIG. 8E is a schematic drawing illustrating the use of the imaging devices 112b and 112c of FIG. 6B to capture and generate the primary image 950 and the magnified image 960 shown in FIG. 8C. FIGS. 8A-8E describe the auxiliary or secondary image as a magnified image for the sake of simplicity, and it is to be understood that other imaging effects are contemplated (such as, by way of non-limiting example, color/grayscale imaging, sharp/blurred imaging, and bright/dull imaging).

The method 900 is described below with reference to FIGS. 8A and 8C-8E. At process 902, the primary image 950 of a surgical area is captured by the primary imaging module 714 of FIG. 8D or the primary imaging module 720 of FIG. 8E. In some embodiments, the primary imaging module may be the first imaging module discussed in process 952 of method 950 shown in FIG. 8B.

At process 904 of method 900, the captured primary image 950 is processed by the endoscope processor 908, which is coupled to the primary imaging module 714 or the primary imaging module 720, and the primary image is displayed on the display 816.

At process 906, the eye tracking system 200 of FIG. 2C tracks and interprets the surgeon's eye gaze point. The eye gaze information may include a 3D location of the surgeon's gaze point. The eye gaze information can be provided to the control unit 210 as discussed with reference to process 956 in FIG. 8B.

In some embodiments, the surgeon may want to investigate a region of interest within a surgical area in greater detail. For example, the surgeon may wish to examine a magnified view of fine structures of a surgical area, such as nerves, blood vessels, and lesions. In some instances, the surgeon may also want to initiate a microsurgery application on top of or overlying the primary image 950. At process 908 of method 900, the teleoperational medical system 10 receives instruction from the surgeon to view a virtually magnified image of a region of interest. In some embodiments, the surgeon may use his or her eye gaze point to locate the region of interest, and input confirmation instructions using any of a variety of other input methods. For example, the surgeon may press a button at the surgeon console, tap a foot pedal, send an audio message, or wink. The confirmation instructions may be sent to the control unit 210 of the auxiliary imaging module, such as the imaging module 715 of FIG. 8D or the imaging module 722 of FIG. 8E. In some embodiments, the confirmation instructions also include more detailed information regarding the character or extent of the selected image modification. For example, in some embodiments, the confirmation instructions include information about the surgeon's preferred level of magnification. In addition, the location information about the surgeon's gaze point provided by the eye gaze processor 206 may also be sent to the control unit 210 coupled to the corresponding auxiliary imaging module.

As mentioned above, FIG. 8B illustrates the predetermined eye tracking threshold region 935 displayed within the virtually magnified region 930. The virtually magnified region 930 may be generated using the digitized location information about the surgeon's eye gaze (e.g., provided by the eye gaze processor 206), and the preferred level of magnification included in the surgeon's instructions (e.g., acquired at process 908). The predetermined eye tracking threshold region reflects the characteristic eye movement of the current user of the teleoperational medical system 10. In general, human eye movement may include frequent saccades, and the eye movement behavior varies from person to person. Thus, the eye tracking threshold region 935 comprises a region within which the surgeon's eye gaze frequently saccades and may correspond to the observed eye movement behavior of the surgeon. Because different surgeons may have different saccade frequencies, velocities, and amplitudes, the shape and size of the eye tracking threshold region 935 can vary from one surgeon to another. The eye tracking threshold region 935 of a particular surgeon may be decided during an eye tracking calibration process.

The predetermined eye tracking threshold region 935 of a surgeon may reflect the accuracy and precision range of the eye gaze measurement of this surgeon. In some embodiments, the eye tracking threshold region 935 may be used to verify the center location of the measured surgeon's eye gaze point as well as the consistency of repeated measurements at that point. The predetermined eye tracking threshold region 935 may be arranged to be co-centered with the magnified region 930 to facilitate the comparison between the eye tracking threshold region 935 and the magnified region 930.

It is to be understood that the circular shapes of magnified region 930 and the eye tracking threshold region 935 are merely exemplary for illustration in the present disclosure, and the regions 930, 935 may be shaped in any of a variety of suitable shapes, including, by way of non-limiting example, rectangular, elliptical, or square. In some embodiments, because the eye tracking threshold region 935 of a surgeon may change due to the accumulated stress or fatigue, the surgeon may undergo another calibration session to update the eye tracking threshold region 935. In some embodiments, the surgeon's eye movement behavior may be monitored in real time by the eye tracking system 200 to alert the surgeon and/or other healthcare personnel when any abnormal eye movement behavior of the surgeon is detected. For example, if the eye tracking system 200 detects abnormal and/or uncharacteristic eye movement behavior for the surgeon, a warning may be sent by the system 200 to the surgeon (e.g., via the display 816) requesting a recalibration process or the surgeon may be advised to halt the current working session.

At process 910 of method 900, the size of the predetermined eye tracking threshold region 935 of the surgeon (e.g., the current user) is compared to the size of the virtually magnified region 930 (e.g., by the image processing system 800 shown in FIG. 7A) in order to avoid inadvertent jittering in the magnified view. This comparison can be performed by the eye gaze processor 206 and/or the processors of the control unit 210. If the magnified region 930 is smaller than the predetermined eye tracking threshold region 935, the surgeon's current gaze point may not be within the desired range of accuracy and precision, and the magnified image 930 of the surgeon's current gaze point may be displayed with inadvertent jittering or saccade. In other words, if the surgeon's eye gaze point is located outside the predetermined eye tracking threshold 935, the surgical area represented by the magnified image 930 changes as the surgeon's eye gaze shifts with respect to the image display 816 shown in FIG. 7A (e.g., the image displays 202a, 202b shown in FIG. 2C). In some embodiments, the average point-of-gaze (e.g., a time-averaged weighting of the gaze point over a particular period of time or particular number N of image frames) can be computed by the gaze processor 206 and/or the processors of the control unit 210, and the average point-of-gaze may be compared to the predetermined eye tracking threshold region 935. For example, if the average point-of-gaze (e.g., over the last N image frames) moves outside of the predetermined eye tracking threshold region 935, then the location of the magnified region 930 shifts with respect to the image display 816 shown in FIG. 7A (e.g., the image displays 202a, 202b shown in FIG. 2C). Thus, the predetermined eye tracking threshold region 935 allows for the natural saccade or shifting of a user's eye gaze without causing inadvertent jittering of the location of the magnified view (e.g., without changing the magnified image 930 to track or reflect the natural saccade of the surgeon's eye gaze).

In some embodiments, if the surgeon's eye gaze point is located outside the predetermined eye tracking threshold 935, the current gaze point of the surgeon may not be magnified, and the method 900 returns to process 906 to continue tracking the surgeon's eye gaze. In some embodiments, if the surgeon wants to change the primary image by changing the focusing location of the primary imaging module, then the method 900 returns to process 902 to capture a different primary image.

However, if the magnified region 930 reflecting the surgeon's eye gaze is determined to be larger than the predetermined eye tracking threshold region 935 (e.g., by the image processing system 800 shown in FIG. 7A), the surgeon's current gaze point (e.g., measured by the eye tracking system 200) may be deemed within the desired range of accuracy and precision of the eye gaze measurement of the current surgeon. In other words, if the surgeon's gaze point is determined to lie within the predetermined eye tracking threshold 935, the magnified image 530 remains stationary. The magnified image 930 of the surgeon's current gaze point may be displayed (e.g., as the magnified region 930) without reflecting the inadvertent jittering or saccade of the eyes.

At process 911, the eye gaze processor 206 and/or the processors of the control unit 210 query whether the magnified region 930 lies within the primary image. In some examples, the surgeon's eye gaze may either intentionally or inadvertently shift to a region out of or at the edge of the primary image captured by primary imaging module 714 or primary imaging module 720. In general, it may be easier and more accurate to locate and control a user's magnified vision (e.g., the magnified region 930 of a region of interest) near the middle region of the primary image than out of or at the edge of the primary image. Thus, at process 911, the virtually magnified region 930 of the surgeon's eye gaze is further compared with the primary image 950 captured by the primary imaging module to confirm that the surgeon's eye gaze point lies within the primary image.

If the magnified region 930 lies out of or at the edge of the primary image 950, the method 900 may proceed back to the process 902 by adjusting the position and orientation of the primary imaging module and/or the auxiliary imaging module to acquire new primary and magnified images. In some instances, the primary imaging module may "follow" the movement or direction of the auxiliary imaging module within the surgical field. For example, the image processing system 800 shown in FIG. 7A may shift the auxiliary imaging module 715 or 722 (shown in FIGS. 8D and 8E, respectively) in coordination with the shifting of the surgeon's eye gaze point, and may shift the primary imaging module 714 or 720 (shown in FIGS. 8D and 8E, respectively) to "follow" the magnified region 930, thus maintaining the magnified region within a central portion of the primary image. In some embodiments, the digitized surgeon's eye gaze information may be used by the control unit 210 of the corresponding primary imaging module to appropriately adjust its position.

When the teleoperational medical system 10 (e.g., the image processing system 800 shown in FIG. 7A) determines that the virtually magnified region 930 of the surgeon's magnified eye gaze lies within primary image 950, the method 900 proceeds to process 912. At process 912, the control unit 210 receives and processes the surgeon's instructions via the surgeon's eye gaze and/or other inputs. For example, the control unit 210 receives the digitized location information of the surgeon's gaze point from the eye gaze processor 206. The control unit 210 may also receive the preferred magnification input by the surgeon. The control unit 210 may send the location and magnification data to the instrument interface 150 (e.g., the instrument interface 150d or the instrument interface 150f connected to auxiliary imaging module 715 or auxiliary imaging module 722, respectively). As described above, in some embodiments, the instrument interface 150d or instrument interface 150f may send the location and magnification information to the actuator 806 coupled to auxiliary imaging module 715 or auxiliary imaging module 722, and the actuator 806 can drive the auxiliary imaging module to move the corresponding imaging module to the location of the surgeon's gaze point, as shown in FIGS. 8D-8E. The shaft 152d/wrist 713 or shaft 152f/wrist 727, and the corresponding auxiliary imaging module 715 or imaging module 722, respectively, may extend along the longitudinal axis of the shaft toward the surgeon's gaze point for a certain distance that corresponds to the desired level of magnification, and a magnified image 960 (as shown in FIGS. 8D and 8E) may be captured by the corresponding auxiliary imaging module 715 or 722.

At process 914, the auxiliary imaging module (e.g., 715 or 722) captures a secondary or modified image of the region of interest indicated by the surgeon's gaze point after the actuator 806 has adjusted the auxiliary imaging module in response to the surgeon's instructions. The auxiliary imaging module captures a magnified image 960 of the region of interest indicated by the surgeon's gaze point. In some embodiments, the auxiliary imaging module includes the stereo camera 730 shown in FIG. 6C capable of capturing stereo images.

At process 916, the image processing system 800 (shown in FIG. 7A) processes and displays the magnified image 960 of the surgeon's gaze point as an overlaid image on the primary image 950. In some embodiments, the magnified image 960 may have been captured via optical magnification methods (e.g., physical adjustment of the auxiliary imaging module relative to the region of interest represented by the surgeon's eye gaze point). Additionally or alternatively, the magnified image 960 may have been created by the endoscope processor 808 (e.g., via digital manipulation). The endoscope processor 808 can digitize the magnified image 960 captured by the auxiliary imaging module, and then register the magnified image 960 to overlay it atop the primary image 950 on the display 816.

In some embodiments, a common feature-based method (e.g., a common landmark method) may be used to register the magnified image 960 to overlay it atop the primary image 950. For example, in some embodiments, the endoscope processor 808 can identify a common feature, such as a feature 955 of FIG. 8C, which is present in both the primary image 950 and the magnified image 960. The endoscope processor 808 may then spatially align the common feature 955 of the magnified image 960 with common feature 955 in the primary image 950. Although the common feature-based method is described herein as a method of co-registering the magnified image 960 with the primary image 950, is to be understood that any suitable method, such as, by way of non-limiting example, an intensity-based method or feature-based method, may be used to register the magnified image 960 to overlay it upon the primary image 950.

In some embodiments, the display 816 may be the same as the image displays 202a and 202b. When the auxiliary imaging module includes a stereo camera as shown in FIG. 6C, the stereo camera may capture stereo images at the required magnification, and the endoscope processor 808 may generate left and right stereo images to be displayed and to overlay the stereo images of primary image 950 on image displays 202a and 202b, respectively. The surgeon may perceive the stereo images to be a 3D image of the magnified eye gaze point. Additionally or alternatively, the display 816 may comprise an external display, such as the touch screen 146 shown in FIG. 1D.

At process 918, the teleoperational medical system 10 queries whether the magnified image is desired by the surgeon. During the procedure, the surgeon may turn the magnified image ON and OFF or "toggle" the magnified image ON and OFF. After the surgeon views the magnified image 960, the surgeon may send an end instruction to turn OFF, hide, or close the magnified image 960. The surgeon may send the end instruction using any method, for example, the surgeon may press a button at the surgeon console, tap a foot pedal, or send an audio message, or even wink.

Upon receiving an instruction from the surgeon to turn OFF, hide, or close the magnified image 960, the method 900 proceeds to process 920. At process 920, the image processing system 800 turns OFF, hides, or closes the magnified image 960 from the display 816. When the magnified image 960 is turned OFF or hidden from view, the display 816 displays only the primary image 950. The end instruction may be sent to the control unit 210 coupled to the corresponding auxiliary imaging module to deregister magnified image 960 on image display 816, so that the overlaid appearance of magnified image 960 upon the primary image 950 vanishes. In some embodiments, the auxiliary imaging module continues to obtain the magnified image 960 although the magnified image 960 is not displayed on the display 816. In other embodiments, the auxiliary imaging module is deactivated. The control unit 210 may turn OFF the auxiliary imaging module, and move the auxiliary imaging module out of the location of the surgeon's gaze point by controlling the actuator 806. In some embodiments, the auxiliary imaging module may be deactivated only after a predetermined amount of time has passed without the surgeon sending instructions to turn ON the magnified image 816 or otherwise show the magnified image 960 on the display 816 (e.g., via a restart instruction).

In some instances, the surgeon may want to view the magnified image of another region of interest within the surgical field. The method 900 may return to process 908 if the image processing system 900 does not receive instructions to end the magnification or if the system 900 receives instructions to restart magnification from the surgeon. In some embodiments, the surgeon may change his or her eye gaze point, and the new instructions may include capturing and displaying a magnified image of the surgeon's new eye gaze point (e.g., as outlined by processes 910-918). In some embodiments, when the current magnification is insufficient to adequately examine fine structures, the new instructions may direct further magnification or "zooming-in" on the current magnified image of the surgeon's gaze point using the processes 910-918.

FIG. 9 is a flowchart illustrating a method 1000 for using the image processing system 800 to control the imaging devices 112a, 112b, and/or 112c to capture and display primary and secondary images using different imaging modalities according to one embodiment of the present disclosure. When the imaging device 112a of FIG. 6A is used, a primary image in a first imaging modality may be captured and displayed using the primary imaging module 714, and an auxiliary or secondary image may be captured using the auxiliary imaging module 715 using a different imaging modality, such as fluoroscopy or ultrasonography. The auxiliary image may assist the surgeon in characterizing and/or identifying the structures within a region of interest corresponding to the surgeon's gaze point. In some embodiments, the auxiliary imaging module 715 may be configured or adjusted to provide a magnified image of the surgeon's gaze point with a different imaging modality.

In some embodiments, when the imaging device 112b of FIG. 6B is used, a primary image may be captured and displayed using the primary imaging device 112b with the primary imaging module 720, and a secondary or auxiliary image may be captured with a different imaging modality, such as fluoroscopy or ultrasonography, using the auxiliary imaging module 722 of the auxiliary imaging device 112c to characterize and/or identify the structures at the surgeon's gaze point. In some embodiments, the auxiliary imaging module 722 may be adjusted to provide a magnified image of the surgeon's gaze point with a different imaging modality.

Prior to the start of the surgery, the image processing system 800 configured to provide the auxiliary image may be modified based on the surgeon's request. In some embodiments, for example if the surgeon wants to have an auxiliary image in fluoroscopy, the illumination unit 810 may employ an X-Ray source, and the display 816 may be a fluorescent screen. In some embodiments, the image processing system 800 may include any known technology to convert the X-Ray into a visible light output, and may couple the display 816 to the auxiliary imaging module with a CCD video camera. The image processing system 800 for fluoroscopy may allow the images to be recorded and shown on the display 816.

In some embodiments, if the surgeon wants to have an auxiliary image in ultrasonography, the illumination unit 810 may employ a piezoelectric transducer configured to generate ultrasonic sound waves, the auxiliary imaging module may be an ultrasonic scanner operating in an appropriate frequency range, and the endoscope processor 808 may be able to process and transform the received sound waves into a digital image to be displayed on the display 816. Thus, the image processing system 800 may be modified and configured to adopt any suitable technology with any suitable arrangement of required components to be able to capture and display a desired imaging modality based on the surgeon's request.

At process 1002 of method 1000, the primary imaging module is used to capture a primary image of a surgical area. At process 1004, the image processing system 800 processes and displays the primary image on the display 816. At process 1006, the eye tracking system 200 (shown in FIG. 2C) tracks the surgeon's eye gaze point. In some embodiments, the primary image may include stereo images, and a 3D location of the surgeon's gaze point is tracked. Processes 1002, 1004, and 1006 of method 1000 may be substantially similar to processes 902, 904, and 906 of the method 850 shown in FIG. 8A.

At process 1008 of method 1000, the surgeon may direct his or her gaze point at the region of interest, and input instructions (e.g., for viewing a secondary image) using any suitable method. For example, the surgeon may send an instruction by pressing a button at the surgeon console, tapping a foot pedal, sending an audio message, or by winking. The instructions may be sent to the control unit 802 (shown in FIG. 6A) coupled to the auxiliary imaging module. In some embodiments, the instructions may also include information such as a preferred type of imaging modality, and/or a preferred magnification. In addition, the location information of the surgeon's gaze point provided by the eye gaze processor 206 (shown in FIG. 2C) may also be sent to the control unit 802 of the auxiliary imaging module.

At process 1010, similar to the process 911 in FIG. 8A, the image processing system 400 determines whether the surgeon's eye gaze is directed at a region outside of the area represented by the primary image captured by the primary imaging module. If the surgeon's eye gaze point is determined to be outside of the area represented by the primary image, the method 1000 may proceed back to the process 1002 by adjusting the position and orientation of the primary imaging module to form an updated primary image that includes the region corresponding to the surgeon's eye gaze point. When the surgeon's eye gaze point is within the primary image, the method 1000 proceeds to process 1012.

At process 1012, the control unit 802 processes the surgeon's instructions, which were received at process 1008, and prepares the auxiliary imaging module to capture the desired secondary image. In some embodiments, the control unit 802 may direct the actuators 806 to physically position or adjust the auxiliary imaging module to capture the requested image.

At process 1014, the auxiliary imaging module may capture the image with a requested modality according to the surgeon's instructions. Additionally or alternatively, the control unit 802 instructs the endoscope processor 808 to digitally prepare the secondary image with the desired modality.

At process 1016, the endoscope processor 808 processes and displays the requested secondary image on the display 816. In some embodiments, as described above, the endoscope processor 808 processes and identifies a common feature between the secondary image and the primary image, so that the secondary image can be aligned and displayed as an overlay atop the primary image on the image display 816. It is to be understood that other suitable methods may be used to register the secondary image and overlay it on the primary image. In other embodiments, the secondary image may be displayed adjacent to the primary image, in an over-lapping or non-overlapping fashion.

At process 1018, the image processing system 800 determines whether the surgeon desires to continue the auxiliary imaging process and/or to continue viewing the auxiliary image. If continued auxiliary imaging is requested by the surgeon, whether for images on different locations or for images in different modalities, the method 1000 returns to process 1008 to obtain new instructions from the surgeon. If the image processing system 800 determines that the surgeon desires to end auxiliary imaging and/or to discontinue viewing the auxiliary image, the auxiliary imaging process can be ended and/or the auxiliary image can be hidden (e.g., toggled OFF) at process 1020. The processes 1012-1020 of the method 1000 are substantially similar to the processes 912-920 of the method 900 of FIG. 8A.

Figure 10B:
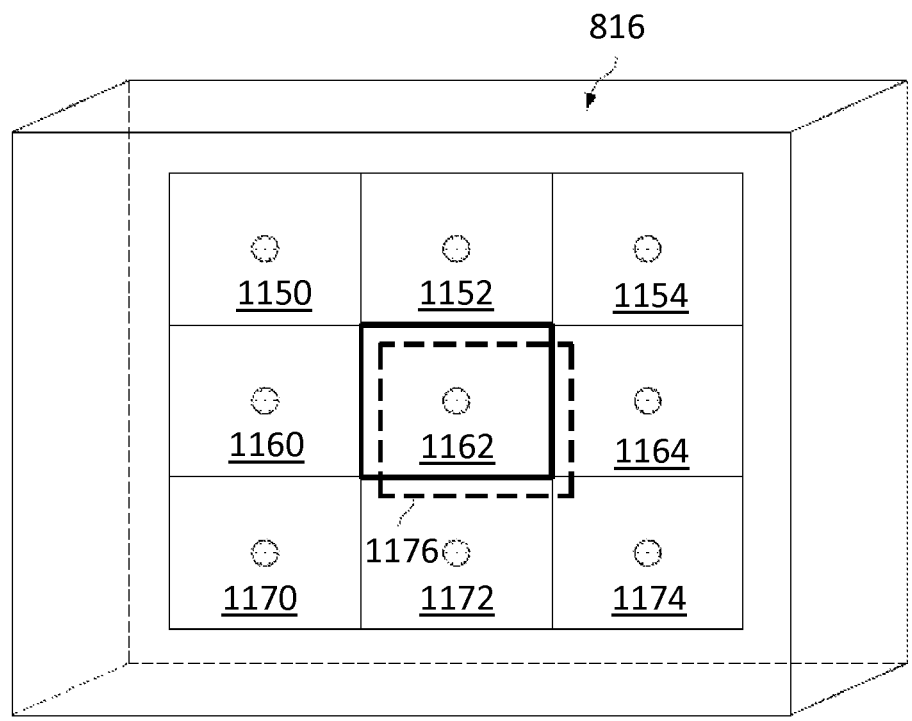
FIGS. 10B-10C illustrates examples of a plurality of images captured and displayed as the endoscope following the surgeon's eye gaze scanning across the primary image on image display according to various embodiments of the present disclosure.

FIG. 10A illustrates a method 1100 for displaying a plurality of images (e.g., images 1150-1154, 1160-1164, and 1170-1174 shown in FIG. 10B) captured as an imaging module follows the surgeon's eye gaze and scans across the area represented by the primary image on the image display 816. FIG. 10B illustrates a plurality of exemplary images that are captured and displayed as the imaging module follows the instructions delivered by the surgeon's eye gaze to scan across the primary image on the image display 816.

At process 1102, the image processing system 800 captures and displays the primary image using a primary imaging module (e.g., the primary imaging module 714 of FIG. 6A or the primary imaging module 720 of FIG. 6B). As described above, the primary imaging module may be a stereoscopic camera configured to capture stereo images of the surgical area. The primary imaging module may also be actuated and controlled by the surgeon at the surgeon console 120 (as shown in FIG. 1C). The primary imaging module may also be adjusted by other personnel in the operating room. In some embodiments, the primary image may be an overview image of a surgical area, such as a patient's abdominal cavity at zero or low magnification. The captured primary images can be processed by the endoscope processor 808, which may be coupled to the primary imaging module. The endoscope processor 808 may receive the primary image and digitize various types of primary image data, such as the location, boundary, and/or magnification level of the primary image. The digitized information may be saved in one or more memories coupled to the endoscope processor 808. The endoscope processor 808 can also process the imaging information of the primary image to display the primary image onto display 816.

At process 1104, the eye tracking system 200 of FIG. 2C tracks the surgeon's eye gaze as the surgeon's eyes scan across the primary image obtained at process 1102. The surgeon's eye gaze may be tracked using the eye trackers 204a and 204b of the eye tracking system 200. The eye gaze processor 206 may process the eye gaze information provided by eye trackers 204a and 204b and digitize data about the surgeon's gaze point, such as the 3D location of the surgeon's gaze point relative to image displays 202 and/or the surgical field. The digitized information may be saved at the one or more memories 208 coupled to eye gaze processor 206. The eye gaze processor 206 may also provide the information to control unit 802 when the surgeon sends instructions based on the surgeon's eye gaze.

At process 1106, the image processing system 800 receives instructions from the surgeon. In some embodiments, the surgeon may identify one or more regions of interest while scanning across the primary image for further investigation. The surgeon may request a modified view (e.g., by way of non-limiting example, a magnified view, a view in a different imaging modality, a highlighted or sharpened view, a brightened or colorized view, or an otherwise graphically adjusted view) of the regions of interest. For example, the surgeon may also request views of the regions of interest in different imaging modalities to further investigate and/or characterize the structures of interest. In some embodiments, the surgeon may request magnified views of the regions of interest to view a more detailed image of structures within the regions of interest.

As the surgeon gazes at a region of interest, the surgeon may input confirmation instructions using any of a variety of suitable input methods. For example, the surgeon may press a corresponding button at the surgeon console, tap a foot pedal, send an audio message, or blink in a particular pattern to input the desired instructions. The confirmation instructions may be sent to the control unit 802, which is coupled to an imaging module that may or may not be the same as the primary imaging module. When the imaging module is different from the primary imaging module 714 or the primary imaging module 720, the auxiliary imaging module 715 of FIG. 6A or the auxiliary imaging module 722 of FIG. 6B may be activated by the control unit 802. In some embodiments, the confirmation instructions may also include the surgeon's desired investigation mode information such as the preferred imaging modality, the desired level of magnification for a "zoomed-in" image, and/or other types of visual/graphic effects. In addition, the 3D location information of the surgeon's gaze point provided by the eye gaze processor 206 is sent to the control unit 802. In some embodiments, before sending the surgeon's confirmation instructions to control unit 802, the image processing system 800 (e.g., the processors of the control unit 802 and/or the eye gaze processor 206) may perform one or more determination processes that are similar to processes 910 and 911 of method 900.

At process 1108, the image processing system 800 processes the surgeon's confirmation instructions. The control unit 802 receives the location information of the surgeon's gaze point from the eye gaze processor 206 and the confirmation instructions (including the surgeon's desired investigation mode information). The control unit 802 may send the location data and the confirmation instructions to the instrument interface 150 that is connected to the appropriate imaging module. In some embodiments, the instrument interface 150 may send the location data and the confirmation instructions to the actuator 806, and the actuator 806 may drive the imaging module to a physical location where the imaging module can obtain the desired image of the region of interest represented by the surgeon's gaze point. For example, when the surgeon has requested a magnified image of the region of interest identified by the surgeon's gaze point, the imaging module may be driven by actuator 806 to extend along the axis of the shaft to capture a magnified image at the desired level of magnification.

At process 1110, the imaging module captures the secondary image of the region of interest indicated by the surgeon's gaze point (e.g., based on the surgeon's instructions sent at process 1106). In particular, in some embodiments, the actuator 1106 adjusts the position and orientation of the imaging module to the region of interest represented by the surgeon's eye gaze point, and the imaging module captures a secondary image of the region of interest for the surgeon's investigation. In some embodiments, the imaging module may also capture the images during the movement of the imaging module across the surgical field toward the region of interest before the imaging module arrives at the region of interest reflected by the surgeon's gaze point. In some embodiments, the imaging module may include a stereo camera as shown in FIG. 6C that can capture stereo images.

At process 1112, the image processing system 800 processes the captured secondary image of the region of interest reflected by the surgeon's gaze point and/or the images captured as the imaging module traveled toward the region of interest. The endoscope processor 808 may digitize the secondary image before presenting the image on the display 816. For example, in some embodiments, the endoscope processor 808 may create a digitally magnified secondary image from the primary image and/or apply various graphical effects to the captured secondary image. The endoscope processor 808 may also generate digitized information of the secondary image, such as location information about the surgeon's gaze point, as well as the position and orientation information about the imaging module used to capture the image. This digitized data may be stored in memory such as, by way of non-limiting example, the memory 208 of FIG. 2C and/or the memory 812 of FIG. 7A.

At process 1114, the image processing system 800 displays the captured secondary image of the region of interest indicated by the surgeon's gaze point on the display 816. In some embodiments, the endoscope processor 808 may compare and identify a common feature between the secondary image and the primary image, and then spatially register the captured image to correctly align and overlay the secondary image atop the primary image using the common feature. It is to be understood that any other suitable method may be used to co-register the captured image and the primary image. In some embodiments, when the imaging module includes a stereo camera as shown in FIG. 6C, the stereo camera may capture stereo images, and the endoscope processor 808 may generate left and right stereo images to be displayed on the display 816 so that the surgeon may perceive a 3D stereo image of the region indicated by eye gaze point.

At process 1116, the image processing system 800 queries whether the surgeon has ended scanning over the primary image. If the surgeon has not finished scanning the primary image, or when the surgeon wishes to double check one or more previously scanned spots, the method 1100 may proceed back to process 1104 to continue to track the surgeon's eye gaze. As shown in FIG. 10B, if the surgeon instructs the system 10 to capture multiple secondary images of his or her gaze points at different locations as he or she scans across the primary image, multiple images 1150-1154, 1160-1164, and 1170-1174 of regions of interest indicated by the gaze points can be processed and shown on the display 816. The images 1150-1154, 1160-1164, and 1170-1174 may be shown on the display 816 as overlaid images atop the primary image or may be shown adjacent to the primary image.

During a procedure, the surgeon may want to stop scanning the primary image at any time for any reason, and the surgeon can send instructions to the system 10 using any suitable method. At process 1116, when the image processing system 800 determines that the surgeon has finished scanning the primary image, the eye gaze processor 206 may confirm the end of the scanning process by informing the surgeon of the termination of the capture of secondary images. In some embodiments, the image processing system 800 may also prompt the surgeon to review the plurality of images and select one image for further evaluation.

Figure 10C:
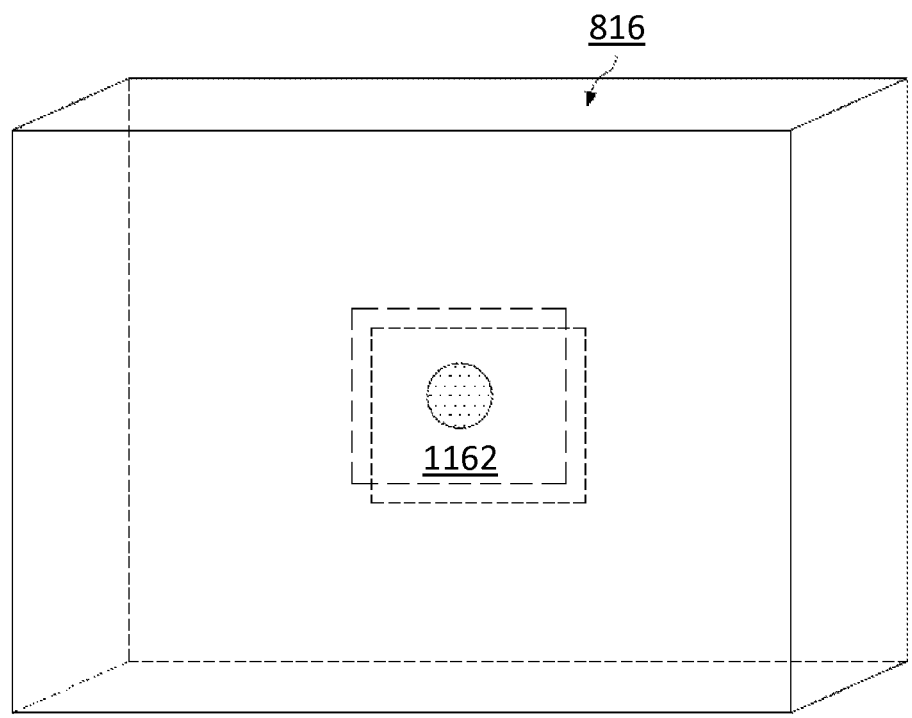

At process 1118, the surgeon may review the plurality of images 1150-1154, 1160-1164, and 1170-1174 showing the plurality of regions of interest tracked and captured using the surgeon's gaze points as the surgeon scanned across the primary image. The surgeon may select one or more images to be shown in the display 816 (e.g., a central image 1162 of the display 816 as shown in FIG. 10C) for further investigation. The surgeon may select the image by using his or her gaze point, or by inputting his or her selection using any other suitable method.

At process 1120, the image processing system 800 processes the surgeon's selection. The surgeon may request a particular imaging effect or type of imaging modality for further investigation of the selected image. For example, the surgeon may instruct the system 800 to display a magnified image 1176 of the selected image 1162, and the magnified image 1176 may be overlaid atop the image 1162, as shown in FIG. 10C. The image processing system 800 coupled to the imaging module performing the requested imaging function may be configured to have any suitable technology in any suitable arrangement to fulfill the surgeon's request. The received selection and image processing instructions may be sent to the control unit 802 to be processed. In some embodiments, the control unit 802 may also exchange information with memory 208 and/or 812 to retrieve the location data of the newly selected region of interest, and the position and orientation data of the imaging module that captured the image of the point of interest. In some embodiments, the retrieved data may be used to adjust the actuators 806 to reposition the imaging module to capture another image of the region of interest corresponding to the selected image based on the surgeon's request.

At process 1122, the requested image of the selected image is captured or digitally created and then displayed on the display 816 for the surgeon's investigation. FIG. 10C illustrates an example of displaying a magnified image 1176 of the image 1162 based on the surgeon's request from the plurality of images of FIG. 10B. In the pictured embodiment, the magnified image 1176 is shown overlaid atop the selected image 1162. In some embodiments, the requested image (e.g., the magnified image 1176) may be shown in a central section of the display 816, irrespective of the original position of the selected image on the display 816. In some embodiments, a stereo camera may be used as the imaging module to capture the magnified image, and stereo images may be displayed to be perceived by the surgeon to be a 3D magnified image of the selected image 1162. In some embodiments, the newly created or captured image may be co-registered to overlie previous captured images using substantially similar methods as previously discussed with respect to process 1114. Processes 1118-1122 may be optional in some surgical operations.

An embodiment of a first medical system comprises an image display configured to display a primary image of a surgical field to a user; an eye tracking system configured to measure gaze point data of the user and to determine a viewing location in the primary image at which the gaze point of the user is directed based on the gaze point data; and an image processing system coupled to the image display and configured to adjust the primary image on the image display based on the viewing location.

In the first medical system, the image processing system is configured to receive an instruction input from the user and to adjust the primary image based upon the instruction.

In the first medical system, the image processing system is configured to adjust the primary image by displaying a secondary image of the viewing location on the image display based upon the gaze point data.

In the first medical system, the image processing system is configured to co-register the secondary image with the primary image so that the secondary image of the viewing location is displayed as an overlay atop the primary image on the image display.

In the first medical system, the image processing system is configured to co-register the secondary image with the primary image so that the secondary image of the viewing location is displayed as adjacent the primary image on the image display. The first medical system further comprises a first imaging module and a second imaging module, wherein the first imaging module is configured to obtain the primary image and the second imaging module is configured to capture the secondary image based upon the gaze point data, the first imaging module and the second imaging module being independently controlled.

In the first medical system, the first and the second imaging modules are component parts of a first imaging device.

In the first medical system, the first imaging module comprises a first imaging device and the second imaging module comprises a second imaging device.

In the first medical system, at least one of the first and second imaging modules includes a stereo camera.

In the first medical system, the first imaging module operates in a first imaging modality and the second imaging module operates in a second imaging modality.

In the first medical system, the first imaging module operates in a first wavelength range and the second imaging module operates in a second wavelength range, wherein the first wavelength range is different than the second wavelength range.

The first medical system includes an eye tracking threshold region within the secondary image, the eye tracking threshold region being smaller than the secondary image, wherein the image processing system is configured to maintain the primary image and the secondary image in response to changes in gaze point data reflecting shifting eye gaze of the user within the eye tracking threshold region.

The first medical system further comprises an endoscope processor coupled to the first imaging module and the second imaging module, the endoscope processor configured to adjust at least one of the primary image or the secondary image in response to the determined viewing location and the instruction input from the user.

In the first medical system, the endoscope processor is configured to independently control at least one function of the first imaging module and at least one function of the second imaging module based upon the determined viewing location in the primary image.

In the first medical system, the endoscope processor is configured to orient and position the second imaging module within the surgical field to capture the secondary image based upon the instruction input from the user and the determined viewing location in the primary image.

The first medical system further comprises a first articulating wrist for adjusting a position and an orientation of the first imaging module, and a second articulating wrist for adjusting a position and an orientation of the second imaging module, wherein the first and second articulating wrists move in response to command signals from the endoscope processor.

The first medical system further comprises a first shaft coupled to the second imaging module, wherein the second imaging module is configured to move along a longitudinal axis of the first shaft in response to command signals from the endoscope processor.

In the first medical system, the endoscope processor is configured to orient and position the first imaging module within the surgical field to maintain the secondary image within the primary image based upon the gaze point data and the determined viewing location in the primary image.

In the first medical system, the endoscope processor is configured to adjust the secondary image obtained by the second imaging module based upon the instruction input from the user.

In the first medical system, the endoscope processor is configured to emphasize the secondary image relative to the primary image on the image display.

In the first medical system, the endoscope processor is configured to digitally alter the secondary image relative to the primary image on the image display.

In the first medical system, the endoscope processor is configured to digitally magnify the secondary image relative to the primary image on the image display.

In the first medical system, the eye tracking system comprises at least two eye trackers.

In the first medical system, the image display is included in the eye tracking system and comprises a left eye image display and a right eye image display.

In the first medical system, the image display is a 3D image display configured to display a 3D image of the primary image to the user.

A first method for operating a surgical system comprises displaying a primary image on an image display; tracking gaze point data of a user using an eye tracking system as the user views the primary image on the image display; and adjusting the primary image based on the gaze point data.

The first method for operating a surgical system further comprises receiving an instruction input from the user.

In the first method for operating a surgical system, adjusting the primary image comprises displaying a secondary image of a region of interest identified by the gaze point data based upon the instruction input from the user.

In the first method for operating a surgical system, the secondary image comprises a visually adjusted portion of the primary image based upon the gaze point data.

In the first method for operating a surgical system, the secondary image comprises a magnified portion of the primary image based upon the gaze point data.

In the first method for operating a surgical system, the secondary image comprises a sharpened portion of the primary image based upon the gaze point data.

In the first method for operating a surgical system, the secondary image comprises a highlighted portion of the primary image based upon the gaze point data.

In the first method for operating a surgical system, the secondary image is of a different imaging modality than the primary image.

The first method for operating a surgical system further comprises capturing the secondary image using an imaging module based upon the instruction input from the user and the gaze point data.

The first method for operating a surgical system further comprises determining a viewing location in the primary image at which the gaze point of the user is directed based on the gaze point data; determining whether the viewing location lies outside of a predetermined eye tracking threshold region; and updating the secondary image based upon the viewing location if the viewing location lies outside the predetermined eye tracking threshold.

In the first method for operating a surgical system, a position and an orientation of an imaging module are adjusted based on the viewing location and the instruction input.

In the first method for operating a surgical system, the imaging module is configured to capture a plurality of secondary images as the user scans across the primary image.

In the first method for operating a surgical system, the primary image is captured using a first imaging module and the secondary image is captured using a secondary imaging module.

In the first method for operating a surgical system, the primary imaging module is located at a first imaging device, and the second imaging module is located at a second imaging device that is different from the first imaging device.

In the first method for operating a surgical system, determining whether the viewing location lies outside of a predetermined eye tracking threshold region includes comparing an average viewing location over a predetermined number of image frames with the predetermined eye tracking threshold region.

In the first method for operating a surgical system, determining whether the viewing location lies outside of a predetermined eye tracking threshold region includes comparing an average viewing location over a predetermined period of time with the predetermined eye tracking threshold region.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the disclosure should be limited only by the following claims, and it is appropriate that the claims be construed broadly and in a manner consistent with the scope of the embodiments disclosed herein.

What is claimed is:

1. A teleoperational medical system for performing a medical procedure in a surgical field, the system comprising:
    an eye tracking unit including:
        an image display configured to display to a user an image of the surgical field;
        at least one eye tracker configured to measure data about a gaze point of the user;
        a processor configured to process the data to determine a viewing location in the displayed image at which the gaze point of the user is directed; and a control unit configured to control at least one function of the teleoperational medical system based upon the determined viewing location.

2. The teleoperational medical system of claim 1 wherein the image display is a 3D image display configured to display to the user a 3D image of the surgical field.

3. The teleoperational medical system of claim 1 further comprising a surgical instrument, wherein the control unit is configured to control at least one function of the surgical instrument in the surgical field based upon the determined viewing location in the displayed image.

4. The teleoperational medical system of claim 3 wherein the surgical instrument is displayed in the displayed image at the viewing location.

5. The teleoperational medical system of claim 3, wherein the control unit is configured to calibrate a 3D position of the surgical instrument in the surgical field based on the determined viewing location in the displayed image.

6. The teleoperational medical system of claim 3 wherein the surgical instrument is an energy application instrument and the control unit is configured to operate the energy application instrument to deliver energy within the surgical field based upon the determined viewing location.

7. The teleoperational medical system of claim 3 wherein the surgical instrument is a fastener application instrument and the control unit is configured to operate the fastener application instrument to deliver a fastener within the surgical field based upon the determined viewing location.

8. The teleoperational medical system of claim 3 wherein the surgical instrument is a fluid management instrument and the control unit is configured to operate the fluid management instrument to convey fluid within the surgical field based upon the determined viewing location.

9. The teleoperational medical system of claim 3, wherein the control unit is configured to deactivate the surgical instrument if the processor determines that the viewing location does not match a position of the surgical instrument for a predetermined length of time.

10. The teleoperational medical system of claim 3, wherein the control unit is configured to move the surgical instrument within the surgical field based on the determined viewing location in the displayed image.

11. The teleoperational medical system of claim 3, wherein the control unit is configured to transfer the control of the surgical instrument from the user to a second user if a determined viewing location in the displayed image of the second user matches a position of the surgical instrument in the image display for a predetermined length of time.

12. The teleoperational medical system of claim 1 further comprising a marking application, wherein the control unit is configured to control the marking application to make a virtual mark in the surgical field that is visible on the image display, based upon the determined viewing location.

13. The teleoperational medical system of claim 1 further comprising an imaging device wherein the control unit is configured to control at least one function of the imaging device in the surgical field based upon the determined viewing location.

14. The teleoperational medical system of claim 13 wherein the at least one function of the imaging device includes movement of the imaging device.

15. The teleoperational medical system of claim 13 wherein the at least one function of the imaging device includes a zoom operation of the imaging device.

16. The teleoperational medical system of claim 13 wherein the at least one function of the imaging device includes a focusing operation of the imaging device.

17. The teleoperational medical system of claim 13 wherein the at least one function of the imaging device includes a mode change operation of the imaging device.

18. The teleoperational medical system of claim 13, wherein the at least one function controlled by the control unit based upon the determined viewing location includes a user log-in function.

19. The teleoperational medical system of claim 1, wherein the control unit is configured to lock out the user from the teleoperational medical system if the processor fails to determine the viewing location on the image display.

20. The teleoperational medical system of claim 1, wherein the control unit is configured to lock out the user from the teleoperational medical system if the at least one eye tracker fails to detect eyes of the user.

21. The teleoperational medical system of claim 1, wherein the image display is configured to display to the user an image of a user interface comprising a plurality of functional options.

22. The teleoperational medical system of claim 21, wherein the control unit is configured to initiate at least one of the plurality of functional options if the determined viewing location matches a position of at least one functional option of the plurality of functional options in the displayed image of the user interface.

23. The teleoperational medical system of claim 21, wherein the control unit is configured to adjust a positional depth of the user interface in the displayed image based on the determined viewing location.

24. The teleoperational medical system of claim 1, wherein the processor is configured to generate an evaluation image of the viewing location at which the gaze point of the user is directed, on an evaluation image display.

25. The teleoperational medical system of claim 1, wherein the image display is configured to display to the user a gaze point of another user viewing the surgical field.

26. The teleoperational medical system of claim 1, wherein the processor is configured to receive an instruction input from the user and to adjust the displayed image based upon the instruction input.

27. The teleoperational medical system of claim 26 wherein the processor is configured to adjust the displayed image by performing a zoom function.

28. The teleoperational medical system of claim 26 wherein the processor is configured to adjust the displayed image by displaying a secondary image of the viewing location, as an overlay, on the image display based upon the gaze point of the user.

29. The teleoperational medical system of claim 28, further comprising a first imaging module and a second imaging module, wherein the first imaging module is configured to obtain the displayed image and the second imaging module is configured to capture the secondary image based upon the gaze point of the user, the first imaging module and the second imaging module being independently controlled.

30. A method for operating a teleoperational medical system, the method comprising:
   displaying an image, including a surgical field image of a surgical field, on an image display; measuring a gaze point of a user in the image display;
   determining a viewing location in the displayed image at which the gaze point of the user is directed; and
   controlling at least one function of the teleoperational medical system based upon the determined viewing location.

31. The method of claim 30 wherein the at least one function of the teleoperational medical system is a three dimensional calibration function that includes comparing the viewing location with a predetermined target in the displayed image with known three dimensional location parameters.

32. The method of claim 30 wherein the at least one function of the teleoperational medical system is an evaluation function that includes displaying the viewing location to another user.

33. The method of claim 30 further comprising providing a teaching location in the displayed image at which a gaze point of another user is directed.

34. The method of claim 30 wherein displayed surgical field image is a 3D image.

35. The method of claim 30 wherein the at least one function of the teleoperational medical system is a surgical instrument operation function including controlling at least one function of a surgical instrument in the surgical field based upon the determined viewing location in the displayed image.

36. The method of claim 35 wherein the surgical instrument is displayed in the surgical field image at the viewing location.

37. The method of claim 34 wherein the at least one function of the teleoperational medical system is an instrument operation function.

38. The method of claim 37 wherein the instrument operation function includes operating an energy application instrument to deliver energy at a location within the surgical field based upon the determined viewing location.

39. The method of claim 37 wherein the instrument operation function includes operating a fastener application instrument to deliver a fastener at a location within the surgical field based upon the determined viewing location.

40. The method of claim 37 wherein the instrument operation function includes operating a fluid management instrument to convey fluid at a location within the surgical field based upon the determined viewing location.

41. The method of claim 35 wherein the instrument operation function includes activating the surgical instrument if the viewing location matches a position of the surgical instrument in the displayed image for a predetermined length of time.

42. The method of claim 35, wherein the instrument operation function includes transferring control of the surgical instrument from the user to a second user if a viewing location of the second user matches a position of the surgical instrument in the displayed image for a predetermined length of time.

43. The method of claim 35 wherein the instrument operation function includes deactivating the surgical instrument if the viewing location does not match a position of the surgical instrument in the displayed image for a predetermined length of time.

44. The method of claim 35 wherein the instrument operation function includes moving the surgical instrument within the surgical field based upon the determined viewing location.

45. The method of claim 30 wherein the at least one function of the teleoperational medical system is a marking function that includes creating a virtual mark in the surgical field that is visible on the image display, based upon the determined viewing location.

46. The method of claim 30 wherein the at least one function of the teleoperational medical system is an imaging device operation function including controlling at least one function of an imaging device in the surgical field based upon the determined viewing location.

47. The method of claim 46 wherein the at least one function of the imaging device includes movement of the imaging device.

48. The method of claim 46 wherein the at least one function of the imaging device includes a zoom operation of the imaging device.

49. The method of claim 46 wherein the at least one function of the imaging device includes a focusing operation of the imaging device.

50. The method of claim 30 wherein the at least one function of the teleoperational medical system is a user log-in function.

51. The method of claim 30 wherein the at least one function of the teleoperational medical system is a lock-out function to lock out the user from the teleoperational medical system if the gaze point of the user is directed away from the displayed image.

52. The method of claim 30 wherein the displayed image includes a user interface comprising a plurality of functional options.

53. The method of claim 52 further comprising initiating at least one of the plurality of functional options if the determined viewing location matches a position of at least one functional option in the displayed image of the user interface.

54. The method of claim 53, further comprising adjusting a positional depth of the user interface in the displayed image based on the determined viewing location.

55. The method of claim 30 further comprising receiving an instruction input from the user and adjusting the displayed image based upon the instruction.

56. The method of claim 55 wherein the displayed image is adjusted by performing a zoom function.

57. The method of claim 55 wherein the displayed image is adjusted by displaying an overlay image on the image display based upon the gaze point of the user.

58. A teleoperational medical system for performing a medical procedure in a surgical field, the surgical system comprising:
an eye tracking unit including:
an image display configured to display to a user an image of the surgical field;
at least one eye tracker configured to measure data about a gaze point of the user;
a processor configured to process the data to determine a viewing location in the displayed image at which the gaze point of the user is directed;
a control unit configured to control at least one function of the teleoperational medical system based upon the determined viewing location; and
a surgical instrument, wherein the control unit is configured to control at least one function of the surgical instrument in the surgical field based upon the determined viewing location in the displayed image, and wherein the control unit is configured to activate the surgical instrument if the processor determines that the viewing location matches a position of the surgical instrument in the image display for a predetermined length of time.

* * * * *